US012661386B2

(12) United States Patent
Wax et al.

(10) Patent No.: US 12,661,386 B2
(45) Date of Patent: Jun. 23, 2026

(54) METHODS RELATED TO THE TREATMENT OF IgA NEPHROPATHY

(71) Applicant: Ares Trading S.A., Aubonne (CH)

(72) Inventors: Stephen Daniel Wax, Newton, MA (US); Roberto Bassi, Corte Madera, CA (US); Hans Guehring, Geisenheim (DE); Christopher Tehlirian, Newton, MA (US); Amy Hui-Chien Kao, Lexington, MA (US)

(73) Assignee: Ares Trading S.A., Aubonne (CH)

( * ) Notice: Subject to any disclaimer, the term of this patent is extended or adjusted under 35 U.S.C. 154(b) by 576 days.

(21) Appl. No.: 18/061,066

(22) Filed: Dec. 2, 2022

(65) Prior Publication Data

US 2023/0210948 A1     Jul. 6, 2023

Related U.S. Application Data

(63) Continuation of application No. PCT/US2021/035161, filed on Jun. 1, 2021.

(60) Provisional application No. 63/033,593, filed on Jun. 2, 2020.

(51) Int. Cl.
| | |
|---|---|
| *C07K 14/705* | (2006.01) |
| *A61K 38/17* | (2006.01) |
| *A61P 13/12* | (2006.01) |
| *C07K 19/00* | (2006.01) |

(52) U.S. Cl.
CPC .......... *A61K 38/1793* (2013.01); *A61P 13/12* (2018.01); *C07K 14/70578* (2013.01); *C07K 19/00* (2013.01); *C07K 2319/30* (2013.01)

(58) Field of Classification Search
CPC .............. C07K 19/00; C07K 14/70578; C07K 14/70596; C07K 2319/00; C07K 2319/30; A61K 38/1793; A61P 13/12
See application file for complete search history.

(56) References Cited

U.S. PATENT DOCUMENTS

| | | | |
|---|---|---|---|
| 851,393 | A | 4/1907 | Bell |
| 7,501,497 | B2 | 3/2009 | Rixon et al. |
| 7,635,767 | B2 | 12/2009 | Rixon et al. |
| 7,772,365 | B2 | 8/2010 | Gross et al. |
| 7,862,814 | B2 | 1/2011 | Rixon et al. |
| 7,951,919 | B2 | 5/2011 | Rixon et al. |
| 7,964,711 | B2 | 6/2011 | Rixon et al. |
| 8,193,316 | B2 | 6/2012 | Fang et al. |
| 8,524,232 | B2 | 9/2013 | Rixon et al. |
| 8,637,021 | B2 | 1/2014 | Del Rio et al. |
| 8,815,238 | B2 | 8/2014 | Rixon et al. |
| 8,852,591 | B2 | 10/2014 | Ponce et al. |
| 8,956,611 | B2 | 2/2015 | Ponce et al. |
| 9,146,242 | B2 | 9/2015 | Dillon et al. |
| 9,346,878 | B2 | 5/2016 | Rixon et al. |
| 9,725,506 | B2 | 8/2017 | Dillon et al. |
| 9,862,760 | B2 | 1/2018 | Abend et al. |
| 10,152,363 | B2 | 12/2018 | Schellenberger et al. |
| 10,435,460 | B2 | 10/2019 | Abend et al. |
| 10,450,366 | B2 | 10/2019 | Abend et al. |
| 10,654,914 | B2 | 5/2020 | Abend et al. |
| RE48,370 | E | 12/2020 | Dillon et al. |
| 11,161,894 | B2 | 11/2021 | Abend et al. |
| 11,274,140 | B2 | 3/2022 | Dillon et al. |
| 11,433,132 | B2 | 9/2022 | Abend et al. |
| 2003/0103986 | A1 | 6/2003 | Rixon et al. |
| 2006/0034852 | A1 | 2/2006 | Rixon et al. |
| 2006/0067933 | A1 | 3/2006 | Gross et al. |
| 2006/0286093 | A1 | 12/2006 | Gross et al. |
| 2008/0260737 | A1 | 10/2008 | Ponce et al. |
| 2009/0148442 | A1 | 6/2009 | Ponce, Jr. et al. |
| 2009/0209006 | A1 | 8/2009 | Rixon et al. |
| 2010/0129384 | A1 | 5/2010 | Rixon et al. |
| 2010/0130728 | A1 | 5/2010 | Rixon et al. |
| 2010/0183609 | A1 | 7/2010 | Rixon et al. |
| 2010/0190961 | A1 | 7/2010 | Eon-Duval et al. |
| 2010/0297122 | A1 | 11/2010 | Del Rio et al. |
| 2011/0229473 | A1 | 9/2011 | Rixon et al. |
| 2013/0309231 | A1 | 11/2013 | Rixon et al. |
| 2013/0330339 | A1 | 12/2013 | Dillon et al. |
| 2014/0220014 | A1 | 8/2014 | Dillon et al. |
| 2014/0328844 | A1 | 11/2014 | Rixon et al. |
| 2017/0088605 | A1 | 3/2017 | Abend et al. |

(Continued)

FOREIGN PATENT DOCUMENTS

| | | |
|---|---|---|
| CN | 101854951 A | 10/2010 |
| CN | 102085367 B | 8/2012 |

(Continued)

OTHER PUBLICATIONS

Rodrigues et al. IgA Nephropathy. Clin J Am Soc Nephrol 12: 677-686, 2017.*
Bhattacharya et al., "Impact of genetic variation on three dimensional structure and function of proteins" PLoS One, Mar. 15, 2017, vol. 12, No. 33, e0171355, 22 pages.
Bork, P. et al., "Go hunting in sequence databases but watch out for the traps," Trends in Genetics, Oct. 1996, vol. 12, No. 10, pp. 425-427.
Bork, "Powers and pitfalls in sequence analysis: the 70% hurdle," Genome Res., Apr. 1, 2000, vol. 10, No. 4, pp. 398-400.
Brenner et al., "Errors in genome annotation," Trends in Genetics, Apr. 1, 1999, vol. 15, No. 4, pp. 132-133.
Doerks et al., "Protein annotation: detective work for function prediction," Trends in Genetics, Jun. 1, 1998, vol. 14, No. 6, pp. 248-250.

(Continued)

*Primary Examiner* — Bridget E Bunner
(74) *Attorney, Agent, or Firm* — COOLEY LLP

(57) ABSTRACT

The present disclosure relates to methods related to the treatment of IgA nephropathy. More specifically, the present disclosure relates to methods for treating a patient having IgA nephropathy (IgAN), to methods for reducing the serum Gd-IgA1 level in a patient having IgA nephropathy (IgAN), to methods for reducing the proteinuria in a patient having IgA nephropathy, to methods for reducing the serum Gd-IgA1 level and the proteinuria in a patient having IgA nephropathy, and further related disclosure.

30 Claims, 13 Drawing Sheets

Specification includes a Sequence Listing.

(56) References Cited

U.S. PATENT DOCUMENTS

| | | | |
|---|---|---|---|
| 2018/0079799 | A1 | 3/2018 | Abend et al. |
| 2019/0002533 | A1 | 1/2019 | Abend et al. |
| 2019/0071488 | A1 | 3/2019 | Abend et al. |
| 2020/0190167 | A1 | 6/2020 | Abend et al. |
| 2020/0384109 | A1 | 12/2020 | Abend et al. |
| 2021/0139577 | A1 | 5/2021 | Dillon et al. |
| 2021/0379183 | A1 | 12/2021 | Van De Laar et al. |
| 2022/0002381 | A1 | 1/2022 | Fang et al. |
| 2022/0363735 | A1 | 11/2022 | Abend et al. |
| 2025/0170213 | A1 | 5/2025 | Wax et al. |

FOREIGN PATENT DOCUMENTS

| | | |
|---|---|---|
| CN | 102085368 B | 6/2013 |
| EP | 2161287 A1 | 3/2010 |
| EP | 3520803 A1 | 8/2019 |
| JP | 2011503038 A | 1/2011 |
| TW | 201803850 A | 2/2018 |
| TW | 201922704 A | 6/2019 |
| WO | WO-02094852 A2 | 11/2002 |
| WO | WO-2004033486 A2 | 4/2004 |
| WO | WO-2008025747 A1 | 3/2008 |
| WO | WO-2008025748 A1 | 3/2008 |
| WO | WO-2008119042 A2 | 10/2008 |
| WO | WO-2008157369 A2 | 12/2008 |
| WO | WO-2009052293 A1 | 4/2009 |
| WO | WO-2009062960 A1 | 5/2009 |
| WO | WO-2009132058 A2 | 10/2009 |
| WO | WO-2009134633 A1 | 11/2009 |
| WO | WO-2017046676 A1 | 3/2017 |
| WO | WO-2018236995 A2 | 12/2018 |
| WO | WO-2019106578 A2 | 6/2019 |
| WO | WO-2019223581 A1 | 11/2019 |
| WO | WO-2021115321 A1 | 6/2021 |
| WO | WO-2021128027 A1 | 7/2021 |
| WO | WO-2021226551 A1 | 11/2021 |
| WO | WO-2021226553 A2 | 11/2021 |
| WO | WO-2021243298 A1 | 12/2021 |
| WO | WO-2021247512 A1 | 12/2021 |
| WO | WO-2021252835 A1 | 12/2021 |
| WO | WO-2022087341 A1 | 4/2022 |
| WO | WO-2022144384 A1 | 7/2022 |

OTHER PUBLICATIONS

Fenton et al., "Rheostat positions: A new classification of protein positions relevant to pharmacogenomics," Medicinal Chem Res, Jul. 2020, vol. 29, pp. 1133-1146.

Fried et al., "Functional analysis of transmembrane activator and calcium-modulating cyclophilin ligand interactor (TACI) mutations associated with common variable immunodeficiency," J Allergy Clin Immunol, Mar. 21, 2011, vol. 128, No. 1, pp. 226-228.

Garcia-Carmona et al., "TACI Isoforms Regulate Ligand Binding and Receptor Function," Front Immunol, Oct. 2, 2018, vol. 9, Article 2125, 14 pages.

Guo, H.H., et al., "Protein tolerance to random amino acid change," Proc Natl Acad Sci, Jun. 22, 2004, vol. 101, No. 25, pp. 9205-9210.

Lee et al., "Monoclonal antibodies and fusion proteins and their complications: Targeting B cells in autoimmune diseases," J Allergy Clin Immunol, Apr. 1, 2010, vol. 125, No. 4, pp. 814-820.

Ngo et al., "Computational complexity, protein structure prediction, and the Levinthal paradox," in The Protein Folding Problem and Tertiary Structure Prediction, Jun. 1, 1994, pp. 492-495.

Skolnick J., et al., "From Genes to Protein Structure and Function: Novel Applications of Computational Approaches in the Genomic Era," Trends in Biotechnology, Jan. 2000, vol. 18, No. 1, pp. 34-39.

Smith et al., "The challenges of genome sequence annotation or 'The devil is in the details,'" Nature Biotech., Nov. 1, 1997, vol. 15, No. 12, pp. 1222-1223.

Tokuriki et al., "Stability effects of mutations and protein evolvability," Curr Opin Structural Biol, Oct. 1, 2009, vol. 19, No. 5, pp. 596-604.

Wells, "Additivity of mutational effects in proteins," Biochemistry, Sep. 1990, vol. 29, No. 37, pp. 8509-8517.

Altschul, et al., "Gapped BLAST and PSI-BLAST: a new generation of protein database search programs," Nuc. Acids Res., Sep. 1, 1997, vol. 25, Issue 17. pp. 3389-3402.

Dillon et al., "B-lymphocyte Stimulator/a Proliferation-inducing Ligand Heterotrimers Are Elevated in the Sera of Patients with Autoimmune Disease and Are Neutralized by Atacicept and B-cell Maturation Antigen-immunoglobulin," Arthritis Res Ther., Apr. 2010, vol. 12, No. 2, 14 pages.

Isenberg et al., "Efficacy and safety of atacicept for prevention of flares in patients with moderate-to-severe systemic lupus erythematosus (SLE): 52-week data (APRIL-SLE randomised trial)," Ann Rheum Dis., Nov. 2015, vol. 74, No. 11, pp. 2006-2015.

Kim, YG et al., "Pathogenic Role of a Proliferation-Inducing Ligand (APRIL) in Murine IgA Nephropathy," PLoS One, Sep. 8, 2015, vol. 10, No. 9, e0137044, 13 pages.

Myette, Jr et al., "A Proliferation Inducing Ligand (APRIL) targeted antibody is a safe and effective treatment of murine IgA nephropathy," Kidney Int., Jul. 2019, vol. 96, No. 1, pp. 104-116.

Shen et al., "Atacicept Dose Rationale for a Phase 3 Study in Patients with High Disease Activity and Auto-Antibody Positive SLE," Arthritis Rheumatol., Oct. 2018, vol. 70, Suppl 9, Abstract No. 2642, 2 pages.

Transmittal of Third-Party Submission for European Application No. 21818634.4, mailed Jun. 5, 2025, 9 pages.

ClinicalTrial.gov, "Efficacy and Safety of Atacicept in IgA Nephropathy", Clinical Trial NCT02808429, Mar. 23, 2020 (Mar. 23, 2020), 8 pages, Retrieved from the Internet <URL:https://clinicaltrials.gov/study/NCT02808429?term=NCT02808429&rank=1&tab=history&a=24#version-content-panel.>.

ClinicalTrial.gov, "Efficacy and Safety of Atacicept in IgA Nephropathy", Clinical Trial NCT02808429, May 28, 2019 (May 28, 2019), 8 pages, Retrieved from the Internet <URL:https://clinicaltrials.gov/study/NCT02808429?term=NCT02808429&rank=1&tab=history&a=23#version-content-panel.>.

ClinicalTrials.gov, "A Study of Telitacicept for Injection (RC18) in Subjects With IgA Nephropathy," Clinical Trial NCT04905212, May 28, 2021, 6 pages, retrieved from <URL:https://clinicaltrials.gov/study/NCT04905212?term=NCT04905212&rank=1&tab=history&a=2#version-content-panel.>.

Extended European Search Report for European Application No. EP21818634.4 mailed Jun. 6, 2024, 9 pages.

Altschul, S. et al., "Protein database searches for multiple alignments," Proc Natl Acad Sci, Jul. 1990, vol. 87, No. 14, pp. 5509-5513.

Anonymous, "Chapter 10: Immunoglobulin A nephropathy," Kidney International Supplements, Jun. 2012, vol. 2, Issue 2, p. 209-217, doi: 10.1038/kisup.2012.23, https://www.kisupplements.org/action/showPdf?pii=S2157-1716%2815%2931059-5.

Barratt, J. et al., The 24-Week Interim Analysis Results of a Randomized, Double-Blind, Placebo-Controlled Phase II Study of Atacicept in Patients With IgA Nephropathy and Persistent Proteinuria, Nephrology Dialysis Transplantation, Jun. 3, 2020, vol. 35, Issue Supplement 3, 1 page.

Barratt, J., "Treatment of IgA Nephropathy: Evolution Over Half a Century," Seminars in Nephrology, Sep. 2018, vol. 38, Issue 5, pp. 531-540.

Bhachu, J.S et al., "Targeted Release-Budesinide (NEFECON) Modifies Circulating IGA-IGG Immune Complex Levels and Levels of Poorly O-Galactosylated IgA in IgAN," Kidney Disease, 2018, vol. 4, pp. 121-122.

Bremer et al., "Protein Delivery with Infusion Pumps," in Protein Delivery: Physical Systems, Sanders and Hendren (eds.), 2002, pp. 239-254.

Canfield, S.M. et al., "The Binding Affinity of Human IgG for its High Affinity Fc Receptor Is Determined by Multiple Amino Acids in the CH2 Domain and Is Modulated by the Hinge Region," J. Exp. Med., vol. 173:1483-1491 (1991).

Cattran, DC et al., "The Oxford classification of IgA nephropathy: rationale, clinicopathological correlations, and classification," Kidney Int. (2009), vol. 76, p. 534-545.

(56)        References Cited

OTHER PUBLICATIONS

Cheung, C. et al., "An Update on the Current State of Management and Clinical Trials for IgA Nephropathy," J. Clin. Med., 2021, vol. 10, No. 11, pp. 2493.

Clinical Trial NCT02808429, "Efficacy and Safety of Atacicept in IgA Nephropathy," U.S. National Library of Medicine, Feb. 25, 2021, 9 pages.

ClinicalTrials.gov, "A Study of Telitacicept for Injection (RC18) in Subjects With IgA Nephropathy," NCT04905212, Dec. 22, 2021, 9 pages.

ClinicalTrials.gov, "History of Changes for Study: NCT04716231 Atacicept in Subjects With IgA Nephropathy (ORIGIN)," Jan. 15, 2021, 4 pages.

ClinicalTrials.gov, "History of Changes for Study: NCT04716231 Atacicept in Subjects With IgA Nephropathy (ORIGIN)," May 21, 2021, 4 pages.

Czerkinsky, C. et al., "Circulating Immune Complexes and Immunoglobulin A Rheumatoid Factor in Patients with Mesangial Immunoglobulin A Nephropathies," Journal of Clinical Investigations, Jun. 1986, vol. 77, pp. 1931-1938.

Descamps-Latscha, B. et al., "Early prediction of IgA nephropathy progression: Proteinuria and AOPP are strong prognostic markers," Kidney Int (2004), vol. 66(4), p. 1606-1612.

Dibase et al., "Oral Delivery of Microencapsulated Proteins," in Protein Delivery: Physical Systems, Sanders and Hendren (eds.), 2002, pp. 255-288.

Do, R. et al., "Attenuation of Apoptosis Underlies B Lymphocyte Stimulator Enhancement of Humoral Immune Response," J Exp Med (2000), vol. 192(7), p. 953-964.

Fellstreom, B. et al., "Targeted-release budesonide versus placebo in patients with IgA nephropathy (NEFIGAN) : a double-blind, randomised, placebo-controlled phase 2b trial," Lancet (2017), vol. 389, p. 2117-2127.

Floege, J et al., "Current Therapy for IgA Nephropathy," J Am Soc Nephrol (2011), vol. 22(10), p. 1785-1794.

Ghosh, S. et al., "Enumerating the role of properdin in the pathogenesis of IgA nephropathy and its possible therapies," International Immunopharmacology, Apr. 2021, vol. 93, Article 107429.

Ginzler, E. et al., "Atacicept in combination with MMF and corticosteroids in lupus nephritis: results of a prematurely terminated trial," Arthritis Res Ther, 2012, vol. 14, No. R33, 7 pages.

Gordon, C. et al., "210 Integrated safety profile of atacicept from all clinical studies to date," Lupas Science & Medicine, 2019, vol. 6, Iss. Suppl. 1, pp. A1-A227.

Gross, J. et al., "TACI-Ig Neutralizes Molecules Critical for B Cell Development and Autoimmune Disease: Impaired B Cell Maturation in Mice Lacking BLyS," Immunity (2001), vol. 15, p. 289-302.

Hinchcliffe, M. et al., "Intranasal insulin delivery and therapy," Adv. Drug Deliv. Rev., vol. 35, Issues 2-3, Feb. 1999, pp. 199-234.

Huang, X. et al., "An Update on Targeted Treatment of IgA Nephropathy: An Autoimmune Perspective," Frontiers in Pharmacology, Aug. 23, 2021, vol. 12, Article 715253, 14 pages.

International Preliminary Report on Patentability for International Application No. PCT/US2021/035161 dated Dec. 15, 2022, 7 pages.

International Search Report and Written Opinion in PCT/US2021/035161, mailed Aug. 30, 2021, 9 pages.

Keagi, C. et al., "Systematic Review of Safety and Efficacy of Atacicept in Treating Immune-Mediated Disorders," Front. Immunol., Mar. 24, 2020, vol. 11, Article 433, 10 pages.

Levey, A. et al., "A New Equation to Estimate Glomerular Filtration Rate," Ann Intern Med. (2009), vol. 150(9), p. 604-612.

Liu, D. et al., "The upregulation of miR-98-5p affects the glycosylation of IgA1 through cytokines in IgA nephropathy," Intl. Immunopharmacology, May 2020, vol. 821 106362.

Lv, J. et al., "Corticosteroid Therapy in IgA Nephropathy," J Am Soc Nephrol (2012), vol. 23(6), p. 1108-1116.

Maixnerva, D., "Emerging Modes of Treatment of IgA Nephropathy," Int. J. Mol. Sci., 2020, vol. 21, No. 23, 16 pages.

Makita, Y. et al., "TLR9 activation induces aberrant IgA glycosylation via APRIL- and IL-6-mediated pathways in IgA nephropathy," Kidney International, Feb. 2020, vol. 97, Issue 2,, pp. 340-349.

Marsters, S. et al., "Interaction of the TNF homologues BLyS and APRIL with the TNF receptor homologues BCMA and TACI," Curr Biol (2000), vol. 10(13), p. 785-788.

Mitragotri, S. et al., "Ultrasound-Mediated Transdermal Protein Delivery," Science, vol. 269, No. 5225, pp. 850-853, 1995.

Moore, P. et al., "BLyS: Member of the Tumor Necrosis Factor Family and B Lymphocyte Stimulator," Science (1999), vol. 285(5425), p. 260-263.

Novak, J. et al., "IgA glycosylation and IgA immune complexes in the pathogenesis of IgA Nephropathy," Semin Nephrol., Jan. 2008, vol. 28(1), pp. 78-87.

Ostro, M. et al., "Use of liposomes as injectable-drug delivery systems," American J. Hosp. Pharm., Aug. 1989, vol. 46, No. 8, pp. 1576-1588.

Patton et al., "Inhaled Insulin," Adv. Drug Deliv. Rev., Feb. 1, 1999, vol. 35, No. 2-3, pp. 235-247.

Pettit, D. et al., "The development of site-specific drug-delivery systems for protein and peptide biopharmaceuticals," Trends in Biotechnology, Dec. 1998, vol. 16, Issue 8, pp. 343-349.

Potts et al., "Transdermal Peptide Delivery Using Electroporation," Pharm. Biotechnol., 1997, vol. 10, pp. 213-214.

Rajasekaran, A. et al., "IgA nephropathy: An interesting autoimmune kidney disease," Am J Medi Sci., Feb. 2021, vol. 361, No. 12, pp. 176-194.

Ranade, V. et al., "Chapter 1: Site-Specific Drug Delivery Using Liposomes as Carriers," Drug Delivery Systems, 1995, 2nd ed., pp. 3-24.

Ranade, V. et al., "Chapters 3 and 4: Role of polymers in drug delivery and Implants in drug delivery," Drug Delivery Systems, 1995, 2nd ed., pp. 95-123.

Roschke, V., et al., "BLyS and APRIL Form Biologically Active Heterotrimers That Are Expressed in Patients with Systemic Immune-Based Rheumatic Diseases," J Immunol (2002), vol. 169, p. 4314-4321.

Samy, E. et al., "211 Identifying lupus patient subsets and specific pharmacodynamic changes through immune cell deconvolution of gene expression data in atacicept-treated patients in the APRIL-SLE study," Lupas Science & Medicine, 2019, vol. 6, Suppl. 1, Art. 211, p. A158.

Samy, E. et al., "Targeting BAFF and APRIL in systemic lupus erythematosus and other antibody-associated diseases," International Reviews of Immunology, Feb. 2017, vol. 36, No. 1, pp. 1-19.

Schneider, et al., "BAFF, a Novel Ligand of the Tumor Necrosis Factor Family, Stimulates B Cell Growth," J. Exp. Med. (1999), vol. 189, No. 11, pp. 1747-1756.

Selvaskandan, H. et al., "New strategies and perspectives on managing IgA nephropathy," Clinical and Experimental Nephrology (2019), vol. 23, pp. 577-588.

Suzuki, Y. et al., "Serum levels of galactose-deficient immunoglobulin (Ig) A1 and related immune complex are associated with disease activity of IgA nephropathy," Clinical and Experimental Nephrology, Jan. 30, 2014, vol. 18, pp. 770-777.

Tao, M. et al., "Structural Features of Human Immunoglobulin G that Determine Isotype-specific Differences in Complement Activation," J. Exp. Med. (1993), vol. 178, pp. 661-667.

Thompson, et al., "BAFF-R, a Newly Identified TNF Receptor That Specifically Interacts with BAFF," Science, 2001, vol. 293, pp. 2108-2111.

Tomana, M. et al., "Galactose-deficient IgA1 in sera of IgA nephropathy patients is present in complexes with IgG," Kidney International, 1997, vol. 52, pp. 509-516.

Tomino, Y., "How to treat patients with chronic kidney disease: With special focus on IgA nephropathy," Nephrology, Oct. 1, 2018, vol. 23, No. S4, pp. 76-79.

WHO Drug Information, 2007, vol. 21, No. 2, 48 pages.

WHO Drug Information, 2019, vol. 33, No. 3, 103 pages.

Wyatt, R. et al., "IgA Nephropathy," The New England Journal of Medicine, 2013, vol. 368, pp. 2402-2414.

Yamasaki, K. et al., "Galactose-Deficient IgA1-Specific Antibody Recognizes GalNAc-Modified Unique Epitope on Hinge Region of

(56)                    References Cited

OTHER PUBLICATIONS

IgA1," Monoclonal Antibodies in Immunodiagnosis and Immunotherapy, 2018, vol. 37, No. 6, p. 252-256.

Yang, C. et al., "Diagnostic Accuracy of Urine Protein/Creatinine Ratio Is Influenced by Urine Concentration," PLoS One, 2015, vol. 10, No. 9, 13 pages.

Yasutake, J. et al., "Novel lectin-independent approach to detect galactose-deficient IgA1 in IgA nephropathy," Nephrol Dial Transplant (2015), vol. 30(8), p. 1315-1321.

Yewey, G. et al., "Chapter 3: Delivery of Proteins from a Controlled Release Injectable Implant," in Protein Delivery: Physical Systems, Pharmaceutical Biotechnology, 2002, vol. 10, Sanders and Hendren (eds.), pp. 93-117.

Zhang, Y. et al., "Update on treatment of immunoglobulin A nephropathy," Oct. 8, 2018, Nephrology, vol. 23, Issue S4, pp. 62-67.

Zhao, N. et al., "The level of galactose-deficient IgA1 in the sera of patients with IgA nephropathy is associated with disease progression," Kidney International, Oct. 1, 2012, vol. 82, Issue 7, pp. 790-796.

EP Application No. 21818634.4, Transmittal of Third Party Submission mailed Jul. 3, 2025; Applicant Ares Trading S.A.; 19 pages.

Merck KGAA et al., Clinical Study Protocol for Clinical Trial No. NCT02808429, Atacicept IgA Nephropathy, CTPN MS700461-0035, uploaded Feb. 4, 2021, posted Feb. 25, 2021, 141 pages.

Tomino, Y. (ed.), IgA Nephropathy Today, Contributions to Nephrology, vol. 157 (entire issue), published in 2007 by S. Karger AG (month not available), 9 pages.

Abcam, "Protein precipitation: Techniques, applications, and considerations," [online], Abcam.com, Sep. 2025, [Retrieved from the Internet on Mar. 31, 2026, at URL: https://www.abcam.com/en-US/knowledge-center/proteins-and-protein-analysis/protein-precipitation]; 12 pages.

Clinical Trial NCT02808429 "Efficacy and Safety of Atacicept in IgA Nephropathy," [online database] U.S. National Library of Medicine Clinical Trial NCT02808429, Version 01, (Jun. 16, 2016); last updated Feb. 25, 2021, [Retrieved from the Internet on Jan. 14, 2026, at URL: https://clinicaltrials.gov/study/NCT02808429?tab=history&a=1#version-content-panel]; 12 pages.

Clinical Trial NCT02808429 "Efficacy and Safety of Atacicept in IgA Nephropathy," [online database] U.S. National Library of Medicine Clinical Trial NCT02808429, Version 02, (Jun. 24, 2016); last updated Feb. 25, 2021; [Retrieved from the Internet on Jan. 14, 2026, at URL: https://clinicaltrials.gov/study/NCT02808429?tab=history&a=2#version-content-panel]; 12 pages.

Clinical Trial NCT02808429 "Efficacy and Safety of Atacicept in IgA Nephropathy," [online database] U.S. National Library of Medicine Clinical Trial NCT02808429, Version 03, (Oct. 14, 2016); last updated Feb. 25, 2021, [Retrieved from the Internet on Jan. 14, 2026, at URL: https://clinicaltrials.gov/study/NCT02808429?tab=history&a=3#version-content-panel]; 12 pages.

Clinical Trial NCT02808429 "Efficacy and Safety of Atacicept in IgA Nephropathy," [online database] U.S. National Library of Medicine Clinical Trial NCT02808429, Version 04, (Mar. 14, 2017); last updated Feb. 25, 2021, [Retrieved on the Internet on Jan. 14, 2026, at URL: https://clinicaltrials.gov/study/NCT02808429?tab=history&a=4#version-content-panel]; 12 pages.

Clinical Trial NCT02808429 "Efficacy and Safety of Atacicept in IgA Nephropathy," [online database] U.S. National Library of Medicine Clinical Trial NCT02808429, Version 05, (May 30, 2017) last updated Feb. 25, 2021, [Retrieved from the Internet on Jan. 14, 2026, at URL: https://clinicaltrials.gov/study/NCT02808429?tab=history&a=5#version-content-panel]; 14 pages.

Clinical Trial NCT02808429 "Efficacy and Safety of Atacicept in IgA Nephropathy," [online database] U.S. National Library of Medicine Clinical Trial NCT02808429, Version 06, (Jun. 28, 2017) last updated Feb. 25, 2021, [Retrieved on the Internet on Jan. 14, 2026, at URL: https://clinicaltrials.gov/study/NCT02808429?tab=history&a=6#version-content-panel]; 14 pages.

Clinical Trial NCT02808429 "Efficacy and Safety of Atacicept in IgA Nephropathy," [online database] U.S. National Library of Medicine Clinical Trial NCT02808429, Version 07, 15 (Aug. 15, 2017); last updated Feb. 25, 2021; [Retrieved from the Internet on Jan. 14, 2026, at URL: https://clinicaltrials.gov/study/NCT02808429?tab=history&a=7#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 08, (Oct. 4, 2017), last updated Feb. 25, 2021; [Retrieved from the Internet on Jan. 14, 2026, at URL: https://clinicaltrials.gov/study/NCT02808429?tab=history&a=8#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 09, (Nov. 27, 2017); last updated Feb. 25, 2021; [Retrieved from the Internet on Jan. 14, 2026, at URL: https://clinicaltrials.gov/study/NCT02808429?tab=history&a=9#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 10, (Dec. 18, 2017); last updated Feb. 25, 2021; [Retrieved from the Internet on Jan. 14, 2026, at URL: https://clinicaltrials.gov/study/NCT02808429?tab=history&a=10#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 11, (Jan. 16, 2018), last updated Feb. 25, 2021; [Retrieved from the Internet on Jan. 14, 2026, at URL: https://clinicaltrials.gov/study/NCT02808429?tab=history&a=11#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 12, (Feb. 15, 2018); last updated Feb. 25, 2021; [Retrieved from the Internet on Jan. 14, 2026, at URL: https://clinicaltrials.gov/study/NCT02808429?tab=history&a=12#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 13, Mar. 20, 2018 (Mar. 20, 2018), last updated Feb. 25, 2021; [Retrieved on the Internet on Jan. 14, 2026, at URL: https://clinicaltrials.gov/study/NCT02808429?tab=history&a=13#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 14, (Apr. 11, 2018); last updated Feb. 25, 2021; [Retrieved from the Internet on Jan. 14, 2026, at URL: https://clinicaltrials.gov/study/NCT02808429?tab=history&a=14#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 15, (May 30, 2018); last updated Feb. 25, 2021; [Retrieved from the Internet on Jan. 14, 2026, at URL: https://clinicaltrials.gov/study/NCT02808429?tab=history&a=15#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 16, (Jun. 27, 2018), last updated Feb. 25, 2021; [Retrieved from the Internet on Jan. 14, 2026, at URL: https://clinicaltrials.gov/study/NCT02808429?tab=history&a=16#version-content-panel; 16 pages.

Clinical Trial NCT02808429 "Efficacy and Safety of Atacicept in IgA Nephropathy," [online database] U.S. National Library of Medicine Clinical Trial NCT02808429, Version 17, (Aug. 1, 2018), last updated Feb. 25, 2021; [Retrieved from the Internet on Jan. 14, 2026, at URL: https://clinicaltrials.gov/study/NCT02808429?tab=history&a=17#version-content-panel]; 16 pages.

Clinical Trial NCT02808429 "Efficacy and Safety of Atacicept in IgA Nephropathy," [online database] U.S. National Library of Medicine Clinical Trial NCT02808429, Version 18, (Sep. 13, 2018); last updated Feb. 25, 2021; [Retrieved from the Internet on Jan. 14, 2026, at URL: https://clinicaltrials.gov/study/NCT02808429?tab=history&a=18#version-content-panel]; 16 pages.

(56)  References Cited

OTHER PUBLICATIONS

Clinical Trial NCT02808429, "Efficacy and Safety of Atacicept in IgA Nephropathy," [online database] U.S. National Library of Medicine Clinical Trial NCT02808429, Version 19, (Oct. 15, 2018), last updated Feb. 25, 2021; [Retrieved from the Internet on Jan. 14, 2026, at URL: https://clinicaltrials.gov/study/NCT02808429?tab=history&a=19#version-content-panel]; 16 pages.

Clinical Trial NCT02808429, "Efficacy and Safety of Atacicept in IgA Nephropathy," [online database] U.S. National Library of Medicine Clinical Trial NCT02808429, Version 20, (Dec. 4, 2018), last updated Feb. 25, 2021; [Retrieved from the Internet on Jan. 14, 2026, at URL: https://clinicaltrials.gov/study/NCT02808429?tab=history&a=20#version-content-panel]; 16 pages.

Clinical Trial NCT02808429, "Efficacy and Safety of Atacicept in IgA Nephropathy," [online database] U.S. National Library of Medicine Clinical Trial NCT02808429, Version 21, (Feb. 8, 2019), last updated Feb. 25, 2021; [Retrieved from the Internet on Jan. 14, 2026, on Jan. 14, 2026, at URL: https://clinicaltrials.gov/study/NCT02808429?tab=history&a=21#version-content-panel]; 16 pages.

Clinical Trial NCT02808429, "Efficacy and Safety of Atacicept in IgA Nephropathy," [online database] U.S. National Library of Medicine, Version 22, (Apr. 29, 2019), last updated Feb. 25, 2021; [Retrieved from the Internet on Jan. 14, 2026, at URL: https://clinicaltrials.gov/study/NCT02808429?tab=history&a=22#version-content-panel]; 15 pages.

Clinical Trial NCT04905212, "A Study of Telitacicept for Injection (RC18) in Subjects With IgA Nephropathy," [online database] U.S. National Library of Medicine, Version 12, (Dec. 19, 2022), last updated Dec. 6, 2023, [Retrieved from the Internet on Mar. 16, 2023, at URL: https://clinicaltrials.gov/study/NCT04905212?term=NCT04905212&rank=1&tab=history&a=12#version-content-panel]; 9 pages.

Clinical Trial NCT04287985, "Safety and Efficacy Study of VIS649 for IgA Nephropathy," [online database] U.S. National Library of Medicine, Version 1, Feb. 25, 2020 (Feb. 25, 2020), last updated Nov. 21, 2024 [Retrieved from the Internet on Apr. 1, 2026, at URL: https://clinicaltrials.gov/study/NCT04287985?tab=history&a=1#version-content-panel]; 7 pages.

Clinical Trial NCT04287985, "Safety and Efficacy Study of VIS649 for IgA Nephropathy," [online database] U.S. National Library of Medicine, Version 3, Jul. 20, 2020 (Jul. 20, 2020), last updated Nov. 21, 2024 [Retrieved from the Internet on Apr. 1, 2026, at URL: https://clinicaltrials.gov/study/NCT04287985?tab=history&a=1#version-content-panel]; 7 pages.

Hymowitz et al., "Structures of APRIL-Receptor Complexes," J Biol Chem, Feb. 2005, vol. 280, No. 8, pp. 7218-7227.

Shidham et al., "Timed Urine Collections Are Not Needed to Measure Urine Protein Excretion in Clinical Practice," Am J Kidney Dis., Jan. 1, 2006, vol. 47, No. 1, pp. 8-14.

U.S. Appl. No. 19/462,985, Non-Final Office Action mailed Apr. 1, 2026; Inventor Wax, Stephen Daniel; 16 pages.

U.S. Appl. No. 19/054,646, Non-Final Office Action mailed Jan. 9, 2026; Inventor Wax, Stephen Daniel et al.; 35 pages.

U.S. Appl. No. 19/462,966, filed Jan. 28, 2026; Inventor Wax, Stephen Daniel et al.

U.S. Appl. No. 19/462,967, filed Jan. 28, 2026; Inventor Wax, Stephen Daniel et al.

U.S. Appl. No. 19/462,985, filed Jan. 28, 2026; Inventor Wax, Stephen Daniel et al.

U.S. Appl. No. 19/462,999, filed Jan. 28, 2026; Inventor Wax, Stephen Daniel et al.

* cited by examiner

FIG. 2A
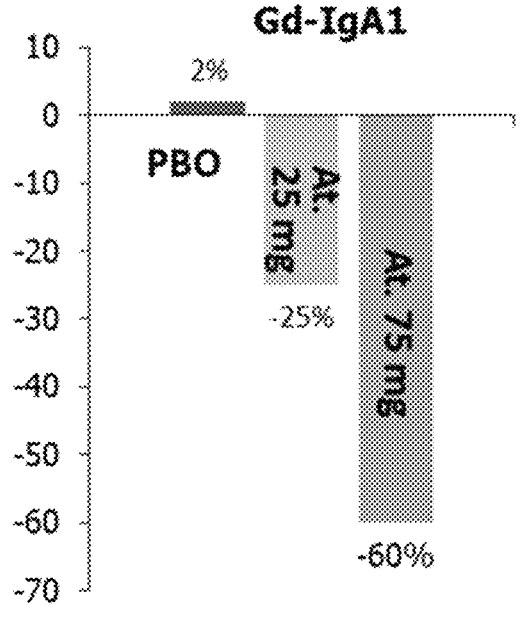
FIG. 2B
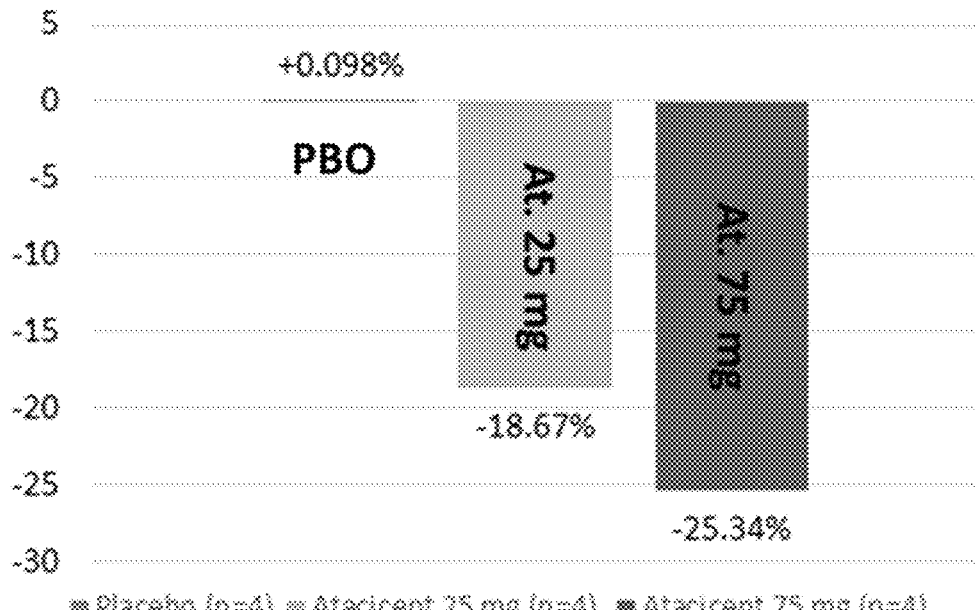

FIG. 5A

SEQUENCE LISTING

```
Sequence total quantity: 11
SEQ ID NO: 1              moltype = AA  length = 81
FEATURE                   Location/Qualifiers
REGION                    1..81
                          note = Amino acid sequence of fragment of TACI
                           extracellular region included in Atacicept
source                    1..81
                          mol_type = protein
                          organism = synthetic construct
SEQUENCE: 1
AMRSCPEEQY WDPLLGTCMS CKTICNHQSQ RTCAAFCRSL SCRKEQGKFY DHLLRDCISC   60
ASICGQHPKQ CAYFCENKLR S                                             81

SEQ ID NO: 2              moltype = AA  length = 227
FEATURE                   Location/Qualifiers
REGION                    1..227
                          note = Amino acid sequence of Ig region included in
                           Atacicept
source                    1..227
                          mol_type = protein
                          organism = synthetic construct
SEQUENCE: 2
DKTHTCPPCP APEAEGAPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPS SIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 3              moltype = AA  length = 313
FEATURE                   Location/Qualifiers
REGION                    1..313
                          note = Amino acid sequence of Atacicept
source                    1..313
                          mol_type = protein
                          organism = synthetic construct
SEQUENCE: 3
AMRSCPEEQY WDPLLGTCMS CKTICNHQSQ RTCAAFCRSL SCRKEQGKFY DHLLRDCISC   60
ASICGQHPKQ CAYFCENKLR SEPKSSDKTH TCPPCPAPEA EGAPSVFLFP PKPKDTLMIS  120
RTPEVTCVVV DVSHEDPEVK FNWYVDGVEV HNAKTKPREE QYNSTYRVVS VLTVLHQDWL  180
NGKEYKCKVS NKALPSSIEK TISKAKGQPR EPQVYTLPPS RDELTKNQVS LTCLVKGFYP  240
SDIAVEWESN GQPENNYKTT PPVLDSDGSF FLYSKLTVDK SRWQQGNVFS CSVMHEALHN  300
HYTQKSLSLS PGK                                                    313

SEQ ID NO: 4              moltype = AA  length = 333
FEATURE                   Location/Qualifiers
REGION                    1..333
                          note = Amino acid sequence of Telitacicept
source                    1..333
                          mol_type = protein
                          organism = synthetic construct
SEQUENCE: 4
SRVDQEERFP QGLWTGVAMR SCPEEQYWDP LLGTCMSCKT ICNHQSQRTC AAFCRSLSCR   60
KEQGKFYDHL LRDCISCASI CGQHPKQCAY FCENKLRSPV NLPPELDKTH TCPPCPAPEA  120
EGAPSVFLFP PKPKDTLMIS RTPEVTCVVV DVSHEDPEVK FNWYVDGVEV HNAKTKPREE  180
QYNSTYRVVS VLTVLHQDWL NGKEYKCKVS NKALPSSIEK TISKAKGQPR EPQVYTLPPS  240
RDELTKNQVS LTCLVKGFYP SDIAVEWESN GQPENNYKTT PPVLDSDGSF FLYSKLTVDK  300
SRWQQGNVFS CSVMHEALHN HYTQKSLSLS PGK                              333

SEQ ID NO: 5              moltype = AA  length = 323
FEATURE                   Location/Qualifiers
REGION                    1..323
                          note = Amino acid sequence of TACI-Ig fusion protein T1 of
                           EP 2161287 B1
source                    1..323
                          mol_type = protein
                          organism = synthetic construct
SEQUENCE: 5
SRVDQEERFP QGLWTGVAMR SCPEEQYWDP LLGTCMSCKT ICNHQSQRTC AAFCRSLSCR   60
```

```
KEQGKFYDHL LRDCISCASI CGQHPKQCAY FCENKLDKPH TCPLCPAPEL LGGPSVFLFP  120
KPPKDTLMIS RTPEVTCVVV DVSHEDPEVK FNWYVDGVEV HNAKTKPREE QYNSTYRVVS  180
VLTVLHQDWL NGKEYKCKVS NKALPAPIEK TISKAKGQPR EPQVYTLPPS RDELTKNQVS  240
LTCLVKGFYP SDIAVEWESN GQPENNYKAT PPVLDSDGSF FLYSKLTVDK SRWQQGNVFS  300
CSVMHEALHN HYTQKSLSLS PGK                                         323

SEQ ID NO: 6               moltype = AA   length = 333
FEATURE                    Location/Qualifiers
REGION                     1..333
                           note = Amino acid sequence of TACI-Ig fusion protein T2 of
                            EP 2161287 B1
source                     1..333
                           mol_type = protein
                           organism = synthetic construct
SEQUENCE: 6
SRVDQEERFP QGLWTGVAMR SCPEEQYWDP LLGTCMSCKT ICNHQSQRTC AAFCRSLSCR  60
KEQGKFYDHL LRDCISCASI CGQHPKQCAY FCENKLRSPV NLPPELDKPH TCPLCPAPEL  120
LGGPSVFLFP PKPKDTLMIS RTPEVTCVVV DVSHEDPEVK FNWYVDGVEV HNAKTKPREE  180
QYNSTYRVVS VLTVLHQDWL NGKEYKCKVS NKALPAPIEK TISKAKGQPR EPQVYTLPPS  240
RDELTKNQVS LTCLVKGFYP SDIAVEWESN GQPENNYKAT PPVLDSDGSF FLYSKLTVDK  300
SRWQQGNVFS CSVMHEALHN HYTQKSLSLS PGK                              333

SEQ ID NO: 7               moltype = AA   length = 322
FEATURE                    Location/Qualifiers
REGION                     1..322
                           note = Amino acid sequence of TACI-Ig fusion protein T3 of
                            EP 2161287 B1
source                     1..322
                           mol_type = protein
                           organism = synthetic construct
SEQUENCE: 7
SRVDQEERFP QGLWTGVAMR SCPEEQYWDP LLGTCMSCKT ICNHQSQRTC AAFCRSLSCR  60
CGQHPKQCAY FCENKLRSPV NLPPELGGGG GGGGGDKPHT CPLCPAPELL GGPSVFLFPP  120
KPKDTLMISR TPEVTCVVVD VSHEDPEVKF NWYVDGVEVH NAKTKPREEQ YNSTYRVVSV  180
LTVLHQDWLN GKEYKCKVSN KALPAPIEKT ISKAKGQPRE PQVYTLPPSR DELTKNQVSL  240
TCLVKGFYPS DIAVEWESNG QPENNYKATP PVLDSDGSFF LYSKLTVDKS RWQQGNVFSC  300
SVMHEALHNH YTQKSLSLSP GK                                          322

SEQ ID NO: 8               moltype = AA   length = 342
FEATURE                    Location/Qualifiers
REGION                     1..342
                           note = Amino acid sequence of TACI-Ig fusion protein
                            according to SEQ 4 of US 8193316 B2
source                     1..342
                           mol_type = protein
                           organism = synthetic construct
SEQUENCE: 8
SRVDQEERFP QGLWTGVAMR SCPEEQYWDP LLGTCMSCKT ICNHQSQRTC AAFCRSLSCR  60
KEQGKFYDHL LRDCISCASI CGQHPKQCAY FCENKLRSPV NLPPELGGGG GGGGGDKPHT  120
CPLCPAPELL GGPSVFLFPP KPKDTLMISR TPEVTCVVVD VSHEDPEVKF NWYVDGVEVH  180
NAKTKPREEQ YNSTYRVVSV LTVLHQDWLN GKEYKCKVSN KALPAPIEKT ISKAKGQPRE  240
PQVYTLPPSR DELTKNQVSL TCLVKGFYPS DIAVEWESNG QPENNYKATP PVLDSDGSFF  300
LYSKLTVDKS RWQQGNVFSC SVMHEALHNH YTQKSLSLSP GK                    342

SEQ ID NO: 9               moltype = AA   length = 313
FEATURE                    Location/Qualifiers
REGION                     1..313
                           note = Amino acid sequence of TACI-Ig fusion protein T4 of
                            EP 2161287 B1
source                     1..313
                           mol_type = protein
                           organism = synthetic construct
SEQUENCE: 9
AMRSCPEEQY WDPLLGTCMS CKTICNHQSQ RTCAAFCRSL SCRKEQGKFY DHLLRDCISC  60
ASICGQHPKQ CAYFCENKLR SEPKSSDKPH TCPLCPAPEL LGGPSVFLFP PKPKDTLMIS  120
RTPEVTCVVV DVSHEDPEVK FNWYVDGVEV HNAKTKPREE QYNSTYRVVS VLTVLHQDWL  180
NGKEYKCKVS NKALPAPIEK TISKAKGQPR EPQVYTLPPS RDELTKNQVS LTCLVKGFYP  240
SDIAVEWESN GQPENNYKAT PPVLDSDGSF FLYSKLTVDK SRWQQGNVFS CSVMHEALHN  300
HYTQKSLSLS PGK                                                    313

SEQ ID NO: 10              moltype = AA   length = 293
FEATURE                    Location/Qualifiers
REGION                     1..293
                           note = Amino acid sequence of human TACI
source                     1..293
                           mol_type = protein
                           organism = synthetic construct
SEQUENCE: 10
MSGLGRSRRG GRSRVDQEER FPQGLWTGVA MRSCPEEQYW DPLLGTCMSC KTICNHQSQR  60
```

-continued

```
TCAAFCRSLS CRKEQGKFYD HLLRDCISCA SICGQHPKQC AYFCENKLRS PVNLPPELRR   120
QRSGEVENNS DNSGRYQGLE HRGSEASPAL PGLKLSADQV ALVYSTLGLC LCAVLCCFLV   180
AVACFLKKRG DPCSCQPRSR PRQSPAKSSQ DHAMEAGSPV STSPEPVETC SFCFPECRAP   240
TQESAVTPGT PDPTCAGRWG CHTRTTVLQP CPHIPDSGLG IVCVPAQEGG PGA         293

SEQ ID NO: 11           moltype = AA  length = 166
FEATURE                 Location/Qualifiers
REGION                  1..166
                        note = Amino acid sequence of human TACI extracellular
                         domain
source                  1..166
                        mol_type = protein
                        organism = synthetic construct
SEQUENCE: 11
MSGLGRSRRG GRSRVDQEER FPQGLWTGVA MRSCPEEQYW DPLLGTCMSC KTICNHQSQR   60
TCAAFCRSLS CRKEQGKFYD HLLRDCISCA SICGQHPKQC AYFCENKLRS PVNLPPELRR   120
QRSGEVENNS DNSGRYQGLE HRGSEASPAL PGLKLSADQV ALVYST               166
```

METHODS RELATED TO THE TREATMENT OF IgA NEPHROPATHY

CROSS REFERENCE TO RELATED APPLICATIONS

This application is a continuation of International Application No. PCT/US2021/035161, filed Jun. 1, 2021, which claims the benefit of U.S. Provisional Application No. 63/033,593, filed Jun. 2, 2020, each of which is incorporated by reference herein in its entirety for all purposes.

REFERENCE TO AN ELECTRONIC SEQUENCE LISTING

The contents of the electronic sequence listing (VETH_011_01US_SeqList_ST26.xml; Size: 18,134 bytes; and Date of Creation: Oct. 25, 2022) is herein incorporated by reference in its entirety.

TECHNICAL FIELD

The present disclosure relates generally to methods for the treatment of IgA nephropathy. More specifically, the present disclosure relates to methods for treating a patient having IgA nephropathy (IgAN), to methods for reducing the serum Gd-IgA1 level in a patient having IgA nephropathy (IgAN), to methods for reducing the proteinuria in a patient having IgA nephropathy, to methods for reducing the serum Gd-IgA1 level and the proteinuria in a patient having IgA nephropathy, and further related disclosure.

BACKGROUND

Immunoglobulin A nephropathy (IgAN), also known as Berger's disease, is the most common primary glomerulonephritis in the world. It is estimated that there are about 10 cases per million people per year in the United States, and 20-40 cases per million people per year in Asia.

Both clinically and pathologically, the manifestation of IgAN varies. In classical IgAN, the disease involves gross hematuria following an infection. However, more commonly IgAN involves asymptomatic microscopic hematuria either with or without proteinuria. In particular, persistent proteinuria (especially with a urine protein:creatinine ratio (UPCR)>1 mg/mg) in IgAN patients is associated with an increased risk of renal failure. Up to 40% of all subjects suffering from IgAN progress over time to end stage renal disease (ESRD).

The pathogenic mechanism of IgAN is not fully understood. It is believed that the formation of IgA-containing circulating immune complexes (CIC) that deposit in the kidneys trigger glomerular inflammation and tubulointerstitial scarring. One substrate for immune complex formation is galactose deficient immunoglobulin A1 (Gd-IgA1). Compared to normal IgA1 antibodies, these Gd-IgA1 antibodies lack galactose on the O-linked glycans of their hinge region. The glycosylation-deficient Gd-IgA1 proteins are thought to trigger the formation of IgA and IgG autoantibodies against the Gd-IgA1 hinge region. The formation of circulating IgA-containing immune complexes that deposit in the kidneys trigger glomerular inflammation and tubulointerstitial scarring. Some references associated with galactose-deficient IgA1 (Gd-IgA1) in IgA nephropathy include: Liu D et al., 2020; Makita Y et al., 2020; Zhao et al., Kidney International 2012.

As of today, the central component of supportive care for IgAN patients consists of appropriate blood pressure (BP) control and proteinuria management using Angiotensin Converting Enzyme Inhibitors (ACEis) or Angiotensin Receptor Blockers (ARBs) (International Society of Nephrology, 2012). The use of ACEis has been shown in randomized controlled studies to decrease proteinuria and correlates with improved renal survival (Descamps-Latascha et al., 2004). Used in combination, ACEis and ARBs may have an additive effect in decreasing proteinuria. However, in the long run ACEis and ARBs do not allow to halt or reverse the ongoing proteinuria and progression to renal failure linked to IgAN.

Other treatments, such as corticosteroids (CS) and immunosuppressants, have not been shown to definitively improve renal outcomes (Floege et al., 2011). Although a short course of CS is recommended for subjects with preserved kidney function who have persistent proteinuria despite adequate blood pressure control and treatment with ACEis (International Society of Nephrology, 2012), a recent review of published clinical trials suggests that CS may only improve renal survival in selected situations, and questions about safety persist (Lv 2012).

Thus, there is a significant unmet medical need for the treatment of IgAN since available treatments for IgAN are currently inadequate. Given that outcomes in subjects with IgAN remain poor, particularly with respect to development of ESRD and overall mortality, IgAN cannot be considered an indolent disease and better treatments are required. In particular, so far there is no treatment available that effectively reduces the formation and deposition of circulating Gd-IgA1 immune complexes in the kidneys. Thus, at present no intervention exists with the potential for true disease modification by reduction of a causal disease factor, in particular for patients with persistent proteinuria and high protein content in the urine.

Accordingly, there is a need in the art for improved ways to treat IgAN, in particular in IgAN patients with persistent proteinuria and/or high levels of proteinuria. Moreover, there is a need in the art for improved ways to reduce the plasma level of Gd-IgA1 in patients having IgAN, in particular in IgAN patients with persistent proteinuria and/or high levels of proteinuria, preferably by a method that can be applied over an extended period of time. Moreover, there is a need in the art for improved ways to reduce the proteinuria in a patient having IgA nephropathy, in particular in IgAN patients with persistent proteinuria and/or high levels of proteinuria, preferably by a method that can be applied over an extended period of time.

The present disclosure overcomes the above-described problems and addresses the above-described needs.

SUMMARY

The present disclosure relates to transmembrane activator and calcium modulator and cyclophilin ligand-interactor (TACI)-immunoglobulin (Ig) fusion molecules and provides methods for treating a patient having IgA nephropathy (IgAN) and related methods.

The present invention is, in part, based on the surprising observation that administration of a TACI-Ig fusion molecule like atacicept allows to strongly reduce serum levels of Gd-IgA1 in IgAN patients, even for strongly affected patients with a high proteinuria level. Moreover, it was found that this approach results in less side effects and allows for longer treatment than IgAN treatments known from the state of the art.

According to one aspect, the present disclosure relates to a method for treating a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a method for reducing the serum Gd-IgA1 level in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a method for reducing the proteinuria in a patient having IgA nephropathy, said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a method for reducing the serum Gd-IgA1 level and the proteinuria in a patient having IgA nephropathy, said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte (ii) a human immunoglobulin-constant domain.

According to another aspect, the present disclosure relates to a method of treating IgA nephropathy (IgAN) in a patient, said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain, and wherein said method comprises determining the level of proteinuria in said patient.

According to another aspect, the present disclosure relates to a method for treating IgA nephropathy (IgAN) in a patient, said method comprising the steps of (1) measuring the protein level in the urine of said patient; and (2) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a method of treating IgA nephropathy (IgAN) in a patient, said method comprising the steps of (1) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain;

(2) measuring the protein level in the urine of said patient; and (3) continuing to administer said TACI-Ig fusion molecule to said patient if said patient has proteinuria.

According to another aspect, the present disclosure relates to a method of treating IgA nephropathy (IgAN) in a patient, said method comprising the steps of (1) administering to said patient an angiotensin converting enzyme inhibitor (ACEi) and/or an angiotensin receptor blocker (ARB);

(2) measuring the protein level in the urine of said patient; and (3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in the treatment of IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (i) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level and the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level and the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy in a patient, wherein the TACI-Ig fusion molecule comprises:

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

BRIEF DESCRIPTION OF THE FIGURES

In the following, reference is made to the figures. All methods referred to in the figure descriptions below were carried out as described in detail in the examples.

FIGS. 2A-2C summarizes interim results obtained in Example 1 by week 24. FIG. 2A shows the median change in serum Gd-IgA1 from baseline (day 1) at week 24. FIG. 2B shows the median change in 24-hour UPCR from baseline (day 1) at week 24. FIG. 2C shows the median change in serum IgA, IgG and IgM at week 24 in the study of Example 1. Bars from left to right show the values for Placebo, Atacicept 25 mg, and Atacicept 75 mg.

FIGS. 5A-5G shows median % change in serum concentration vs. baseline (the value of day 1 before the first TACI-Ig administration) for: serum IgA (FIG. 5A), serum IgG (FIG. 5B), serum IgM (FIG. 5C), serum Gd-IgA1 (FIG. 5D), complement C3 in serum (FIG. 5E), complement C4 in serum (FIG. 5F), and the median % change in the estimated glomerular filtration rate (GFR) (FIG. 5G), in the study of Example 1.

DETAILED DESCRIPTION

Figure 1:
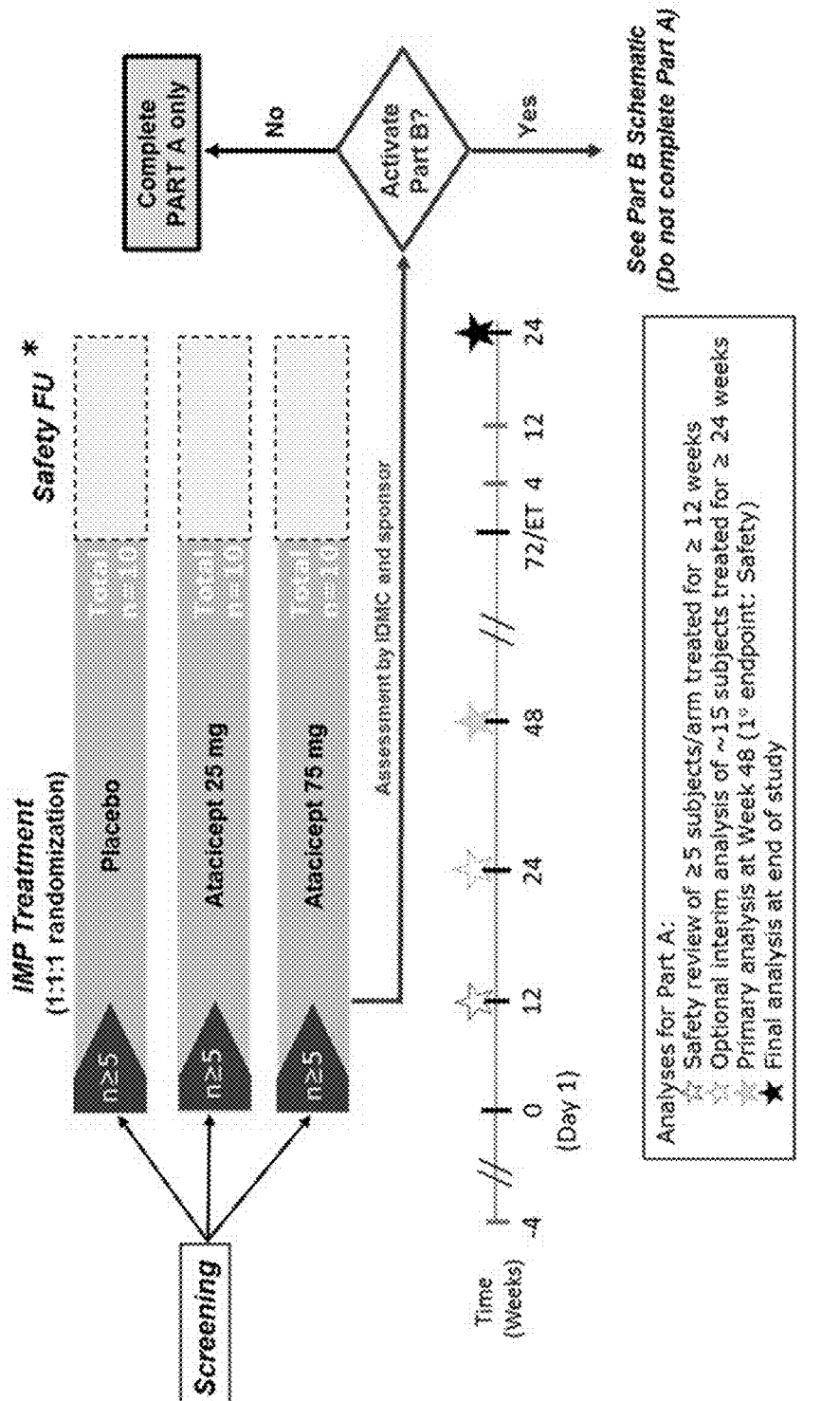
FIG. 1 is a schematic representation of the study design (Part A) of Example 1. *: Subjects who have early termination prior to week 72 undergo an early termination visit and a safety follow-up period with visits at weeks 4, 12, 24, and every 12 weeks thereafter, until week 72. ET: early termination visit; IMP: investigational medicinal product; Safety FU: 24-week safety follow-up period.

Although the present disclosure is described in detail above and below, it is to be understood that this disclosure is not limited to the particular methodologies, protocols and reagents described by the present disclosure, as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

In the following, certain elements of the present disclosure will be described in more detail, including the description of specific embodiments. However, the variously described examples and preferred embodiments should not be construed to limit the present disclosure to only the explicitly described embodiments. This description should be understood to support and encompass embodiments which combine the explicitly described embodiments with any number of the disclosed and/or preferred elements and in any manner. Furthermore, any permutations and combinations of all described elements in this application should be considered disclosed by the description of the present application except for where this leads to logical contradictions or the context indicates otherwise.

Unless defined otherwise herein, scientific and technical terms used in connection with the present disclosure shall have the meanings that are commonly understood by those of ordinary skill in the art. Generally, nomenclatures and techniques referred to in the present disclosure, e.g. nomenclatures and techniques of medicine, pharmacy, biology, biotechnology, pharmacology or toxicology, are those well-known and commonly used in the art. The methods and techniques of the present disclosure are generally performed according to conventional methods well-known in the art and as described in the references cited and discussed throughout the present disclosure unless otherwise indicated.

If the present disclosure states that a patent application, patents or printed publications cited herein is incorporated herein by reference in its entirety, such incorporated material is incorporated in its entirety except for any claims, definitions, subject matter disclaimers or disavowals, and except to the extent that the incorporated material is inconsistent with the express disclosure herein, in which case the language in this disclosure controls.

According to one aspect, the present disclosure relates to a method for treating a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

According to another aspect, the present disclosure relates to a method for reducing the serum Gd-IgA1 level in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

According to another aspect, the present disclosure relates to a method for reducing the proteinuria in a patient having IgA nephropathy, said method comprising administering to the patient a transmembrane activator and calcium modulator and cyclophilin ligand-interactor (TACI)-immunoglobulin (Ig) fusion molecule, wherein said TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

According to another aspect, the present disclosure relates to a method for reducing the serum Gd-IgA1 level and the proteinuria in a patient having IgA nephropathy, said method comprising administering to the patient a transmembrane activator and calcium modulator and cyclophilin ligand-interactor (TACI)-immunoglobulin (Ig) fusion molecule, wherein said TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

According to another aspect, the present disclosure relates to a method of treating IgA nephropathy (IgAN) in a patient, said method comprising administering to the patient a transmembrane activator and calcium modulator and cyclophilin ligand-interactor (TACI)-immunoglobulin (Ig) fusion molecule, wherein said TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain,
and wherein said method comprises determining the level of proteinuria in said patient.

For the avoidance of doubt, the following description definitions and embodiments relate to each of the aspects described above, as well as each of the further aspects described below.

As used herein, "IgA nephropathy", abbreviated as "IgAN", refers to a kidney disease characterized by IgA1 deposits within the kidney (Selvaskandan H et al., 2019; Cattran D C et al., 2009; see also background section above). The most common histopathologic alteration associated with IgAN is focal or diffuse expansion of mesangial regions with proliferative cells and extracellular matrix. In addition, a wide variety of lesions identified by light microscopy may be seen in patients with more severe lesions, including diffuse endocapillary proliferation, segmental sclerosis, segmental necrosis, and cellular crescent formation. Different prognosis is found in patients with IgA nephropathy. Several factors have been confirmed to highly correlated with an unfavorable prognosis of IgA nephropathy including hematuria, proteinuria, high Gd-IgA1 levels in serum, moderate hypercellularity, glomerulosclerosis, tubulointerstitial inflammation, and a diffuse glomerular co-deposition of IgG and/or IgM as well as complement components 3 (C3).

Whether a patient with hematuria and/or proteinuria has IgA nephropathy can be verified by kidney biopsy. As the skilled person is aware, in individuals having IgA nephropathy, the biopsy specimen shows proliferation of the mesangium, with IgA deposits on immunofluorescence and electron microscopy. Preferably, according to the present disclosure an individual is considered as having IgA nephropathy/as being an IgA nephropathy patient if a combination of proteinuria and IgA-dominant mesangial deposits is observed in biopsy.

As the skilled person is aware, Gd-IgA1 is "galactose deficient IgA1", a modified form of immunoglobulin A1 that is aberrantly deposited in the glomerular mesangium of at least some IgAN patients, either alone or in combination with IgG and/or IgM. Publications related to Gd-IgA1 include Wyatt et al., N Engl J Med 2013; Czerkinsky et al. J Clin Invest (1986); Novak et al. Semin Nephrol 2008; Tomana et al. Kidney Int 1997; and Suzuki et al., Clin Exp Nephrol 2014.

The serum Gd-IgA1 level can for example be determined by ELISA as described in Example 1 below, which follows the method disclosed by Suzuki and colleagues (Suzuki et al., Clin Exp Nephrol 2014). This method can also be carried out by commercial kits, e.g. the Gd-IgA1 (Galactose-deficient IgA1) Assay Kit by Immuno-Biological Laboratories, Japan (Catalog #27600) which is based on an ELISA with a monoclonal antibody that specifically recognizes the galactose-deficient hinge sequence of human Gd-IgA1 (Yamasaki et al., Monoclon Antib Immunodiagn Immunother, 2018; Yasutake et al., Nephrol Dial Transplant, 2015).

"Proteinuria", as used herein, refers to the presence of protein in the urine in excess of normal levels. "Proteinuria" includes "albuminuria" and "microalbuminuria". Normal human levels of protein appear in the urine in the range of about 0 to 30 mg/L, although for a random urine sample, the level may reach about 80 mg/L. For a 24 hour urine collection, normal human levels of urinary protein are in the range of about 0 to 150 mg. Preferably, according to the present disclosure a test for proteinuria is considered as indicating an abnormal or elevated protein level (and thus the test for proteinuria is "positive" in the sense that the patient is identified as having proteinuria) if the patient has >0.5 g of protein per day in the urine or >0.5 mg/mg urine protein:creatinine ratio (UPCR) in the 24 h-urine.

As used herein, a patient has "persistent proteinuria" if he/she has had at least two consecutive positive tests for proteinuria in a row. In this context, a test may for example be considered positive if the patient has >0.5 g of protein per day in the urine or >0.5 mg/mg urine protein:creatinine ratio (UPCR) in the 24 h-urine. As a skilled person will be aware, to be meaningful the second tests should not be carried out immediately after the first, but in some temporal distance, e.g. after a week or a few months (e.g. with a time of 1 week to 6 months between the two positive tests). Persistent proteinuria illustrates a chronic kidney disease and most often the point of no return. Therefore, persistent proteinuria is risk factor of further progression towards severe disease with renal failure and either death or chronic dialysis as consequences.

The severity of a proteinuria can further be described by the "UPCR" (urine protein:creatinine ratio) value. Creatinine is normally released into the urine at a roughly constant rate. Thus, the UPCR allows to estimate if the daily protein excretion in urine is increased compared to a normal/healthy state (Yang et al., PLoS ONE, 2015). The normal urine protein/creatinine ratio is not more than 200 mg/g. Preferably, according to the present disclosure the UPCR is determined by measuring the total protein and the creatinine in the 24-hour urine.

If the present disclosure refers to "determining the level of proteinuria", this means the combination of (1) determining if the patient has proteinuria, (2) determining if the proteinuria is a persistent proteinuria, and (3) determining the UPCR (urine protein:creatinine ratio) value based on 24-hour urine collection.

As used herein, "treating" a disease and "treatment" of a disease refers to the process of providing a subject with a pharmaceutical treatment, e.g., the administration of a drug, such that said disease is alleviated, reduced, minimized, halted or even healed, and/or such that the chances of a relapse into the disease are reduced or a relapse into the disease is even prevented.

Typically, the patient subjected to the treatment/the administration according to the present disclosure has previously been treated with standard of care (SOC) therapy by administration of angiotensin converting enzyme inhibitor (ACEi) and/or angiotensin receptor blocker (ARB) therapy. For example, the patient may have been subjected to at least 8 weeks, preferably at least 12 weeks of treatment by administration of ACEi and/or ARB before subjecting the patient to a method of the present disclosure.

The method according to the present disclosure involves administration of a TACI-immunoglobulin (TACI-Ig) fusion molecule which comprises (i) a TACI extracellular domain or fragment thereof which binds BLyS (B Lymphocyte Stimulator) and APRIL (A Proliferation-Inducing Ligand); and (ii) a human immunoglobulin-constant domain.

To date, three receptors have been identified that have unique binding affinities for the two growth factors BLyS (B Lymphocyte Stimulator) and APRIL (A Proliferation-Inducing Ligand): TACI (transmembrane activator and CAML-interactor, also known as also known as tumor necrosis factor receptor superfamily member 13B (TNFRSF13B)), BCMA (B-cell maturation antigen) and BAFF-R (receptor for B-cell activating factor) (Marsters et al. 2000; Thompson et al. 2001).

TACI and BCMA bind both BLyS and APRIL, while BAFF-R appears capable of binding only BLyS with high affinity (Marsters et al., 2000; Thompson et al. 2001). As a result, BLyS is able to signal through all three receptors, while APRIL only appears capable of signaling through TACI and BCMA. In addition, circulating heterotrimeric complexes of BLyS and APRIL (groupings of three protein subunits, containing one or two copies each of BLyS and APRIL subunits) have been identified in serum samples taken from patients with systemic immune-based rheumatic diseases, and have been shown to induce B-cell proliferation in vitro (Raschke et al., 2002).

BLyS and APRIL are potent stimulators of B-cell maturation, proliferation and survival (Moore et al., 1999; Schneider et al., 1999; Do et al., 2000) and play a role in the persistence of autoimmune diseases, especially those involving B-cells. Atacicept, an antagonist for all known conformations of BLyS and APRIL (i.e., homotrimeric, heterotrimeric, multimeric, and soluble or membrane-expressed), deprives B cells of essential survival signals (Gross J A et al., 2001).

Unless indicated otherwise, if the present disclosure refers to "TACI", this is meant to refer to the human TACI receptor. The amino acid sequence of TACI is provided as SEQ ID NO: 10 of this disclosure.

The term "TACI extracellular domain" designates the extracellular domain of (human) TACI. The extracellular domain of TACI corresponds to amino acids 1-166 of SEQ ID NO: 10. The amino acid sequence of the extracellular domain of TACI is provided as SEQ ID NO: 11 of this disclosure.

Whether a TACI extracellular domain or fragment thereof binds to BLyS can be determined by methods known to the skilled person and described e.g. in Example 4 of published US Patent Application No. US 2003/0103986 A1.

It is understood by the person skilled in the art that a TACI-Ig fusion molecule in accordance with the present disclosure is not an anti-TACI antibody. An anti-TACI antibody would not comprise the TACI extracellular domain or a variant or fragment thereof which binds to BLyS and/or APRIL, but would be directed against an epitope from the TACI extracellular domain.

The published US patent application US 2006/0067933 A1 (which is herewith incorporated by reference in its entirety) and the international application PCT/US02/15910 (published as WO 02/094852 A2, herewith incorporated by reference in its entirety) disclose sequences for the extracellular domain of TACI as well as specific fragments of the TACI extracellular domain that interact with its ligands, BLyS and APRIL.

As disclosed e.g. in US 2006/0067933 A1, the TACI extracellular domain comprises two cysteine (Cys)-rich repeats which are characteristic for members of the tumor necrosis factor (TNF) receptor superfamily, to which the TACI receptor belongs. In US 2006/0067933 A1, it has also been established that a splice variant of TACI, designated BR42x2, comprising only the second, less conserved Cys-rich repeat, was able to bind to BLyS. Therefore, in the frame of the present disclosure, the TACI extracellular domain or fragment thereof preferably at least comprises or consists of amino acid residues 71 to 104 of SEQ ID NO: 11 corresponding to the second Cys-rich repeat. Alternatively, the TACI extracellular domain or fragment thereof may further comprise amino acid residues 34 to 66 of SEQ ID NO: 11, corresponding to the first Cys-rich repeat. In a preferred embodiment of the present disclosure, said TACI extracellular domain or fragment thereof comprises or consists of amino acid residues 30 to 110 of SEQ ID NO: 11. A TACI-Ig fusion molecule comprising this sequence binds to and inhibits BLyS. Moreover, a TACI-Ig fusion molecule comprising this sequence also binds to and inhibits APRIL.

Fragments and variants (e.g. sequence variants of different % of identity) of the TACI extracellular domain can be used in the context of the present invention as well, as long as the fragment/variant is able to bind BLyS and/or APRIL. Preferably, such a fragment also inhibits or reduces the biological activity of BLyS and/or APRIL.

The ability of any TACI extracellular domain, TAC1-Ig fusion molecule, or any variant or fragment thereof to bind BLyS and/or APRIL can be assessed by standard binding assays known to a skilled person.

For example, a competitive binding assay can be carried out as described in Example 4A of published US Patent Application No. US 2003/0103986 A1 (which is herewith incorporated by reference in its entirety). Briefly, TACI can be coated to a 96 well-plate. Radiolabelled BLyS or APRIL is prepared. Mixtures of the TACI-Ig fusion molecule to be tested, at various concentrations, with a fixed concentration of radiolabelled BLyS or APRIL is exposed to the TACI-coated plate. $IC_{50}$ values can be calculated based on the amount of retained radiolabel.

Alternatively, a solution binding assay can be carried out as described in Example 4B of published US Patent Application No. US 2003/0103986 A1.

The ability to inhibit or reduce BLyS or APRIL biological activity can be assessed by standard activity assays known to a skilled person, for example by verifying if the TACI extracellular domain or TAC1-Ig fusion molecule to be tested has the ability to cause a dose-dependent reduction in immunoglobulin levels and in mature and total B cells. Such experiments are described for example in Example 11 of published US Patent Application US 2006/0067933 A1.

The term "human immunoglobulin constant domain", as used herein, is also called "immunoglobulin (Ig)-constant domain" or an "Fc domain" and is derived from a human that is preferably an IgG. The IgG may be an IgG1, IgG2, IgG3 or IgG4. The Fc domain preferably comprises at least the CH2, CH3 domain of IgG1, preferably together with the hinge region. Preferably, the human immunoglobulin constant domain is a human IgG1 constant domain.

In some embodiments, said human IgG1 constant domain has been modified for reduced complement-dependent cytotoxicity (CDC) and/or antibody-dependent cellular cytotoxicity (ADCC).

In ADCC, the Fc domain of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface. The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Two regions of the CH2 domain are important for FcγRs and complement C1q binding, and have unique sequences in IgG2 and IgG4. For instance, substitution of IgG2 residues at positions 233-236 into human IgG1 has been reported to greatly reduce ADCC and CDC. The following Fc mutations, according to EU index positions (Kabat et al., 1991), can e.g. be introduced into an Fc derived from IgG1:

T250Q/M428L
M252Y/S254T/T256E+H433K/N434F
E233P/L234V/L235A/AG236+A327G/A330S/P331S
E333A; K322A.

Further Fc mutations may e.g. be the substitutions at EU index positions selected from 330, 331 234, or 235, or combinations thereof. An amino acid substitution at EU index position 297 located in the CH2 domain may also be introduced into the Fc domain in the context of the present invention, eliminating a potential site of N-linked carbohydrate attachment. The cysteine residue at EU index position 220 may also be replaced with a serine residue, eliminating the cysteine residue that normally forms disulfide bonds with the immunoglobulin light chain constant region.

Particular Fc domains suitable for TACI-Ig fusion proteins (Fc-488, as well as Fc4, Fc5, Fc6, Fc7, and Fc8) and their preparation are for example disclosed in U.S. Pat. No. 8,637,021. A preferred example for a human immunoglobulin constant domain that may be used in the TACI-Ig fusion molecule of the present disclosure is provided by SEQ ID NO: 2. The use of any of these specific Fc domains or sequence variants thereof for formation of an TAC1-1g fusion protein is within the scope of the present disclosure.

A "fusion molecule" according to the present disclosure is a molecule comprising the two parts defined above (i.e. (i) a TACI extracellular domain or fragment thereof which binds BLyS and/or APRIL; and (ii) a human immunoglobulin-constant domain). Such a fusion molecule may be a hybrid protein expressed by a nucleic acid molecule comprising nucleotide sequences of at least two genes. For example, a TACI-immunoglobulin fusion molecule can comprise a TACI receptor moiety and an immunoglobulin moiety. As used herein, a "TACI receptor moiety" is a portion of the extracellular domain of the TACI receptor that binds at least one of BLyS or APRIL.

The term "receptor" denotes a cell-associated protein that binds to a bioactive molecule termed a "ligand." This interaction mediates the effect of the ligand on the cell. In the context of TACI receptor binding, the phrase "specifically binds" or "specific binding" refers to the ability of the ligand to competitively bind with the receptor. For example, BLyS specifically binds with the TACI receptor, and this can be shown by observing competition for the TACI receptor between detectably labeled BLyS and unlabeled BLyS.

Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

If the present disclosure states that a TACI extracellular domain or fragment thereof "binds" BLyS and/or APRIL, this means that said TACI extracellular domain or fragment thereof binds competitively with the TACI receptor to BLyS and/or APRIL. This binding can be verified by competitive binding experiments as known to a skilled person. For example, to verify binding of a TACI extracellular domain or fragment thereof to BLyS, a fixed amount of labelled BLyS (e.g. with a radiolabel) can be bound to a fixed amount of immobilized full-length TACI receptor in the presence of different amounts of said TACI extracellular domain or fragment thereof. If in the presence of increasing amounts of the TACI extracellular domain or fragment thereof the amount of labelled BLyS bound to said immobilized TACI receptor is decreased, this indicates that said TACI extracellular domain or fragment thereof binds competitively with the TACI receptor to BLyS. Binding of said TACI extracellular domain or fragment thereof to APRIL can be verified by corresponding experiments with labelled APRIL.

Examples for TACI-Ig fusion molecules are atacicept (WHO Drug Information, Vol. 21 (2007) No. 1, p. 58) or the closely related molecule telitacicept (WHO Drug Information, Vol. 33 (2019), No. 3, p. 689).

The amino acid sequence of atacicept is provided as SEQ ID NO: 3. The amino acid sequence of the closely related TACI-Ig fusion molecule telitacicept is provided as SEQ ID NO: 4. The amino acid sequence of further closely related TACI-Ig fusion molecules disclosed in published European patent application EP 2161287 A1 are provided as SEQ ID NO: 5-7 and 9. The amino acid sequence of a further closely related TACI-Ig fusion molecules disclosed in U.S. Pat. No. 8,193,316 B2 is provided as SEQ ID NO: 8.

Atacicept is a recombinant fusion protein containing the extracellular, ligand-binding portion of the receptor TACI (Transmembrane activator and calcium modulator and cyclophilin-ligand (CAML)-interactor) and the modified Fc portion of human IgG.

Atacicept acts as an antagonist to BLyS (B-lymphocyte stimulator) and APRIL (A proliferation-inducing ligand), both members of the tumor necrosis factor (TNF) superfamily. BLyS and APRIL have been shown to be important regulators of B cell maturation function and survival.

Atacicept is a soluble glycoprotein containing 313 amino acids, resulting from the fusion of a human IgG1-Fc and a portion from the extracellular domain of the BLyS receptor TACI, with a predicted mass of 35.4 kilodalton (kDa). The product conformation is dimeric, with a predicted mass of 73.4 kDa. Atacicept is produced in Chinese Hamster Ovary (CHO) cells by recombinant technology.

In atacicept, the human IgG1-Fc was modified to reduce Fc binding to the C1q component of complement and the interaction with antibody receptors (Tao et al., 1993; Canfield et al., 1991). Atacicept was tested and confirmed for reduction of these Fc effector functions.

It is preferred, in the context of the present invention, that any such fragment or variant of a TACI extracellular domain or a TACI-Ig fusion molecule, does not have any biological activity which is significantly lower than that of atacicept, i.e. a protein having the amino acid sequence of SEQ ID NO: 3.

The TACI-Ig molecule may be prepared by standard methods of molecular biology, recombinant protein expression and purification known to the skilled person. Such methods are for example described in US Published Patent Application No. US 2003/0103986 A1. Specifically, a nucleic acid encoding the protein sequence of the TACI-Ig fusion molecule can be prepared, either by DNA synthesis or by a method as described in Example 1 of US 2003/0103986 A1. Subsequently, this nucleic acid can be cloned into a mammalian expression vector, as described in Example 2 of US 2003/0103986 A1. The expression construct can then be used to transfect mammalian expression cells, e.g. Chinese hamster ovary (CHO) DG44 cells, and to recombinantly express the TACI-Ig fusion molecule encoded the expression construct, as described in Example 2 of US 2003/0103986 A1. The recombinantly expressed protein can then be isolated and purified e.g. by a combination of protein A affinity chromatography and S-200 size exclusion chromatography, as described in Example 2 and 3 of US 2003/0103986 A1. Structural characterization of the purified TACI-Ig fusion molecule may be carried out by Western blotting and protein sequencing as described in Example 3 of US 2003/0103986 A1. Moreover, a functional characterization of the TACI-Ig fusion molecule can be carried out by competitive binding assays or solution binding assays as described in Example 4 of US 2003/0103986 A1.

To achieve the effects described in the present disclosure (e.g. effects of reducing the Gd-IgA1 serum concentration and/or the proteinuria), the TACI-Ig fusion molecule is administered to a patient in a therapeutically effective amount. Thus, if the present disclosure states that the TACI-Ig fusion molecule is administered to a patient/subject in need thereof, it is understood that this means that a thera- peutically effective amount of said TACI-Ig fusion molecule is administered. A TACI-immunoglobulin protein and a pharmaceutically acceptable carrier is said to be adminis- tered in a "therapeutically effective amount" if the amount administered is physiologically significant. An agent is physiologically significant if its presence results in a detect- able change in the physiology of a recipient patient. One example of a general indication that a TACI-immunoglobu- lin protein is administered in a therapeutically effective amount is that, following administration to a subject, there is a decrease in circulating levels of BLyS and/or APRIL in the blood. The level of circulating levels of BLyS and/or APRIL in the blood can for example be determined by an ELISA. Examples for concentrations considered a therapeu- tically effective are provided e.g. in Example 1 (25 mg per week or 75 mg per week).

The formulation, dosage form and route of administration of the TACI-Ig fusion molecule is not particularly limited, as long as it results in an appropriate serum concentration of the TACI-Ig fusion molecule (see Example 1 and FIG. 5A for examples) that allows for the desired effects.

Generally, the dosage of administered TACI-immuno- globulin protein will vary depending upon such factors as the subject's age, weight, height, sex, general medical condition and previous medical history. Typically, it is desirable to provide the recipient with a dosage of TACI- immunoglobulin protein, which is in the range of from about 0.2 to 10 mg of TACI-Ig fusion molecule per kg of body weight of said subject, although a lower or higher dosage also may be administered as circumstances dictate. For example, 25 mg or 75 mg of said TACI-Ig fusion molecule may be administered to a subject per week in one dose per week (or split up into several doses administered over the week). In particular, higher concentrations, such as 100 mg, 125 mg or 150 mg of said TACI-Ig fusion molecule admin- istered to a subject per week in one dose per week (or split up into several doses administered over the week) may also be considered.

Administration of a TACI-immunoglobulin protein to a subject can be intravenous, intraarterial, intraperitoneal, intramuscular, subcutaneous, intrapleural, intrathecal, by perfusion through a regional catheter, or by direct intral- esional injection. When administering therapeutic proteins by injection, the administration may be by continuous infu- sion or by single or multiple boluses.

Additional routes of administration include oral, mucosal- membrane, pulmonary, and transcutaneous. Oral delivery is suitable for polyester microspheres, zein microspheres, pro- teinoid microspheres, polycyanoacrylate microspheres, and lipid-based systems (see, for example, DiBase and Morrel, "Oral Delivery of Microencapsulated Proteins," in Protein Delivery: Physical Systems, Sanders and Hendren (eds.), pages 255-288 (Plenum Press 1997)). The feasibility of an intranasal delivery is exemplified by such a mode of insulin administration (see, for example, Hinchcliffe and Illum, Adv. Drug Deliv. Rev. 35:199 (1999)). Dry or liquid par- ticles comprising TACI-immunoglobulin can be prepared and inhaled with the aid of dry-powder dispersers, liquid aerosol generators, or nebulizers (e.g., Pettit and Gombotz, TIBTECH 16:343 (1998); Patton et al., Adv. Drug Deliv. Rev. 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concen- trations with the aid of low-frequency ultrasound, which illustrates the feasibility of transcutaneous administration (Mitragotri et al., Science 269:850 (1995)). Transdermal delivery using electroporation provides another means to administer a TACI-immunoglobulin protein (Potts et al., Phann. Biotechnol. 10:213 (1997)).

A pharmaceutical composition comprising a TACI-immu- noglobulin protein can be formulated according to known methods to prepare pharmaceutically useful compositions, whereby the therapeutic proteins are combined in a mixture with a pharmaceutically acceptable carrier. The term "phar- maceutically acceptable" designates that said carrier is a non-toxic, inert material that is compatible with the other ingredients of the pharmaceutical composition and not harmful to the patient that the pharmaceutical composition is administered to, such that it can be used in a pharmaceutical product. Substances suitable as carriers, diluents or excipi- ents in pharmaceutical compositions are known to a skilled person in the art (Remington: The Science and Practice of Pharmacy, 22nd ed. (2012), Pharmaceutical Press). Sterile phosphate-buffered saline is one example of a pharmaceu- tically acceptable carrier.

The pharmaceutical composition may further include e.g. additional adjuvants, antioxidants, buffering agents, bulking agents, colorants, emulsifiers, fillers, flavoring agents, pre- servatives, stabilizers, suspending agents and/or other cus- tomary pharmaceutical auxiliaries.

For example, the TACI-Ig fusion molecule (e.g. atacicept) can be formulated as described in U.S. Pat. No. 8,637,021 (U.S. Pat. No. 8,637,021 is herewith incorporated by refer- ence in its entirety).

The TACI-Ig fusion molecule (such as atacicept) can be administered in an aqueous solution containing, besides the TACI-Ig fusion molecule, (only) 60 to 100 mg/ml trehalose and an acetate buffer buffering the formulation at a pH ranging from 4.9-5.1 (see U.S. Pat. No. 8,637,021 B2 for details; see also Example 1 below). The TACI-Ig fusion molecule may be included in said aqueous solution for example at a concentration of 25 to 150 mg TACI-Ig fusion molecule per ml of said aqueous solution.

A pharmaceutical composition comprising a TACI-immu- noglobulin protein can be furnished in liquid form, in an aerosol, or in solid form. Liquid forms are illustrated by injectable solutions and oral suspensions. Exemplary solid forms include capsules, tablets, and controlled-release forms. The latter form is illustrated by miniosmotic pumps and implants (Bremer et al., Phann. Biotechnol. 10:239 (1997); Ranade, "Implants in Drug Delivery," in Drug Delivery Systems, Ranade and Hollinger (eds.), pages 95-123 (CRC Press 1995); Bremer et al., "Protein Delivery with Infusion Pumps," in Protein Delivery: Physical Sys- tems, Sanders and Hendren (eds.), pages 239-254 (Plenum Press 1997); Yewey et al., "Delivery of Proteins from a Controlled Release Injectable Implant," in Protein Delivery: Physical Systems, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see Ranade, "Site-Specific Drug Delivery Using Liposomes as Carriers," in Drug Delivery Systems, Ranade and Hollinger (eds.), pages 3-24 (CRC Press 1995)). A variety of agents can be encapsulated in liposomes: hydrophobic agents partition in the bilayers and hydrophilic agents partition within the inner aqueous space(s) (see, for example, Machy et al., Liposomes In Cell Biology And Pharmacology (John Libbey 1987), and Ostro et al., American J. Hosp. Phann. 46:1576 (1989)). Moreover, it is possible to control the therapeutic availability of the encapsulated agent by varying liposome size, the number of bilayers, lipid composition, as well as the charge and surface characteristics of the liposomes.

Other dosage forms can be devised by those skilled in the art, as shown, for example, by Ansel and Popovich, Pharmaceutical Dosage Forms and Drug Delivery Systems, 5th Edition (Lea & Febiger 1990), Gennaro (ed.), Remington's Pharmaceutical Sciences, 19th Edition (Mack Publishing Company 1995), and by Ranade and Hollinger, Drug Delivery Systems (CRC Press 1996).

As an illustration, pharmaceutical compositions may be supplied as a kit comprising a container that comprises a TACI-immunoglobulin protein. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the TACI-immunoglobulin protein composition is contraindicated in patients with known hypersensitivity to either the TACI receptor moiety or the immunoglobulin moiety.

In some embodiments of any one of the methods disclosed herein, said patient has persistent proteinuria.

In some embodiments,
(a) said persistent proteinuria is a persistent proteinuria with UPCR≥1 mg/mg based on 24-hour urine collection or
(b) said persistent proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

In some embodiments, said persistent proteinuria is a persistent proteinuria with UPCR≥0.75 mg/mg based on 24-hour urine collection.

In some embodiments, said persistent proteinuria is a persistent proteinuria with UPCR≥1 mg/mg based on 24-hour urine collection.

In some embodiments,
(a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy or
(b) said persistent proteinuria is a persistent proteinuria with UPCR≥0.75 mg/mg based on 24-hour urine collection, as determined with said patient being on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said persistent proteinuria is a persistent proteinuria with UPCR≥0.75 mg/mg based on 24-hour urine collection, as determined with said patient being on angiotensin converting enzyme inhibitor (ACEi) and/or angiotensin receptor blocker (ARB) therapy.

In some embodiments, said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy.

In some embodiments, said patient has had said persistent proteinuria for at least 8 weeks prior to said administration or said use of said TACI-Ig fusion molecule.

According to another aspect, the present disclosure relates to a method for treating IgA nephropathy (IgAN) in a patient, said method comprising the steps of
(1) measuring the protein level in the urine of said patient; and
(2) administering to said patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

According to another aspect, the present disclosure relates to a method of treating IgA nephropathy (IgAN) in a patient, said method comprising the steps of
(1) administering to said patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain;
(2) measuring the protein level in the urine of said patient; and
(3) continuing to administer said TACI-Ig fusion molecule to said patient if said patient has proteinuria.

According to another aspect, the present disclosure relates to a method of treating IgA nephropathy (IgAN) in a patient, said method comprising the steps of
(1) administering to said patient an angiotensin converting enzyme inhibitor (ACEi) and/or an angiotensin receptor blocker (ARB);
(2) measuring the protein level in the urine of said patient; and
(3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

If the present disclosure refers to a step of "measuring the protein level in the urine" of a patient, this means a step in which either the total protein in the urine of said patient or the UPCR in the urine of said patient is determined, for example based on the 24 hour urine. Preferably, the term refers to a step in which the total protein in the 24-hour urine of said patient is determined. The protein level in the urine of a patient can be measured by standard methods of clinical practice. It is understood that this measurement should be carried out in such a manner that it allows to determine if the patient suffers from proteinuria. In a particularly preferred embodiment, the term involves measurements to (1) determine if the patient has proteinuria, (2) determine if the proteinuria is a persistent proteinuria, and (3) determine the UPCR (urine protein:creatinine ratio) value based on 24-hour urine collection.

The following embodiments relate to each of the three preceding aspects of the present disclosure.

In some embodiments, said measuring step further comprises determining that said patient has persistent proteinuria.

In some embodiments, said measuring step further comprises (a) determining that said patient has a persistent proteinuria with UPCR≥1 mg/mg based on 24-hour urine collection or (b) determining that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

In some embodiments, said measuring step further comprises determining that said patient has a persistent proteinuria with UPCR≥0.75 mg/mg based on 24-hour urine collection.

In some embodiments, said measuring step further comprises determining that said patient has a persistent proteinuria with UPCR≥1 mg/mg based on 24-hour urine collection.

In some embodiments, said measuring step further comprises (a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or (b) determining that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

In some embodiments, said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

In some embodiments, said measuring step further comprises determining that said patient has had said persistent proteinuria for at least 8 weeks prior to said administration or said use of said TACI-Ig fusion molecule.

In some embodiments, said measuring step (2) further comprises deciding, based on the measurement in step (2), whether step (3) is to be carried out.

In some embodiments, said step (3) is to be carried out only if the measuring step shows that said patient has persistent proteinuria.

In some embodiments, said step (3) is to be carried out only if (a) the measuring step shows that said patient has a persistent proteinuria with UPCR≥1 mg/mg based on 24-hour urine collection or (b) the measuring step shows that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

In some embodiments, said step (3) is to be carried out only if the measuring step shows that said patient has a persistent proteinuria with UPCR≥0.75 mg/mg based on 24-hour urine collection.

In some embodiments, said step (3) is to be carried out only if the measuring step shows that said patient has a persistent proteinuria with UPCR≥1 mg/mg based on 24-hour urine collection.

In some embodiments, said step (3) is to be carried out only if (a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or (b) the measuring step shows that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

In some embodiments, said step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

In some embodiments, said step (3) is to be carried out only if the measuring step shows that said patient has had said persistent proteinuria for at least 8 weeks prior to said administration or said use of said TACI-Ig fusion molecule.

For the avoidance of doubt, the following description definitions and embodiments relate to each of the aspects described above, as well as each of the further aspects described below.

In some embodiments, said TACI extracellular domain or fragment thereof binds BLyS (B Lymphocyte Stimulator). For example, atacicept comprises a fragment of the TACI extracellular domain that binds BLyS. Hence, atacicept binds BLyS.

In some embodiments, said TACI extracellular domain or fragment thereof binds APRIL (A Proliferation-Inducing Ligand). For example, atacicept comprises a fragment of the TACI extracellular domain that binds APRIL. Hence, atacicept binds APRIL.

In some embodiments, said TACI extracellular domain or fragment thereof binds BLyS (B Lymphocyte Stimulator) and APRIL (A Proliferation-Inducing Ligand). For example, atacicept comprises a fragment of the TACI extracellular domain that binds BLyS and APRIL. Hence, atacicept binds BLyS and APRIL.

In some embodiments, binding of said TACI-Ig fusion molecule via said TACI extracellular domain or fragment thereof to BLyS inhibits binding of BLyS to the endogenous TACI receptor on B cells. Whether a TACI-Ig fusion molecule inhibits binding of BLyS to the endogenous TACI receptor on B cells can for example be determined by competitive binding experiments with cultured B cells, labelled BLyS and increasing amounts of said TACI-Ig fusion molecule resp. of the part of said TACI-Ig fusion molecule corresponding to the TACI extracellular domain or a fragment thereof. If increasing amounts of said TACI-Ig fusion molecule resp. of the part of said TACI-Ig fusion molecule corresponding to the TACI extracellular domain or a fragment thereof competitively replace the labelled BLyS from its binding to the B cells (i.e. to the TACI receptor on B cells), this indicates that said TACI-Ig fusion molecule inhibits binding of BLyS to the endogenous TACI receptor on B cells. For example, atacicept comprises a fragment of the TACI extracellular domain that binds BLyS and inhibits binding of BLyS to the endogenous TACI receptor on B cells.

In some embodiments, binding of said TACI-Ig fusion molecule via said TACI extracellular domain or fragment thereof to APRIL inhibits binding of APRIL to the endogenous TACI receptor on B cells. Whether a TACI-Ig fusion molecule inhibits binding of APRIL to the endogenous TACI receptor on B cells can for example be determined by competitive binding experiments as described above for BLyS. For example, atacicept comprises a fragment of the TACI extracellular domain that binds APRIL and inhibits binding of APRIL to the endogenous TACI receptor on B cells.

In some embodiments, said TACI-Ig fusion molecule consists of amino acids.

In some embodiments, said TACI extracellular domain or fragment thereof comprises at least 60, preferably at least 70 more preferably at least 80 amino acids.

In some embodiments, said human immunoglobulin-constant domain comprises at least 200 amino acids, preferably at least 210 amino acids, more preferably at least 220 amino acids, even more preferably at least 230 amino acids.

In some embodiments, said TACI-Ig fusion molecule consists of (i) a TACI extracellular domain or fragment thereof which binds BLyS (B Lymphocyte Stimulator) and/or APRIL (A Proliferation-Inducing Ligand) linked by a peptide bond to (ii) a human immunoglobulin-constant domain.

In some embodiments, said TACI extracellular domain or fragment thereof has an amino acid sequence that is at least 80%, preferably at least 90%, more preferably at least 95% identical to SEQ ID NO: 1. Even more preferably, said TACI extracellular domain or fragment thereof has an amino acid sequence comprising SEQ ID NO: 1. Even more preferably, said TACI extracellular domain or fragment thereof has an amino acid sequence consisting of SEQ ID NO: 1.

If the present disclosure states that a certain sequence A "is at least x % identical" to another sequence B, this is synonymous to the statement that sequence A "has x % identity" to sequence B. The statement reflects a relationship between the two polypeptide sequences A and B determined by comparing the sequences. In general, identity refers to an exact amino acid to amino acid correspondence of the two polypeptide sequences, respectively, over the length of the sequences being compared. For sequences where there is not an exact correspondence, a percentage to which the two sequences are identical may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity between two polypeptide sequences. BESTFIT uses the "local homology" algorithm of Smith and Waterman (1981) and finds the best single region of similarity between two sequences. Other programs for determining identity sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990). Preferably, % identity according to the present disclosure is determined according to the BLAST family of programs (Altschul S F et al, 1990, Altschul S F et al, 1997, accessible through the home page of the NCBI at www.ncbi.nlm.nih-.gov).

In some embodiments, said human immunoglobulin-constant domain has an amino acid sequence that is at least 80%, preferably at least 90%, more preferably at least 95% identical to SEQ ID NO: 2. Even more preferably, said human immunoglobulin-constant domain has an amino acid sequence comprising SEQ ID NO: 2. Even more preferably, said human immunoglobulin-constant domain has an amino acid sequence consisting of SEQ ID NO: 2.

In some embodiments, said TACI-Ig fusion molecule has an amino acid sequence that is at least 80%, preferably at least 90%, more preferably at least 95% identical to SEQ ID NO: 3. Even more preferably, said human immunoglobulin-constant domain has an amino acid sequence comprising SEQ ID NO: 3. Even more preferably, said human immunoglobulin-constant domain has an amino acid sequence consisting of SEQ ID NO: 3.

In some embodiments, said TACI-Ig fusion molecule has an amino acid sequence that is at least 80%, preferably at least 90%, more preferably at least 95% identical to SEQ ID NO: 4. Even more preferably, said human immunoglobulin-constant domain has an amino acid sequence comprising SEQ ID NO: 4. Even more preferably, said human immunoglobulin-constant domain has an amino acid sequence consisting of SEQ ID NO: 4.

In some embodiments, said TACI-Ig fusion molecule has an amino acid sequence that is at least 80%, preferably at least 90%, more preferably at least 95% identical to at least one of SEQ ID NO: 5 to 9. Even more preferably, said TACI-Ig fusion molecule has an amino acid sequence comprising at least one of SEQ ID NO: 5 to 9. Even more preferably, said TACI-Ig fusion molecule has an amino acid sequence consisting of one of SEQ ID NO: 5 to 9.

In some embodiments, said TACI-Ig fusion molecule is atacicept or telitacicept.

In some embodiments, said TACI-Ig fusion molecule is telitacicept.

In a particularly preferred embodiments, said TACI-Ig fusion molecule is atacicept.

In some embodiments, said patient is a mammal.

In some embodiments, said patient is a human. Preferably, said human is at least 18 years old.

In some embodiments, said patient is of white or Asian race.

In some embodiments, said patient is of white race.

In some embodiments, said patient has proteinuria.

In some embodiments, said patient has been diagnosed to have proteinuria.

In some embodiments, said method comprises the step of determining whether said patient has proteinuria.

In some embodiments, said method comprises the step of determining whether said patient has proteinuria, and said patient is subjected to said treatment by administration of said TACI-Ig fusion molecule only if said patient has proteinuria.

In some embodiments, said proteinuria is a persistent proteinuria.

In some embodiments, said proteinuria is a proteinuria of at least 0.8 g/day, preferably at least 1.0 g/day, more preferably at least 1.3 g/day, even more preferably at least 1.5 g/day, even more preferably at least 2.0 g/day (total protein based on 24-hour urine collection).

As used herein, a "proteinuria of at least x g/day (total protein based on 24-hour urine collection)" means that in at least one measurement of the total protein based on 24-hour urine collection a value of at least x g has been measured.

In some embodiments, said proteinuria is a persistent proteinuria of at least 0.8 g/day, preferably at least 1.0 g/day, more preferably at least 1.3 g/day, even more preferably at least 1.5 g/day, even more preferably at least 2.0 g/day (total protein based on 24-hour urine collection).

As used herein, a "persistent proteinuria of at least x g/day (total protein based on 24-hour urine collection)" means that in at least in two consecutive measurements of the total protein based on 24-hour urine collection a value of at least x g has been measured. As a skilled person is aware, the two consecutive tests must occur with a temporal distance, e.g. a week or several months apart (e.g. with a temporal distance of at least 1 week up to 6 months).

In some embodiments, said proteinuria is a proteinuria of up to 6.0 g/day, preferably up to 5.0 g/day, more preferably up to 4.0 g/day (total protein based on 24-hour urine collection).

In some embodiments, said proteinuria is a proteinuria of 1.0 to 6.0 g/day, preferably 1.3 to 6.0 g/day (total protein based on 24-hour urine collection).

In some embodiments, said proteinuria is a persistent proteinuria of up to 6.0 g/day, preferably up to 5.0 g/day, more preferably up to 4.0 g/day (total protein based on 24-hour urine collection).

In some embodiments, said proteinuria is a persistent proteinuria of 1.0 to 6.0 g/day, preferably 1.3 to 6.0 g/day (total protein based on 24-hour urine collection).

In some embodiments, said proteinuria is characterized by a urine-protein creatinine ratio (UPCR), based on 24-hour urine collection, of at least 0.75 mg/mg, preferably at least 1.0 mg/mg, more preferably at least 1.5 mg/mg, more preferably at least 2.0 mg/mg.

In some embodiments, said proteinuria is characterized by a 24-hour urine-protein creatinine ratio (UPCR), based on 24-hour urine collection, of up to 6.0 mg/mg, preferably up to 5.0 mg/mg, more preferably up to 4.0 mg/mg.

In some embodiments, said proteinuria is characterized by a urine-protein creatinine ratio (UPCR), based on 24-hour urine collection, of 1.0 to 6.0 mg/mg, preferably 1.5 to 5.0 mg/mg, more preferably 1.5 to 4.0 mg/mg.

In some embodiments,
a) said proteinuria is a persistent proteinuria with UPCR≥1 mg/mg based on 24-hour urine collection; or
(b) said proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

In some embodiments, said proteinuria is a persistent proteinuria with UPCR≥0.75 mg/mg (preferably UPCR≥1 mg/mg) based on 24-hour urine collection.

In some embodiments,
a) said patient is on ACEi and/or ARB therapy and said proteinuria is a persistent proteinuria with UPCR≥1 mg/mg based on 24-hour urine collection; or
(b) said patient is on ACEi and/or ARB therapy and said proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said patient is on ACEi and/or ARB therapy and said proteinuria is a persistent proteinuria with UPCR≥0.75 mg/mg based on 24-hour urine collection.

In some embodiments, said patient is on ACEi and/or ARB therapy and said proteinuria is a persistent proteinuria with UPCR≥1 mg/mg based on 24-hour urine collection.

In some embodiments, said IgA nephropathy is an IgA nephropathy confirmed by kidney biopsy.

In some embodiments, said patient has been treated with an angiotensin converting enzyme (ACE) inhibitor and/or angiotensin receptor blocker (ARB) prior to said administration or said use of said TACI-Ig fusion molecule.

In some embodiments, said patient has been treated with an angiotensin converting enzyme (ACE) inhibitor and/or angiotensin receptor blocker (ARB) for at least 8 weeks (preferably for at least 12 weeks) prior to said administration or said use of said TACI-Ig fusion molecule.

In some embodiments, said patient has not been treated with immunosuppressant concomitant to said treatment with said angiotensin converting enzyme (ACE) inhibitor and/or angiotensin receptor blocker (ARB).

In some embodiments, said patient has been treated with an angiotensin converting enzyme (ACE) inhibitor and/or angiotensin receptor blocker (ARB) at stable dose for at least 8 weeks prior to said administration or said use of said TACI-Ig fusion molecule.

In some embodiments, an angiotensin converting enzyme (ACE) inhibitor and/or angiotensin receptor blocker (ARB) is administered as a background therapy to said patient simultaneously to said administration or said use of said TACI-Ig fusion molecule.

In some embodiments, said patient has an eGFR≥35 mL/min/1.73 m2.

In some embodiments, the serum IgG level of said patient is ≥6 g/L.

In some embodiments, said IgA nephropathy of said patient has not been treated with cyclophosphamide.

In some embodiments, said patient has an increased level of serum Gd-IgA1 compared to healthy individuals.

As the skilled person will be aware, if the present application states that a certain value, level or measurement e.g.

in a patient is higher/lower/increased/ . . . "compared to healthy individuals" or "compared to healthy individuals that do not have of IgAN", this is preferably verified by comparing the value, level of measurement with the average of corresponding values, levels or measurements obtained from a larger number of healthy individuals (e.g. 20, preferably >100 healthy individuals).

In some embodiments, said patient has a level of serum Gd-IgA1 that is increased by a least 25%, preferably 50%, more preferably 75% compared to healthy individuals.

In some embodiments, said patient has an increased BLyS level in serum compared to healthy individuals that do not have IgAN.

In some embodiments, said patient has been diagnosed to have an increased BLyS level in serum compared to healthy individuals that do not have IgAN.

In some embodiments, said method comprises the step of determining the level of the cytokine BLyS in the serum of said patient.

In some embodiments, said method comprises the step of determining the level of the cytokine BLyS in the serum of said patient, and said patient is subjected to the administration of said TACI-Ig fusion molecule only if said patient has an increased BLyS level in serum compared to healthy individuals that do not have IgAN.

In some embodiments, said increased BLyS level in serum is increased by at least 10%, preferably at least 25%, more preferably at least 50% compared to healthy individuals that do not have IgAN.

In some embodiments, said patient has an increased APRIL level in serum compared to healthy individuals that do not have IgAN.

In some embodiments, said patient has been diagnosed to have an increased APRIL level in serum compared to healthy individuals that do not have IgAN.

In some embodiments, said method comprises the step of determining the level of the cytokine APRIL in the serum of said patient.

In some embodiments, said method comprises the step of determining the level of the cytokine APRIL in the serum of said patient, and said patient is subjected to the administration of said TACI-Ig fusion molecule only if said patient has an increased APRIL level in serum compared to healthy individuals that do not have IgAN.

In some embodiments, said increased APRIL level in serum is increased by at least 10%, preferably at least 25%, more preferably at least 50% compared to healthy individuals that do not have IgAN.

In some embodiments, said patient has increased BLyS and APRIL levels compared to healthy individuals that do not have IgAN.

In some embodiments, said patient has been diagnosed to have increased BLyS and APRIL levels compared to healthy individuals that do not have IgAN.

In some embodiments, said method comprises the step of determining the levels of the cytokines BLyS and APRIL in the serum of said patient.

In some embodiments, said method comprises the step of determining the levels of the cytokines BLyS and APRIL in the serum of said patient, and said patient is subjected to the administration of said TACI-Ig fusion molecule if said patient has increased BLyS and APRIL levels compared to healthy individuals that do not have IgAN.

In some embodiments, said increased BLyS and APRIL level are each increased by at least 10%, preferably at least 25%, more preferably at least 50% compared to healthy individuals that do not have IgAN.

In some embodiments, said TACI-Ig fusion molecule is administered in an amount of 0.2 to 10 mg, preferably 0.5 to 5 mg, more preferably 0.5 to 2 mg, even more preferably 0.8 to 1.5 mg of TACI-Ig fusion molecule per kg of body weight of said patient per week.

In some embodiments, said TACI-Ig fusion molecule is administered in an amount of about 25 to about 150 mg per week, preferably about 50 to about 150 mg per week, more preferably about 75 to about 150 mg per week, even more preferably about 75 to about 125 mg per week, even more preferably about 75 mg per week.

In some embodiments, said TACI-Ig fusion molecule is administered in an amount of 25 to 150 mg per week, preferably 50 to 150 mg per week, more preferably 75 to 150 mg per week, even more preferably 75 mg per week.

In some embodiments, said TACI-Ig fusion molecule is administered in an amount of 75 to 125 mg per week.

In some embodiments, said TACI-Ig fusion molecule is administered in an amount of 70 to 155 mg per week, preferably 70 to 80 mg per week.

In some embodiments, said TACI-Ig fusion molecule is administered in one to three weekly doses, preferably in one or two weekly doses, more preferably in one weekly dose.

In some embodiments, said TACI-Ig fusion molecule is administered in one dose every other week.

In some embodiments, said TACI-Ig fusion molecule is administered for at least 4 weeks, preferably at least 8 weeks, more preferably at least 12 weeks, more preferably at least 24 weeks, more preferably at least 48 weeks, more preferably at least 52 weeks.

In some embodiments, said TACI-Ig fusion molecule is administered for up to 4 weeks, preferably up to 8 weeks, more preferably up to 12 weeks, even more preferably up to 24 weeks, even more preferably up to 48 weeks, even more preferably up to 52 weeks, even more preferably up to 72 weeks, even more preferably up to 156 weeks.

In some embodiments, said TACI-Ig fusion molecule is administered for 2 to 48 weeks.

In some embodiments, said TACI-Ig fusion molecule is administered for 2 to 52 weeks.

In some embodiments, said TACI-Ig fusion molecule is administered by subcutaneous administration.

In some embodiments, the TACI-Ig fusion molecule is administered in an aqueous solution containing (besides the TACI-Ig fusion molecule) 60 to 100 mg/ml trehalose and an acetate buffer buffering the formulation at a pH ranging from 4.9-5.1. In preferred embodiments, the TACI-Ig fusion molecule is administered in an aqueous solution containing (besides the TACI-Ig fusion molecule) only 60 to 100 mg/ml trehalose and an acetate buffer buffering the formulation at a pH ranging from 4.9-5.1. Preferably, said TACI-Ig fusion molecule is included in said aqueous solution at a concentration of 25 to 150 mg TACI-Ig fusion molecule per ml of said aqueous solution. More preferably, said TACI-Ig fusion molecule is included in said aqueous solution at a concentration of 25 or 75 mg TACI-Ig fusion molecule per ml of said aqueous solution. Even more preferably, said TACI-Ig fusion molecule is included in said aqueous solution at a concentration of 75 mg TACI-Ig fusion molecule per ml of said aqueous solution.

In some embodiments, said administration or said use of said TACI-Ig fusion molecule is by subcutaneous administration, wherein 25 mg of said TACI-Ig fusion molecule are administered per week in one dose per week.

In some embodiments, said administration or said use of said TACI-Ig fusion molecule is by subcutaneous administration, wherein 75 mg of said TACI-Ig fusion molecule are administered per week in one dose per week.

In some embodiments, concomitantly to said administration or said use of said TACI-Ig fusion molecule a further medicament is/further medicaments are administered to said patient.

In some embodiments, said further medicament is/said further medicaments are selected from the group consisting of an angiotensin converting enzyme (ACE) inhibitor, an angiotensin receptor blocker (ARB), aspirin, an antihypertensive medication (preferably selected from the group consisting of a diuretic, an aldosterone antagonist, a calcium-channel blocker and a β-blocker), a statin, omega-3 fish oil and dipyridamole.

In some embodiments, said further medicament(s) is an angiotensin converting enzyme (ACE) inhibitor or an angiotensin receptor blocker (ARB) and/or a combination of an angiotensin converting enzyme (ACE) inhibitor and an angiotensin receptor blocker (ARB).

In some embodiments, said further medicaments is a combination of an angiotensin converting enzyme (ACE) inhibitor and an angiotensin receptor blocker (ARB).

In some embodiments, said treatment/said administration or said use of said TACI-Ig fusion molecule results in a reduction in the total protein in the urine of said patient (based on 24-hour urine collection), preferably by at least 10%, more preferably at least 15%, even more preferably at least 20%, even more preferably at least 25%, compared to the situation before said treatment/said administration or said use of said TACI-Ig fusion molecule.

In some embodiments, said treatment/said administration or said use of said TACI-Ig fusion molecule results in a reduction in the urine-protein creatinine ratio (UPCR), based on 24-hour urine collection, preferably of at least 10%, more preferably at least 15%, even more preferably at least 20%, even more preferably at least 25%, even more preferably at least 30%, compared to the situation before said treatment/said administration or said use of said TACI-Ig fusion molecule.

In some embodiments, during said treatment/said administration or said use of said TACI-Ig fusion molecule the Estimated Glomerular Filtration Rate (eGFR) is decreased by not more than 10%, preferably not more than 5%.

As used herein, the "Estimated Glomerular Filtration Rate", abbreviated as "eGFR", is determined based on the CKD-EPI (Chronic Kidney Disease Epidemiology Collaboration) formula as known to a skilled person (see also Levey A S et al., 2009).

In some preferred embodiments, during said treatment/said administration or said use of said TACI-Ig fusion molecule the Estimated Glomerular Filtration Rate (eGFR) is not decreased.

In some embodiments, during said treatment/said administration or said use of said TACI-Ig fusion molecule the Estimated Glomerular Filtration Rate (eGFR) is increased, preferably by at least 5%, more preferably by at least 10%.

In some embodiments, said treatment/said administration or said use of said TACI-Ig fusion molecule results in a reduction in the number of mature naive B cells in peripheral blood, preferably by at least 10%, more preferably by at least 20%, even more preferably by at least 25%, even more preferably by at least 30%, even more preferably by at least 40%, even more preferably by at least 50%, compared to the situation before said treatment/said administration or said use of said TACI-Ig fusion molecule.

In some embodiments, said treatment/said administration or said use of said TACI-Ig fusion molecule results in a reduction in the serum level of Gd-IgA1 antibodies compared to the situation before said treatment/said administration or said use of said TACI-Ig fusion molecule, preferably by at least 10%, more preferably by at least 20%, even more preferably by at least 25%, even more preferably by at least 30%, even more preferably by at least 40%, even more preferably by at least 50%, even more preferably by at least 60%.

In some embodiments, said treatment/said administration or said use of said TACI-Ig fusion molecule results in a decrease in the serum concentration of IgA, preferably by at least 10%, more preferably by at least 20%, even more preferably by at least 30%, even more preferably by at least 40%, even more preferably by at least 50%, compared to the situation before said treatment/said administration or said use of said TACI-Ig fusion molecule.

In some embodiments, said treatment/said administration or said use of said TACI-Ig fusion molecule results in a decrease in the serum concentration of IgG, preferably by at least 10%, more preferably by at least 20%, even more preferably by at least 30%, compared to the situation before said treatment/said administration or said use of said TACI-Ig fusion molecule.

In some embodiments, said treatment/said administration or said use of said TACI-Ig fusion molecule results in a decrease in the serum concentration of IgM, preferably by at least 10%, more preferably by at least 20%, even more preferably by at least 30%, even more preferably by at least 40%, even more preferably by at least 50%, even more preferably by at least 60%, even more preferably by at least 70%, compared to the situation before said treatment/said administration or said use of said TACI-Ig fusion molecule.

In some embodiments, said treatment/said administration or said use of said TACI-Ig fusion molecule results in a decrease in the serum concentration of each of IgA, IgG, and IgM compared to the situation before said treatment/said administration or said use of said TACI-Ig fusion molecule, preferably by at least 10%, more preferably by at least 20%, even more preferably by at least 30%, compared to the situation before said treatment/said administration or said use of said TACI-Ig fusion molecule.

In some embodiments, said treatment/said administration or said use of said TACI-Ig fusion molecule results in a reduction in the serum level of anti-Gd-IgA1 antibodies compared to the situation before said treatment/said administration or said use of said TACI-Ig fusion molecule.

In some embodiments, said treatment/said administration or said use of said TACI-Ig fusion molecule results in a reduction in glomerular IgA deposition compared to the situation before said treatment/said administration or said use of said TACI-Ig fusion molecule.

In some embodiments, said treatment/said administration or said use of said TACI-Ig fusion molecule results in a reduction in glomerular IgA deposition compared to the situation before said treatment/said administration or said use of said TACI-Ig fusion molecule.

In some embodiments, said treatment/said administration or said use of said TACI-Ig fusion molecule results in a decrease in renal histopathology compared to the situation before said treatment/said administration or said use of said TACI-Ig fusion molecule.

In some embodiments, no decrease in the serum level of complement C3 is observed during said treatment/said administration or said use of said TACI-Ig fusion molecule.

In some embodiments, said treatment/said administration or said use of said TACI-Ig fusion molecule results in an increase in the serum level of complement C3 compared to the situation before said treatment/said administration or said use of said TACI-Ig fusion molecule.

In some embodiments, no decrease in the serum level of complement C4 is observed during said treatment/said administration or said use of said TACI-Ig fusion molecule.

In some embodiments, said treatment/said administration or said use of said TACI-Ig fusion molecule results in an increase in the serum level of complement C4 compared to the situation before said treatment/said administration or said use of said TACI-Ig fusion molecule.

According to another aspect, the present disclosure relates to a transmembrane activator and calcium modulator and cyclophilin ligand-interactor (TACI)-immunoglobulin (Ig) fusion molecule for use in the treatment of IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level and the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level and the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the serum Gd-IgA1 level in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig) fusion molecule for use in reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to a transmembrane activator and calcium modulator and cyclophilin ligand-interactor (TACI)-immunoglobulin (Ig)

fusion molecule for use in reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

For the avoidance of doubt, the following embodiments relate to each of the above-described aspects relating to a transmembrane activator and calcium modulator and cyclophilin ligand-interactor (TACI)-immunoglobulin (Ig) fusion molecule for use.

In some embodiments, said use comprises determining the level of proteinuria in said patient.

In some embodiments, said patient has proteinuria.

In some embodiments, said patient has been diagnosed as having proteinuria.

In some embodiments, said proteinuria is a persistent proteinuria.

In some embodiments, (a) said persistent proteinuria is a persistent proteinuria with UPCR≥1 mg/mg based on 24-hour urine collection or (b) said persistent proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

In some embodiments, said persistent proteinuria is a persistent proteinuria with UPCR≥0.75 mg/mg (preferably with UPCR≥1 mg/mg) based on 24-hour urine collection.

In some embodiments, (a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy, or (b) said persistent proteinuria is a persistent proteinuria with UPCR≥0.75 mg/mg based on 24-hour urine collection, as determined with said patient being on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said persistent proteinuria is a persistent proteinuria with UPCR≥0.75 mg/mg (preferably with UPCR≥1 mg/mg) based on 24-hour urine collection, as determined with said patient being on angiotensin converting enzyme inhibitor (ACEi) and/or angiotensin receptor blocker (ARB) therapy.

In some embodiments, said use comprises the steps of (1) measuring the protein level in the urine of said patient; and (2) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

In some embodiments, said use comprises the steps of (1) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

(2) measuring the protein level in the urine of said patient and (3) continuing to administer said TACI-Ig fusion molecule to said patient if said patient has proteinuria.

In some embodiments, said use comprises the steps of (1) administering to said patient an angiotensin converting enzyme inhibitor (ACEi) and/or an angiotensin receptor blocker (ARB);

(2) measuring the protein level in the urine of said patient; and (3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

In some embodiments, said measuring step further comprises determining that said patient has persistent proteinuria.

In some embodiments, said measuring step further comprises (a) determining that said patient has a persistent proteinuria with UPCR≥1 mg/mg based on 24-hour urine collection or (b) determining that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

In some embodiments, said measuring step further comprises determining that said patient has a persistent proteinuria with UPCR≥0.75 mg/mg, preferably with UPCR≥1 mg/mg, based on 24-hour urine collection.

In some embodiments, said measuring step further comprises (a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or (b) determining that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said measuring step further comprises determining that said patient has a persistent proteinuria with UPCR≥0.75 mg/mg (preferably with UPCR≥1 mg/mg) based on 24-hour urine collection while on angiotensin converting enzyme inhibitor (ACEi) and/or angiotensin receptor blocker (ARB) therapy.

In some embodiments, said measuring step further comprises determining that said patient has had said persistent proteinuria for at least 8 weeks prior to said administration or said use of said TACI-Ig fusion molecule.

In some embodiments, said measuring step (2) further comprises deciding, based on the measurement in step (2), whether step (3) is to be carried out.

In some embodiments, said step (3) is to be carried out only if the measuring step shows that said patient has persistent proteinuria.

In some embodiments, said step (3) is to be carried out only if (a) the measuring step shows that said patient has a persistent proteinuria with UPCR≥1 mg/mg based on 24-hour urine collection or (b) the measuring step shows that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

In some embodiments, said step (3) is to be carried out only if the measuring step shows that said patient has a persistent proteinuria with UPCR≥0.75 mg/mg based on 24-hour urine collection.

In some embodiments, said step (3) is to be carried out only if the measuring step shows that said patient has a persistent proteinuria with UPCR≥1 mg/mg based on 24-hour urine collection.

In some embodiments, said step (3) is to be carried out only if (a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or (b) the measuring step shows that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

In some embodiments, said step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

In some embodiments, said step (3) is to be carried out only if the measuring step shows that said patient has had said persistent proteinuria for at least 8 weeks prior to said administration or said use of said TACI-Ig fusion molecule.

For any of the above-described aspects relating to a transmembrane activator and calcium modulator and cyclophilin ligand-interactor (TACI)-immunoglobulin (Ig) fusion molecule for use and the embodiments relating thereto, said transmembrane activator and calcium modulator and cyclophilin ligand-interactor (TACI)-immunoglobulin (Ig) fusion molecule, said treatment, said IgA nephropathy, said patient, said administering, said TACI extracellular domain or fragment thereof, said BLyS and/or APRIL binding, said human immunoglobulin-constant domain, said reducing the serum Gd-IgA1 level, said Gd-IgA1, said reducing the proteinuria, said proteinuria, said determining the level of proteinuria in said patient, said diagnosis of proteinuria, said persistent proteinuria, said step of administering to said patient an angiotensin converting enzyme inhibitor (ACEi) and/or an angiotensin receptor blocker (ARB), said angiotensin converting enzyme inhibitor (ACEi) and/or angiotensin receptor blocker (ARB) therapy, said step of measuring the protein level in the urine of said patient, and said step of continuing to administer are as defined in any one of the embodiments disclosed above or any combination thereof.

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

According to another aspect, the present disclosure relates to the use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

For the avoidance of doubt, the following embodiments relate to each of the above-described aspects relating to the use of a transmembrane activator and calcium modulator and cyclophilin ligand-interactor (TACI)-immunoglobulin (Ig) fusion molecule for the manufacture of a medicament.

In some embodiments, said use comprises determining the level of proteinuria in said patient.

In some embodiments, said patient has proteinuria.

In some embodiments, said patient has been diagnosed to have proteinuria.

In some embodiments, said proteinuria is a persistent proteinuria.

In some embodiments, (a) said persistent proteinuria is a persistent proteinuria with UPCR≥1 mg/mg based on 24-hour urine collection or (b) said persistent proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

In some embodiments, said persistent proteinuria is a persistent proteinuria with UPCR≥0.75 mg/mg based on 24-hour urine collection.

In some embodiments, said persistent proteinuria is a persistent proteinuria with UPCR≥1 mg/mg based on 24-hour urine collection.

In some embodiments, (a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy or (b) said persistent proteinuria is a persistent proteinuria with UPCR≥0.75 mg/mg based on 24-hour urine collection, as determined with said patient being on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said use comprises the steps of (1) measuring the protein level in the urine of said patient; and (2) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

In some embodiments, said use comprises the steps of (1) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

(2) measuring the protein level in the urine of said patient and (3) continuing to administer said TACI-Ig fusion molecule to said patient if said patient has proteinuria.

In some embodiments, said use comprises the steps of (1) administering to said patient an angiotensin converting enzyme inhibitor (ACEi) and/or an angiotensin receptor blocker (ARB);

(2) measuring the protein level in the urine of said patient; and (3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

In some embodiments, said measuring step further comprises determining that said patient has persistent proteinuria.

In some embodiments, said measuring step further comprises (a) determining that said patient has a persistent proteinuria with UPCR≥1 mg/mg based on 24-hour urine collection or (b) determining that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

In some embodiments, said measuring step further comprises determining that said patient has a persistent proteinuria with UPCR≥0.75 mg/mg (preferably with UPCR≥1 mg/mg) based on 24-hour urine collection.

In some embodiments, said measuring step further comprises (a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or (b) determining that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said measuring step further comprises determining that said patient has a persistent proteinuria with UPCR≥0.75 mg/mg (preferable with UPCR≥1 mg/mg) based on 24-hour urine collection while on angiotensin converting enzyme inhibitor (ACEi) and/or angiotensin receptor blocker (ARB) therapy.

In some embodiments, said measuring step further comprises determining that said patient has had said persistent proteinuria for at least 8 weeks prior to said administration or said use of said TACI-Ig fusion molecule.

In some embodiments, said measuring step (2) further comprises deciding, based on the measurement in step (2), whether step (3) is to be carried out.

In some embodiments, said step (3) is to be carried out only if the measuring step shows that said patient has persistent proteinuria.

In some embodiments, said step (3) is to be carried out only if (a) the measuring step shows that said patient has a persistent proteinuria with UPCR≥1 mg/mg based on 24-hour urine collection or (b) the measuring step shows that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

In some embodiments, said step (3) is to be carried out only if the measuring step shows that said patient has a persistent proteinuria with UPCR≥0.75 mg/mg based on 24-hour urine collection.

In some embodiments, said step (3) is to be carried out only if the measuring step shows that said patient has a persistent proteinuria with UPCR≥1 mg/mg based on 24-hour urine collection.

In some embodiments, said step (3) is to be carried out only if (a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or (b) the measuring step shows that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

In some embodiments, said step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

In some embodiments, said step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

In some embodiments, said step (3) is to be carried out only if the measuring step shows that said patient has had said persistent proteinuria for at least 8 weeks prior to said administration or said use of said TACI-Ig fusion molecule.

For any of the above-described aspects relating to a transmembrane activator and calcium modulator and cyclophilin ligand-interactor (TACI)-immunoglobulin (Ig) fusion molecule for use and the embodiments relating thereto, said transmembrane activator and calcium modulator and cyclophilin ligand-interactor (TACI)-immunoglobulin (Ig) fusion molecule, said treatment, said IgA nephropathy, said patient, said administering, said TACI extracellular domain or fragment thereof, said BLyS and/or APRIL binding, said human immunoglobulin-constant domain, said reducing the serum Gd-IgA1 level, said Gd-IgA1, said reducing the proteinuria, said proteinuria, said determining the level of proteinuria in said patient, said diagnosis of proteinuria, said persistent proteinuria, said step of administering to said patient an angiotensin converting enzyme inhibitor (ACEi) and/or an angiotensin receptor blocker (ARB), said angiotensin converting enzyme inhibitor (ACEi) and/or angiotensin receptor blocker (ARB) therapy, said step of measuring the protein level in the urine of said patient, and said step of continuing to administer are as defined in any one of the embodiments disclosed above or any combination thereof.

EXEMPLARY EMBODIMENTS

Some embodiments of this disclosure relate to Embodiment I, as follows:

Embodiment 1. A method for treating a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

Embodiment 2. A method for reducing the serum Gd-IgA1 level in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

Embodiment 3. A method for reducing the proteinuria in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

Embodiment 4. A method for reducing the serum Gd-IgA1 level and the proteinuria in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

Embodiment 5. A method of treating IgA nephropathy (IgAN) in a patient, said method comprising administering to the patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain, and wherein said method comprises determining the level of proteinuria in said patient.

Embodiment 6. The method according to any one of Embodiments 1 to 5, wherein said patient has persistent proteinuria.

Embodiment 7. The method according to Embodiment 6, wherein
(a) said persistent proteinuria is a persistent proteinuria with UPCR≥1 mg/mg based on 24-hour urine collection or
(b) said persistent proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

Embodiment 8. The method according to any one of Embodiments 6 to 7, wherein said persistent proteinuria is a persistent proteinuria with UPCR≥0.75 mg/mg based on 24-hour urine collection.

Embodiment 9. The method according to any one of Embodiments 6 to 8, wherein said persistent proteinuria is a persistent proteinuria with UPCR≥1 mg/mg based on 24-hour urine collection.

Embodiment 10. The method according to Embodiment 6, wherein
(a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy or
(b) said persistent proteinuria is a persistent proteinuria with UPCR≥0.75 mg/mg based on 24-hour urine collection, as determined with said patient being on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 11. The method according to any one of Embodiments 6 or 10, wherein said persistent proteinuria is a persistent proteinuria with UPCR≥0.75 mg/mg based on 24-hour urine collection, as determined with said patient being on angiotensin converting enzyme inhibitor (ACEi) and/or angiotensin receptor blocker (ARB) therapy.

Embodiment 12. The method according to any one of Embodiments 6 or 10 to 11, wherein said persistent proteinuria is a persistent proteinuria with UPCR≥1 mg/mg on 24-hour urine collection, as determined with said patient being on angiotensin converting enzyme inhibitor (ACEi) and/or angiotensin receptor blocker (ARB) therapy.

Embodiment 13. The method according to any one of Embodiments 6 to 12, wherein said patient has had said persistent proteinuria for at least 8 weeks prior to said administration or said use of said TACI-Ig fusion molecule.

Embodiment 14. A method for treating IgA nephropathy (IgAN) in a patient, said method comprising the steps of
(1) measuring the protein level in the urine of said patient; and
(2) administering to said patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

Embodiment 15. A method of treating IgA nephropathy (IgAN) in a patient, said method comprising the steps of
(1) administering to said patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain;
(2) measuring the protein level in the urine of said patient; and
(3) continuing to administer said TACI-Ig fusion molecule to said patient if said patient has proteinuria.

Embodiment 16. A method of treating IgA nephropathy (IgAN) in a patient, said method comprising the steps of
(1) administering to said patient an angiotensin converting enzyme inhibitor (ACEi) and/or an angiotensin receptor blocker (ARB);
(2) measuring the protein level in the urine of said patient; and
(3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:
(i) a TACI extracellular domain or fragment thereof which binds BLyS (B Lymphocyte Stimulator) and/or APRIL (A Proliferation-Inducing Ligand); and
(ii) a human immunoglobulin-constant domain.

Embodiment 17. The method according to any one of Embodiments 14 to 16, wherein said measuring step further comprises determining that said patient has persistent proteinuria.

Embodiment 18. The method according to any one of Embodiments 14 to 17, wherein said measuring step further comprises
(a) determining that said patient has a persistent proteinuria with UPCR≥1 mg/mg based on 24-hour urine collection or
(b) determining that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

Embodiment 19. The method according to any one of Embodiments 14 to 18, wherein said measuring step further comprises determining that said patient has a persistent proteinuria with UPCR≥0.75 mg/mg based on 24-hour urine collection.

Embodiment 20. The method according to any one of Embodiments 14 to 19, wherein said measuring step further comprises determining that said patient has a persistent proteinuria with UPCR≥1 mg/mg based on 24-hour urine collection.

Embodiment 21. The method according to any one of Embodiments 14 to 17, wherein said measuring step further comprises
(a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or
(b) determining that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 22. The method according to any one of Embodiments 14 to 17 or 21, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 23. The method according to any one of Embodiments 14 to 17 or 21 to 22, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 24. The method according to any one of Embodiments 14 to 23, wherein said measuring step further comprises determining that said patient has had said persistent proteinuria for at least 8 weeks prior to said administration or said use of said TACI-Ig fusion molecule.

Embodiment 25. The method according to any one of Embodiments 15 to 24, wherein said measuring step (2) further comprises deciding, based on the measurement in step (2), whether step (3) is to be carried out.

Embodiment 26. The method according to any one of Embodiments 15 to 25, wherein step (3) is to be carried out only if the measuring step shows that said patient has persistent proteinuria.

Embodiment 27. The method according to any one of Embodiments 15 to 26, wherein step (3) is to be carried out only if
(a) the measuring step shows that said patient has a persistent proteinuria with UPCR≥1 mg/mg based on 24-hour urine collection or
(b) the measuring step shows that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

Embodiment 28. The method according to any one of Embodiments 15 to 27, wherein step (3) is to be carried out only if the measuring step shows that said patient has a persistent proteinuria with UPCR≥0.75 mg/mg based on 24-hour urine collection.

Embodiment 29. The method according to any one of Embodiments 15 to 28, wherein step (3) is to be carried out only if the measuring step shows that said patient has a persistent proteinuria with UPCR≥1 mg/mg based on 24-hour urine collection.

Embodiment 30. The method according to any one of Embodiments 15 to 26, wherein step (3) is to be carried out only if (a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or (b) the measuring step shows that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 31. The method according to any one of Embodiments 15 to 26 or 30, wherein step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 32. The method according to any one of Embodiments 15 to 26 or 31 to 32, wherein step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 33. The method according to any one of Embodiments 15 to 32, wherein step (3) is to be carried out only if the measuring step shows that said patient has had said persistent proteinuria for at least 8 weeks prior to said administration or said use of said TACI-Ig fusion molecule.

Embodiment 34. A transmembrane activator and calcium modulator and cyclophilin ligand-interactor (TACI)-immunoglobulin (Ig) fusion molecule for use in the treatment of IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 35. A transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 36. A transmembrane activator and calcium modulator and cyclophilin ligand-interactor (TACI)-immunoglobulin (Ig) fusion molecule for use in the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 37. A transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 38. A transmembrane activator and calcium modulator and cyclophilin ligand-interactor (TACI)-immunoglobulin (Ig) fusion molecule for use in reducing the serum Gd-IgA1 level linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 39. A transmembrane activator and calcium modulator and cyclophilin ligand-interactor (TACI)-immunoglobulin (Ig) fusion molecule for use in reducing the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 40. A transmembrane activator and calcium modulator and cyclophilin ligand-interactor (TACI)-immunoglobulin (Ig) fusion molecule for use in reducing the serum Gd-IgA1 level and the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 41. A transmembrane activator and calcium modulator and cyclophilin ligand-interactor (TACI)-immunoglobulin (Ig) fusion molecule for use in reducing the serum Gd-IgA1 level in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 42. A transmembrane activator and calcium modulator and cyclophilin ligand-interactor (TACI)-immunoglobulin (Ig) fusion molecule for use in reducing the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 43. A transmembrane activator and calcium modulator and cyclophilin ligand-interactor (TACI)-immunoglobulin (Ig) fusion molecule for use in reducing the serum Gd-IgA1 level and the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 44. A transmembrane activator and calcium modulator and cyclophilin ligand-interactor (TACI)-immunoglobulin (Ig) fusion molecule for use in reducing the serum Gd-IgA1 level in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 45. A transmembrane activator and calcium modulator and cyclophilin ligand-interactor (TACI)-immunoglobulin (Ig) fusion molecule for use in reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 46. A transmembrane activator and calcium modulator and cyclophilin ligand-interactor (TACI)-immunoglobulin (Ig) fusion molecule for use in reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 47. The TACI-Ig fusion molecule for use according to any one of Embodiments 34 to 46, wherein said use comprises determining the level of proteinuria in said patient.

Embodiment 48. The TACI-Ig fusion molecule for use according to any one of Embodiments 34 to 47, wherein said patient has proteinuria.

Embodiment 49. The TACI-Ig fusion molecule for use according to any one of Embodiments 34 to 48, wherein said patient has been diagnosed as having proteinuria.

Embodiment 50. The TACI-Ig fusion molecule for use according to any one of Embodiments 34 to 49, wherein said proteinuria is a persistent proteinuria.

Embodiment 51. The TACI-Ig fusion molecule for use according to any one of Embodiments 34 to 50, wherein (a) said persistent proteinuria is a persistent proteinuria with UPCR≥1 mg/mg based on 24-hour urine collection or (b) said persistent proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

Embodiment 52. The TACI-Ig fusion molecule for use according to any one of Embodiments 34 to 51, wherein said persistent proteinuria is a persistent proteinuria with UPCR≥0.75 mg/mg based on 24-hour urine collection.

Embodiment 53. The TACI-Ig fusion molecule for use according to any one of Embodiments 34 to 52, wherein said persistent proteinuria is a persistent proteinuria with UPCR≥1 mg/mg based on 24-hour urine collection.

Embodiment 54. The TACI-Ig fusion molecule for use according to any one of Embodiments 34 to 49, wherein (a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy or (b) said persistent proteinuria is a persistent proteinuria with UPCR≥0.75 mg/mg based on 24-hour urine collection, as determined with said patient being on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 55. The TACI-Ig fusion molecule for use according to any one of Embodiments 34 to 49 or 54, wherein said persistent proteinuria is a persistent proteinuria with UPCR≥0.75 mg/mg based on 24-hour urine collection, as determined with said patient being on angiotensin converting enzyme inhibitor (ACEi) and/or angiotensin receptor blocker (ARB) therapy.

Embodiment 56. The TACI-Ig fusion molecule for use according to any one of Embodiments 34 to 49 or 54 to 55, wherein said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy.

Embodiment 57. The TACI-Ig fusion molecule for use according to any one of Embodiments 34 to 56, wherein said use comprises the steps of (1) measuring the protein level in the urine of said patient; and (2) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 58. The TACI-Ig fusion molecule for use according to any one of Embodiments 34 to 56, wherein said use comprises the steps of (1) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

(2) measuring the protein level in the urine of said patient and (3) continuing to administer said TACI-Ig fusion molecule to said patient if said patient has proteinuria.

Embodiment 59. The TACI-Ig fusion molecule for use according to any one of Embodiments 34 to 56, wherein said use comprises the steps of (1) administering to said patient an angiotensin converting enzyme inhibitor (ACEi) and/or an angiotensin receptor blocker (ARB);

(2) measuring the protein level in the urine of said patient; and (3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 60. The TACI-Ig fusion molecule for use according to any one of Embodiments 57 to 59, wherein said measuring step further comprises determining that said patient has persistent proteinuria.

Embodiment 61. The TACI-Ig fusion molecule for use according to any one of Embodiments 57 to 60, wherein said measuring step further comprises (a) determining that said patient has a persistent proteinuria with UPCR≥1 mg/mg based on 24-hour urine collection or (b) determining that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

Embodiment 62. The TACI-Ig fusion molecule for use according to any one of Embodiments 57 to 61, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 63. The TACI-Ig fusion molecule for use according to any one of Embodiments 57 to 62, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 64. The TACI-Ig fusion molecule for use according to any one of Embodiments 57 to 60, wherein said measuring step further comprises (a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or (b) determining that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 65. The TACI-Ig fusion molecule for use according to any one of Embodiments 57 to 60 or 64, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 66. The TACI-Ig fusion molecule for use according to any one of Embodiments 57 to 60 or 64 to 65, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 67. The TACI-Ig fusion molecule for use according to any one of Embodiments 57 to 66, wherein said measuring step further comprises determining that said patient has had said persistent proteinuria for at least 8 weeks prior to said administration or said use of said TACI-Ig fusion molecule.

Embodiment 68. The TACI-Ig fusion molecule for use according to any one of Embodiments 58 to 67, wherein said measuring step (2) further comprises deciding, based on the measurement in step (2), whether step (3) is to be carried out.

Embodiment 69. The TACI-Ig fusion molecule for use according to any one of Embodiments 58 to 68, wherein step (3) is to be carried out only if the measuring step shows that said patient has persistent proteinuria.

Embodiment 70. The TACI-Ig fusion molecule for use according to any one of Embodiments 58 to 69, wherein step (3) is to be carried out only if (a) the measuring step shows that said patient has a persistent proteinuria with UPCR≥1 mg/mg based on 24-hour urine collection or (b) the measuring step shows that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

Embodiment 71. The TACI-Ig fusion molecule for use according to any one of Embodiments 58 to 70, wherein step (3) is to be carried out only if the measuring step shows that said patient has a persistent proteinuria with UPCR≥0.75 mg/mg based on 24-hour urine collection.

Embodiment 72. The TACI-Ig fusion molecule for use according to any one of Embodiments 58 to 71, wherein step (3) is to be carried out only if the measuring step shows that said patient has a persistent proteinuria with UPCR≥1 mg/mg based on 24-hour urine collection.

Embodiment 73. The TACI-Ig fusion molecule for use according to any one of Embodiments 58 to 69, wherein step (3) is to be carried out only if (a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or (b) the measuring step shows that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 74. The TACI-Ig fusion molecule for use according to any one of Embodiments 58 to 69 or 73, wherein step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 75. The TACI-Ig fusion molecule for use according to any one of Embodiments 58 to 69 or 73 to 74, wherein step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 76. The TACI-Ig fusion molecule for use according to any one of Embodiments 58 to 75, wherein step (3) is to be carried out only if the measuring step shows that said patient has had said persistent proteinuria for at least 8 weeks prior to said administration or said use of said TACI-Ig fusion molecule.

Embodiment 77. Use of a transmembrane activator and calcium modulator and cyclophilin ligand-interactor (TACI)-immunoglobulin (Ig) fusion molecule for the manufacture of a medicament for the treatment of IgA nephropathy in a patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 78. Use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level in an IgAN patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 79. Use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the proteinuria in an IgAN patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 80. Use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level and the proteinuria in an IgAN patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 81. Use of a transmembrane activator and calcium modulator and cyclophilin ligand-interactor (TACI)-immunoglobulin (Ig) fusion molecule for the manufacture of a medicament for reducing the serum Gd-IgA1 level linked to IgA nephropathy in a patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 82. Use of a transmembrane activator and calcium modulator and cyclophilin ligand-interactor (TACI)-immunoglobulin (Ig) fusion molecule for the manufacture of a medicament for reducing the proteinuria linked to IgA nephropathy in a patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 83. Use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria linked to IgA nephropathy in a patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 84. Use of a transmembrane activator and calcium modulator and cyclophilin ligand-interactor (TACI)-immunoglobulin (Ig) fusion molecule for the manufacture of a medicament for reducing the serum Gd-IgA1 level in a patient with IgA nephropathy, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 85. Use of a transmembrane activator and calcium modulator and cyclophilin ligand-interactor (TACI)-immunoglobulin (Ig) fusion molecule for the manufacture of a medicament for reducing the proteinuria in a patient with IgA nephropathy, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 86. Use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria in a patient with IgA nephropathy, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 87. Use of a transmembrane activator and calcium modulator and cyclophilin ligand-interactor (TACI)-immunoglobulin (Ig) fusion molecule for the manufacture of a medicament for reducing the serum Gd-IgA1 level in IgA nephropathy in a patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 88. Use of a transmembrane activator and calcium modulator and cyclophilin ligand-interactor (TACI)-immunoglobulin (Ig) fusion molecule for the manufacture of a medicament for reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 89. Use of a transmembrane activator and calcium modulator and cyclophilin ligand-interactor (TACI)-immunoglobulin (Ig) fusion molecule for the manufacture of a medicament for reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 90. The use according to any one of Embodiments 77 to 89, wherein said use comprises determining the level of proteinuria in said patient.

Embodiment 91. The use according to any one of Embodiments 77 to 90, wherein said patient has proteinuria.

Embodiment 92. The use according to any one of Embodiments 77 to 91, wherein said patient has been diagnosed to have proteinuria.

Embodiment 93. The use according to any one of Embodiments 77 to 92, wherein said proteinuria is a persistent proteinuria.

Embodiment 94. The use according to any one of Embodiments 77 to 93, wherein (a) said persistent proteinuria is a persistent proteinuria with UPCR≥1 mg/mg based on 24-hour urine collection or (b) said persistent proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

Embodiment 95. The use according to any one of Embodiments 77 to 94, wherein said persistent proteinuria is a persistent proteinuria with UPCR≥0.75 mg/mg based on 24-hour urine collection.

Embodiment 96. The use according to any one of Embodiments 77 to 95, wherein said persistent proteinuria is a persistent proteinuria with UPCR≥1 mg/mg based on 24-hour urine collection.

Embodiment 97. The use according to any one of Embodiments 77 to 93, wherein (a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy or (b) said persistent proteinuria is a persistent proteinuria with UPCR≥0.75 mg/mg based on 24-hour urine collection, as determined with said patient being on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 98. The use according to any one of Embodiments 77 to 93 or 97, wherein said persistent proteinuria is a persistent proteinuria with UPCR≥0.75 mg/mg based on 24-hour urine collection, as determined with said patient being on angiotensin converting enzyme inhibitor (ACEi) and/or angiotensin receptor blocker (ARB) therapy.

Embodiment 99. The use according to any one of Embodiments 77 to 93 or 97 to 98, wherein said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy.

Embodiment 100. The use according to any one of Embodiments 77 to 99, wherein said use comprises the steps of (1) measuring the protein level in the urine of said patient; and (2) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 101. The use according to any one of Embodiments 77 to 99, wherein said use comprises the steps of (1) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

(2) measuring the protein level in the urine of said patient and (3) continuing to administer said TACI-Ig fusion molecule to said patient if said patient has proteinuria.

Embodiment 102. The use according to any one of Embodiments 77 to 99, wherein said use comprises the steps of (1) administering to said patient an angiotensin converting enzyme inhibitor (ACEi) and/or an angiotensin receptor blocker (ARB);

(2) measuring the protein level in the urine of said patient; and (3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 103. The use according to any one of Embodiments 100 to 102, wherein said measuring step further comprises determining that said patient has persistent proteinuria.

Embodiment 104. The use according to any one of Embodiments 100 to 103, wherein said measuring step further comprises (a) determining that said patient has a persistent proteinuria with UPCR≥1 mg/mg based on 24-hour urine collection or (b) determining that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

Embodiment 105. The use according to any one of Embodiments 100 to 104, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 106. The use according to any one of Embodiments 100 to 105, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 107. The use according to any one of Embodiments 100 to 103, wherein said measuring step further comprises
  (a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or
  (b) determining that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 108. The use according to any one of Embodiments 100 to 103 or 107, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 109. The use according to any one of Embodiments 100 to 103 or 107 to 108, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 110. The use according to any one of Embodiments 100 to 109, wherein said measuring step further comprises determining that said patient has had said persistent proteinuria for at least 8 weeks prior to said administration or said use of said TACI-Ig fusion molecule.

Embodiment 111. The use according to any one of Embodiments 101 to 110, wherein said measuring step (2) further comprises deciding, based on the measurement in step (2), whether step (3) is to be carried out.

Embodiment 112. The use according to any one of Embodiments 101 to 111, wherein step (3) is to be carried out only if the measuring step shows that said patient has persistent proteinuria.

Embodiment 113. The use according to any one of Embodiments 101 to 112, wherein step (3) is to be carried out only if
  (a) the measuring step shows that said patient has a persistent proteinuria with UPCR≥1 mg/mg based on 24-hour urine collection or (b) the measuring step shows that said patient has a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg.

Embodiment 114. The use according to any one of Embodiments 101 to 113, wherein step (3) is to be carried out only if the measuring step shows that said patient has a persistent proteinuria with UPCR≥0.75 mg/mg based on 24-hour urine collection.

Embodiment 115. The use according to any one of Embodiments 101 to 114, wherein step (3) is to be carried out only if the measuring step shows that said patient has a persistent proteinuria with UPCR≥1 mg/mg based on 24-hour urine collection.

Embodiment 116. The use according to any one of Embodiments 101 to 112, wherein step (3) is to be carried out only if
  (a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or
  (b) the measuring step shows that said patient has a persistent proteinuria with UPCR≥0.75 mg/mg based on 24-hour urine collection while on ACEi and/or ARB therapy, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 117. The use according to any one of Embodiments 101 to 112 or 116, wherein step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 118. The use according to any one of Embodiments 101 to 112 or 116 to 117, wherein step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 119. The use according to any one of Embodiments 101 to 118, wherein step (3) is to be carried out only if the measuring step shows that said patient has had said persistent proteinuria for at least 8 weeks prior to said administration or said use of said TACI-Ig fusion molecule.

Embodiment 120. Use of a transmembrane activator and calcium modulator and cyclophilin ligand-interactor (TACI)-immunoglobulin (Ig) fusion molecule for the treatment of IgA nephropathy in a patient, wherein the TACI-Ig fusion molecule comprises:
  (i) a TACI extracellular domain or fragment thereof which binds BLyS (B Lymphocyte Stimulator) and/or APRIL (A Proliferation-Inducing Ligand); and
  (ii) a human immunoglobulin-constant domain.

Embodiment 121. Use of a transmembrane activator and calcium modulator and cyclophilin ligand-interactor (TACI)-immunoglobulin (Ig) fusion molecule for the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 122. Use of a transmembrane activator and calcium modulator and cyclophilin ligand-interactor (TACI)-immunoglobulin (Ig) fusion molecule for the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 123. Use of a transmembrane activator and calcium modulator and cyclophilin ligand-interactor (TACI)-immunoglobulin (Ig) fusion molecule for the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 124. Use of a transmembrane activator and calcium modulator and cyclophilin ligand-interactor (TACI)-immunoglobulin (Ig) fusion molecule for reducing the serum Gd-IgA1 level linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 125. Use of a transmembrane activator and calcium modulator and cyclophilin ligand-interactor (TACI)-immunoglobulin (Ig) fusion molecule for reducing the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 126. Use of a transmembrane activator and calcium modulator and cyclophilin ligand-interactor (TACI)-immunoglobulin (Ig) fusion molecule for reducing the serum Gd-IgA1 level and the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 127. Use of a transmembrane activator and calcium modulator and cyclophilin ligand-interactor (TACI)-immunoglobulin (Ig) fusion molecule for reducing the serum Gd-IgA1 level in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 128. Use of a transmembrane activator and calcium modulator and cyclophilin ligand-interactor (TACI)-immunoglobulin (Ig) fusion molecule for reducing the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 129. Use of a transmembrane activator and calcium modulator and cyclophilin ligand-interactor (TACI)-immunoglobulin (Ig) fusion molecule for reducing the serum Gd-IgA1 level and the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 130. Use of a transmembrane activator and calcium modulator and cyclophilin ligand-interactor (TACI)-immunoglobulin (Ig) fusion molecule for reducing the serum Gd-IgA1 level in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 131. Use of a transmembrane activator and calcium modulator and cyclophilin ligand-interactor (TACI)-immunoglobulin (Ig) fusion molecule for reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 132. Use of a transmembrane activator and calcium modulator and cyclophilin ligand-interactor (TACI)-immunoglobulin (Ig) fusion molecule for reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 133. The use according to any one of Embodiments 120 to 132, wherein said use comprises determining the level of proteinuria in said patient.

Embodiment 134. The use according to any one of Embodiments 120 to 133, wherein said patient has proteinuria.

Embodiment 135. The use according to any one of Embodiments 120 to 134, wherein said patient has been diagnosed to have proteinuria.

Embodiment 136. The use according to any one of Embodiments 120 to 135, wherein said proteinuria is a persistent proteinuria.

Embodiment 137. The use according to any one of Embodiments 120 to 136, wherein (a) said persistent proteinuria is a persistent proteinuria with UPCR≥1 mg/mg based on 24-hour urine collection or (b) said persistent proteinuria is a persistent proteinuria with UPCR≥0.75 mg/mg based on 24-hour urine collection, wherein at least once within 12 months prior to said administration of said TACI-Ig fusion molecule said patient has been determined to have a UPCR≥1 mg/mg based on 24-hour urine collection.

Embodiment 138. The use according to any one of Embodiments 120 to 137 wherein said persistent proteinuria is a persistent proteinuria with UPCR≥0.75 mg/mg based on 24-hour urine collection.

Embodiment 139. The use according to any one of Embodiments 120 to 138, wherein said persistent proteinuria is a persistent proteinuria with UPCR≥1 mg/mg based on 24-hour urine collection.

Embodiment 140. The use according to any one of Embodiments 120 to 139, wherein (a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy or (b) said persistent proteinuria is a persistent proteinuria with UPCR≥0.75 mg/mg based on 24-hour urine collection, as determined with said patient being on ACEi and/or ARB therapy, wherein at least once within 12 months prior to said administration of said TACI-Ig fusion molecule said patient has been determined to have a UPCR≥1 mg/mg based on 24-hour urine collection while on ACEi and/or ARB therapy.

Embodiment 141. The use according to any one of Embodiments 120 to 136 or 140, wherein said persistent proteinuria is a persistent proteinuria with UPCR≥0.75 mg/mg based on 24-hour urine collection, as determined with said patient being on angiotensin converting enzyme inhibitor (ACEi) and/or angiotensin receptor blocker (ARB) therapy.

Embodiment 142. The use according to any one of Embodiments 120 to 136 or 140 to 141, wherein said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy.

Embodiment 143. The use according to any one of Embodiments 120 to 142, wherein said use comprises the steps of (1) measuring the protein level in the urine of said patient; and (2) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 144. The use according to any one of Embodiments 120 to 142, wherein said use comprises the steps of (1) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

(2) measuring the protein level in the urine of said patient and (3) continuing to administer said TACI-Ig fusion molecule to said patient if said patient has proteinuria.

Embodiment 145. The use according to any one of Embodiments 120 to 142, wherein said use comprises the steps of (1) administering to said patient an angiotensin converting enzyme inhibitor (ACEi) and/or an angiotensin receptor blocker (ARB);

(2) measuring the protein level in the urine of said patient; and (3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 146. The use according to any one of Embodiments 143 to 145, wherein said measuring step further comprises determining that said patient has persistent proteinuria.

Embodiment 147. The use according to any one of Embodiments 143 to 146, wherein said measuring step further comprises (a) determining that said patient has a persistent proteinuria with UPCR≥1 mg/mg based on 24-hour urine collection or (b) determining that said patient has a persistent proteinuria with UPCR≥0.75 mg/mg based on 24-hour urine collection, wherein at least once within 12 months prior to said administration of said TACI-Ig fusion molecule said patient has been determined to have a UPCR≥1 mg/mg.

Embodiment 148. The use according to any one of Embodiments 143 to 147, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 149. The use according to any one of Embodiments 143 to 148, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 150. The use according to any one of Embodiments 143 to 146, wherein said measuring step further comprises (a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or (b) determining that said patient has a persistent proteinuria with UPCR≥0.75 mg/mg based on 24-hour urine collection while on ACEi and/or ARB therapy, wherein at least once within 12 months prior to said administration of said TACI-Ig fusion molecule said patient has been determined to have a UPCR≥1 mg/mg based on 24-hour urine collection while on ACEi and/or ARB therapy.

Embodiment 151. The use according to any one of Embodiments 143 to 146 or 150, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 152. The use according to any one of Embodiments 143 to 146 or 150 to 151, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 153. The use according to any one of Embodiments 143 to 152, wherein said measuring step further comprises determining that said patient has had said persistent proteinuria for at least 8 weeks prior to said administration of said TACI-Ig fusion molecule.

Embodiment 154. The use according to any one of Embodiments 144 to 153, wherein said measuring step (2) further comprises deciding, based on the measurement in step (2), whether step (3) is to be carried out.

Embodiment 155. The use according to any one of Embodiments 144 to 154, wherein step (3) is to be carried out only if the measuring step shows that said patient has persistent proteinuria.

Embodiment 156. The use according to any one of Embodiments 144 to 155, wherein step (3) is to be carried out only if (a) the measuring step shows that said patient has a persistent proteinuria with UPCR≥1 mg/mg based on 24-hour urine collection or (b) the measuring step shows that said patient has a persistent proteinuria with UPCR≥0.75 mg/mg based on 24-hour urine collection, wherein at least once within 12 months prior to said administration of said TACI-Ig fusion molecule said patient has been determined to have a UPCR≥1 mg/mg.

Embodiment 157. The use according to any one of Embodiments 144 to 156, wherein step (3) is to be carried out only if the measuring step shows that said patient has a persistent proteinuria with UPCR≥0.75 mg/mg based on 24-hour urine collection.

Embodiment 158. The use according to any one of Embodiments 144 to 157, wherein step (3) is to be carried out only if the measuring step shows that said patient has a persistent proteinuria with UPCR≥1 mg/mg based on 24-hour urine collection.

Embodiment 159. The use according to any one of Embodiments 144 to 155, wherein step (3) is to be carried out only if (a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or (b) the measuring step shows that said patient has a persistent proteinuria with UPCR≥0.75 mg/mg based on 24-hour urine collection while on ACEi and/or ARB therapy, wherein at least once within 12 months prior to said administration of said TACI-Ig fusion molecule said patient has been determined to have a UPCR≥1 mg/mg based on 24-hour urine collection while on ACEi and/or ARB therapy.

Embodiment 160. The use according to any one of Embodiments 144 to 155 or 159, wherein step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 161. The use according to any one of Embodiments 144 to 155 or 159 to 160, wherein step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 162. The use according to any one of Embodiments 144 to 161, wherein step (3) is to be carried out only if the measuring step shows that said patient has had said persistent proteinuria for at least 8 weeks prior to said administration of said TACI-Ig fusion molecule.

Embodiment 163. A pharmaceutical composition comprising a transmembrane activator and calcium modulator and cyclophilin ligand-interactor (TACI)-immunoglobulin (Ig) fusion molecule for the treatment of IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 164. A pharmaceutical composition comprising a transmembrane activator and calcium modulator and cyclophilin ligand-interactor (TACI)-immunoglobulin (Ig) fusion molecule for the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 165. A pharmaceutical composition comprising a transmembrane activator and calcium modulator and cyclophilin ligand-interactor (TACI)-immunoglobulin (Ig) fusion molecule for the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 166. A pharmaceutical composition comprising a transmembrane activator and calcium modulator and cyclophilin ligand-interactor (TACI)-immunoglobulin (Ig) fusion molecule for the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 167. A pharmaceutical composition comprising a transmembrane activator and calcium modulator and cyclophilin ligand-interactor (TACI)-immunoglobulin (Ig) fusion molecule for the treatment of IgA nephropathy by reducing the serum Gd-IgA1 level linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 168. A pharmaceutical composition comprising a transmembrane activator and calcium modulator and cyclophilin ligand-interactor (TACI)-immunoglobulin (Ig) fusion molecule for the treatment of IgA nephropathy by reducing the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 169. A pharmaceutical composition comprising a transmembrane activator and calcium modulator and cyclophilin ligand-interactor (TACI)-immunoglobulin (Ig) fusion molecule for the treatment of IgA nephropathy by reducing the serum Gd-IgA1 level and the proteinuria linked to IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 170. A pharmaceutical composition comprising a transmembrane activator and calcium modulator and cyclophilin ligand-interactor (TACI)-immunoglobulin (Ig) fusion molecule for the treatment of IgA nephropathy by reducing the serum Gd-IgA1 level in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 171. A pharmaceutical composition comprising a transmembrane activator and calcium modulator and cyclophilin ligand-interactor (TACI)-immunoglobulin (Ig) fusion molecule for the treatment of IgA nephropathy by reducing the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 172. A pharmaceutical composition comprising a transmembrane activator and calcium modulator and cyclophilin ligand-interactor (TACI)-immunoglobulin (Ig) fusion molecule for the treatment of IgA nephropathy by reducing the serum Gd-IgA1 level and the proteinuria in a patient with IgA nephropathy, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 173. A pharmaceutical composition comprising a transmembrane activator and calcium modulator and cyclophilin ligand-interactor (TACI)-immunoglobulin (Ig) fusion molecule for the treatment of IgA nephropathy by reducing the serum Gd-IgA1 level in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 174. A pharmaceutical composition comprising a transmembrane activator and calcium modulator and cyclophilin ligand-interactor (TACI)-immunoglobulin (Ig) fusion molecule for the treatment of IgA nephropathy by reducing the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 175. A pharmaceutical composition comprising a transmembrane activator and calcium modulator and cyclophilin ligand-interactor (TACI)-immunoglobulin (Ig) fusion molecule for the treatment of IgA nephropathy by reducing the serum Gd-IgA1 level and the proteinuria in IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 176. The pharmaceutical composition according to any one of Embodiments 163 to 175, wherein said treatment comprises determining the level of proteinuria in said patient.

Embodiment 177. The pharmaceutical composition according to any one of Embodiments 163 to 176, wherein said patient has proteinuria.

Embodiment 178. The pharmaceutical composition according to any one of Embodiments 163 to 177, wherein said patient has been diagnosed as having proteinuria.

Embodiment 179. The pharmaceutical composition according to any one of Embodiments 163 to 178, wherein said proteinuria is a persistent proteinuria.

Embodiment 180. The pharmaceutical composition according to any one of Embodiments 163 to 179, wherein (a) said persistent proteinuria is a persistent proteinuria with UPCR≥1 mg/mg based on 24-hour urine collection or (b) said persistent proteinuria is a persistent proteinuria with UPCR≥0.75 mg/mg based on 24-hour urine collection, wherein at least once within 12 months prior to said treatment, said patient has been determined to have a UPCR≥1 mg/mg based on 24-hour urine collection.

Embodiment 181. The pharmaceutical composition according to any one of Embodiments 163 to 180, wherein said persistent proteinuria is a persistent proteinuria with UPCR≥0.75 mg/mg based on 24-hour urine collection.

Embodiment 182. The pharmaceutical composition according to any one of Embodiments 163 to 181, wherein said persistent proteinuria is a persistent proteinuria with UPCR≥1 mg/mg based on 24-hour urine collection.

Embodiment 183. The pharmaceutical composition according to any one of Embodiments 163 to 178, wherein (a) said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy or (b) said persistent proteinuria is a persistent proteinuria with UPCR≥0.75 mg/mg based on 24-hour urine collection, as determined with said patient being on ACEi and/or ARB therapy, wherein at least once within 12 months prior to said treatment, said patient has been determined to have a UPCR≥1 mg/mg based on 24-hour urine collection while on ACEi and/or ARB therapy.

Embodiment 184. The pharmaceutical composition according to any one of Embodiments 163 to 178 or 183, wherein said persistent proteinuria is a persistent proteinuria with UPCR≥0.75 mg/mg based on 24-hour urine collection, as determined with said patient being on angiotensin converting enzyme inhibitor (ACEi) and/or angiotensin receptor blocker (ARB) therapy.

Embodiment 185. The pharmaceutical composition according to any one of Embodiments 163 to 178 or 183 to 184, wherein said persistent proteinuria is a persistent proteinuria with UPCR≥1 mg/mg based on 24-hour urine collection, as determined with said patient being on angiotensin converting enzyme inhibitor (ACEi) and/or angiotensin receptor blocker (ARB) therapy.

Embodiment 186. The pharmaceutical composition according to any one of Embodiments 163 to 185, wherein said treatment comprises the steps of (1) measuring the protein level in the urine of said patient; and (2) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 187. The pharmaceutical composition according to any one of Embodiments 163 to 185, wherein said treatment comprises the steps of (1) administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

(2) measuring the protein level in the urine of said patient and (3) continuing to administer said TACI-Ig fusion molecule to said patient if said patient has proteinuria.

Embodiment 188. The pharmaceutical composition according to any one of Embodiments 163 to 185, wherein said use comprises the steps of (1) administering to said patient an angiotensin converting enzyme inhibitor (ACEi) and/or an angiotensin receptor blocker (ARB);

(2) measuring the protein level in the urine of said patient; and (3) continuing to administer to said patient said ACEi and/or said ARB, and in addition administering to said patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 189. The pharmaceutical composition according to any one of Embodiments 186 to 188, wherein said measuring step further comprises determining that said patient has persistent proteinuria.

Embodiment 190. The pharmaceutical composition according to any one of Embodiments 186 to 189, wherein said measuring step further comprises (a) determining that said patient has a persistent proteinuria with UPCR≥1 mg/mg based on 24-hour urine collection or (b) determining that said patient has a persistent proteinuria with UPCR≥0.75 mg/mg based on 24-hour urine collection, wherein at least once within 12 months prior to said administration of said TACI-Ig fusion molecule said patient has been determined to have a UPCR≥1 mg/mg.

Embodiment 191. The pharmaceutical composition according to any one of Embodiments 186 to 190, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 192. The pharmaceutical composition according to any one of Embodiments 186 to 191, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 193. The pharmaceutical composition according to any one of Embodiments 186 to 189, wherein said measuring step further comprises (a) determining that said patient has a persistent proteinuria with UPCR≥1 mg/mg based on 24-hour urine collection while on angiotensin converting enzyme inhibitor (ACEi) and/or angiotensin receptor blocker (ARB) therapy or (b) determining that said patient has a persistent proteinuria with UPCR≥0.75 mg/mg based on 24-hour urine collection while on ACEi and/or ARB therapy, wherein at least once within 12 months prior to said administration of said TACI-Ig fusion molecule said patient has been determined to have a UPCR≥1 mg/mg based on 24-hour urine collection while on ACEi and/or ARB therapy.

Embodiment 194. The pharmaceutical composition according to any one of Embodiments 186 to 189 or 193, wherein said measuring step further comprises determining that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 195. The pharmaceutical composition according to any one of Embodiments 186 to 189 or 193 to 194, wherein said measuring step further comprises determining that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 196. The pharmaceutical composition according to any one of Embodiments 186 to 195, wherein said measuring step further comprises determining that said patient has had said persistent proteinuria for at least 8 weeks prior to said administration of said TACI-Ig fusion molecule.

Embodiment 197. The pharmaceutical composition according to any one of Embodiments 187 to 196, wherein said measuring step (2) further comprises deciding, based on the measurement in step (2), whether step (3) is to be carried out.

Embodiment 198. The pharmaceutical composition according to any one of Embodiments 187 to 197, wherein step (3) is to be carried out only if the measuring step shows that said patient has persistent proteinuria.

Embodiment 199. The pharmaceutical composition according to any one of Embodiments 187 to 198, wherein step (3) is to be carried out only if
(a) the measuring step shows that said patient has a persistent proteinuria with UPCR≥1 mg/mg based on 24-hour urine collection or
(b) the measuring step shows that said patient has a persistent proteinuria with UPCR≥0.75 mg/mg based on 24-hour urine collection, wherein at least once within 12 months prior to said administration of said TACI-Ig fusion molecule said patient has been determined to have a UPCR≥1 mg/mg.

Embodiment 200. The pharmaceutical composition according to any one of Embodiments 187 to 199, wherein step (3) is to be carried out only if the measuring step shows that said patient has a persistent proteinuria with UPCR≥0.75 mg/mg based on 24-hour urine collection.

Embodiment 201. The pharmaceutical composition according to any one of Embodiments 187 to 200, wherein step (3) is to be carried out only if the measuring step shows that said patient has a persistent proteinuria with UPCR≥1 mg/mg based on 24-hour urine collection.

Embodiment 202. The pharmaceutical composition according to any one of Embodiments 187 to 198, wherein step (3) is to be carried out only if
(a) the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy or
(b) the measuring step shows that said patient has a persistent proteinuria with UPCR≥0.75 mg/mg based on 24-hour urine collection while on ACEi and/or ARB therapy, wherein at least once within 12 months prior to said administration of said TACI-Ig fusion molecule said patient has been determined to have a UPCR≥1 mg/mg based on 24-hour urine collection while on ACEi and/or ARB therapy.

Embodiment 203. The pharmaceutical composition according to any one of Embodiments 187 to 198 or 202, wherein step (3) is to be carried out only if the measuring step shows that said patient has a persistent proteinuria with UPCR≥0.75 mg/mg based on 24-hour urine collection while on angiotensin converting enzyme inhibitor (ACEi) and/or angiotensin receptor blocker (ARB) therapy.

Embodiment 204. The pharmaceutical composition according to any one of Embodiments 187 to 198 or 202 to 203, wherein step (3) is to be carried out only if the measuring step shows that said patient has a persistent proteinuria with UPCR≥1 mg/mg based on 24-hour urine collection while on angiotensin converting enzyme inhibitor (ACEi) and/or angiotensin receptor blocker (ARB) therapy.

Embodiment 205. The pharmaceutical composition according to any one of Embodiments 187 to 204, wherein step (3) is to be carried out only if the measuring step shows that said patient has had said persistent proteinuria for at least 8 weeks prior to said administration of said TACI-Ig fusion molecule.

Embodiment 206. The method according to any one of Embodiments 1 to 33 or the TACI-Ig fusion molecule for use according to any one of Embodiments 34 to 76 or the use according to any one of Embodiments 77 to 162 or the pharmaceutical composition according to any one of Embodiments 163 to 205, wherein said TACI extracellular domain or fragment thereof binds BLyS (B Lymphocyte Stimulator).

Embodiment 207. The method according to any one of Embodiments 1 to 33 or 206 or the TACI-Ig fusion molecule for use according to any one of Embodiments 34 to 76 or 206 or the use according to any one of Embodiments 77 to 162 or 206 or the pharmaceutical composition according to any one of Embodiments 163 to 206, wherein said TACI extracellular domain or fragment thereof binds APRIL (A Proliferation-Inducing Ligand).

Embodiment 208. The method according to any one of Embodiments 1 to 33 or 206 to 207 or the TACI-Ig fusion molecule for use according to any one of Embodiments 34 to 76 or 206 to 207 or the use according to any one of Embodiments 77 to 162 or 206 to 207 or the pharmaceutical composition according to any one of Embodiments 163 to 207, wherein said TACI extracellular domain or fragment thereof binds BLyS (B Lymphocyte Stimulator) and APRIL (A Proliferation-Inducing Ligand).

Embodiment 209. The method according to any one of Embodiments 1 to 33 or 206 to 208 or the TACI-Ig fusion molecule for use according to any one of Embodiments 34 to 76 or 206 to 208 or the use according to any one of Embodiments 77 to 162 or 206 to 208 or the pharmaceutical composition according to any one of Embodiments 163 to 208, wherein binding of said TACI-Ig fusion molecule via said TACI extracellular domain or fragment thereof to BLyS inhibits binding of BLyS to the endogenous TACI receptor on B cells.

Embodiment 210. The method according to any one of Embodiments 1 to 33 or 206 to 209 or the TACI-Ig fusion molecule for use according to any one of Embodiments 34 to 76 or 206 to 209 or the use according to any one of Embodiments 77 to 162 or 206 to 209 or the pharmaceutical composition according to any one of Embodiments 163 to 209, wherein binding of said TACI-Ig fusion molecule via said TACI extracellular domain or fragment thereof to APRIL inhibits binding of APRIL to the endogenous TACI receptor on B cells.

Embodiment 211. The method according to any one of Embodiments 1 to 33 or 206 to 210 or the TACI-Ig fusion molecule for use according to any one of Embodiments 34 to 76 or 206 to 210 or the use according to any one of Embodiments 77 to 162 or 206 to 210 or the pharmaceutical composition according to any one of Embodiments 163 to 210, wherein said TACI-Ig fusion molecule consists of amino acids.

Embodiment 212. The method according to any one of Embodiments 1 to 33 or 206 to 211 or the TACI-Ig fusion molecule for use according to any one of Embodiments 34 to 76 or 206 to 211 or the use according to any one of Embodiments 77 to 162 or 206 to 211 or the pharmaceutical composition according to any one of Embodiments 163 to 211, wherein said TACI extracellular domain or fragment thereof comprises at least 60 amino acids.

Embodiment 213. The method according to any one of Embodiments 1 to 33 or 206 to 212 or the TACI-Ig fusion molecule for use according to any one of Embodiments 34 to 76 or 206 to 212 or the use according to any one of Embodiments 77 to 162 or 206 to 212 or the pharmaceutical composition according to any one of Embodiments 163 to 212, wherein said TACI extracellular domain or fragment thereof comprises at least 70 amino acids.

Embodiment 214. The method according to any one of Embodiments 1 to 33 or 206 to 213 or the TACI-Ig fusion molecule for use according to any one of Embodiments 34 to 76 or 206 to 213 or the use according to any one of Embodiments 77 to 162 or 206 to 213 or the pharmaceutical composition according to any one of Embodiments 163 to 213, wherein said TACI extracellular domain or fragment thereof comprises at least 80 amino acids.

Embodiment 215. The method according to any one of Embodiments 1 to 33 or 206 to 214 or the TACI-Ig fusion molecule for use according to any one of Embodiments 34 to 76 or 206 to 214 or the use according to any one of Embodiments 77 to 162 or 206 to 214 or the pharmaceutical composition according to any one of Embodiments 163 to 214, wherein said human immunoglobulin-constant domain comprises at least 200 amino acids.

Embodiment 216. The method according to any one of Embodiments 1 to 33 or 206 to 215 or the TACI-Ig fusion molecule for use according to any one of Embodiments 34 to 76 or 206 to 215 or the use according to any one of Embodiments 77 to 162 or 206 to 215 or the pharmaceutical composition according to any one of Embodiments 163 to 215, wherein said human immunoglobulin-constant domain comprises at least 210 amino acids.

Embodiment 217. The method according to any one of Embodiments 1 to 33 or 206 to 216 or the TACI-Ig fusion molecule for use according to any one of Embodiments 34 to 76 or 206 to 216 or the use according to any one of Embodiments 77 to 162 or 206 to 216 or the pharmaceutical composition according to any one of Embodiments 163 to 216, wherein said human immunoglobulin-constant domain comprises at least 220 amino acids.

Embodiment 218. The method according to any one of Embodiments 1 to 33 or 206 to 217 or the TACI-Ig fusion molecule for use according to any one of Embodiments 34 to 76 or 206 to 217 or the use according to any one of Embodiments 77 to 162 or 206 to 217 or the pharmaceutical composition according to any one of Embodiments 163 to 217, wherein said human immunoglobulin-constant domain comprises at least 230 amino acids.

Embodiment 219. The method according to any one of Embodiments 1 to 33 or 206 to 218 or the TACI-Ig fusion molecule for use according to any one of Embodiments 34 to 76 or 206 to 218 or the use according to any one of Embodiments 77 to 162 or 206 to 218 or the pharmaceutical composition according to any one of Embodiments 163 to 218, wherein said TACI-Ig fusion molecule consists of (i) a TACI extracellular domain or fragment thereof which binds BLyS (B Lymphocyte Stimulator) and/or APRIL (A Proliferation-Inducing Ligand) linked by a peptide bond to (ii) a human immunoglobulin-constant domain.

Embodiment 220. The method according to any one of Embodiments 1 to 33 or 206 to 219 or the TACI-Ig fusion molecule for use according to any one of Embodiments 34 to 76 or 206 to 219 or the use according to any one of Embodiments 77 to 162 or 206 to 219 or the pharmaceutical composition according to any one of Embodiments 163 to 219, wherein said TACI extracellular domain or fragment thereof has an amino acid sequence that is at least 80% identical to SEQ ID NO: 1.

Embodiment 221. The method according to any one of Embodiments 1 to 33 or 206 to 220 or the TACI-Ig fusion molecule for use according to any one of Embodiments 34 to 76 or 206 to 220 or the use according to any one of Embodiments 77 to 162 or 206 to 220 or the pharmaceutical composition according to any one of Embodiments 163 to 220, wherein said TACI extracellular domain or fragment thereof has an amino acid sequence that is at least 90% identical to SEQ ID NO: 1.

Embodiment 222. The method according to any one of Embodiments 1 to 33 or 206 to 221 or the TACI-Ig fusion molecule for use according to any one of Embodiments 34 to 76 or 206 to 221 or the use according to any one of Embodiments 77 to 162 or 206 to 221 or the pharmaceutical composition according to any one of Embodiments 163 to 221, wherein said TACI extracellular domain or fragment thereof has an amino acid sequence that is at least 95% identical to SEQ ID NO: 1.

Embodiment 223. The method according to any one of Embodiments 1 to 33 or 206 to 222 or the TACI-Ig fusion molecule for use according to any one of Embodiments 34 to 76 or 206 to 222 or the use according to any one of Embodiments 77 to 162 or 206 to 222 or the pharmaceutical composition according to any one of Embodiments 163 to 222, wherein said TACI extracellular domain or fragment thereof has an amino acid sequence comprising SEQ ID NO: 1.

Embodiment 224. The method according to any one of Embodiments 1 to 33 or 206 to 223 or the TACI-Ig fusion molecule for use according to any one of Embodiments 34 to 76 or 206 to 223 or the use according to any one of Embodiments 77 to 162 or 206 to 223 or the pharmaceutical composition according to any one of Embodiments 163 to 223, wherein said TACI extracellular domain or fragment thereof has an amino acid sequence consisting of SEQ ID NO: 1.

Embodiment 225. The method according to any one of Embodiments 1 to 33 or 206 to 224 or the TACI-Ig fusion molecule for use according to any one of Embodiments 34 to 76 or 206 to 224 or the use according to any one of Embodiments 77 to 162 or 206 to 224 or the pharmaceutical composition according to any one of Embodiments 163 to 224, wherein said human immunoglobulin-constant domain has an amino acid sequence that is at least 80% identical to SEQ ID NO: 2.

Embodiment 226. The method according to any one of Embodiments 1 to 33 or 206 to 225 or the TACI-Ig fusion molecule for use according to any one of Embodiments 34 to 76 or 206 to 225 or the use according to any one of Embodiments 77 to 162 or 206 to 225 or the pharmaceutical composition according to any one of Embodiments 163 to 225, wherein said human immunoglobulin-constant domain has an amino acid sequence that is at least 90% identical to SEQ ID NO: 2.

Embodiment 227. The method according to any one of Embodiments 1 to 33 or 206 to 226 or the TACI-Ig fusion molecule for use according to any one of Embodiments 34 to 76 or 206 to 226 or the use according to any one of Embodiments 77 to 162 or 206 to 226 or the pharmaceutical composition according to any one of Embodiments 163 to 226, wherein said human immunoglobulin-constant domain has an amino acid sequence that is at least 95% identical to SEQ ID NO: 2.

Embodiment 228. The method according to any one of Embodiments 1 to 33 or 206 to 227 or the TACI-Ig fusion molecule for use according to any one of Embodiments 34 to 76 or 206 to 227 or the use according to any one of Embodiments 77 to 162 or 206 to 227 or the pharmaceutical composition according to any one of Embodiments 163 to 227, wherein said human immunoglobulin-constant domain has an amino acid sequence comprising SEQ ID NO: 2.

Embodiment 229. The method according to any one of Embodiments 1 to 33 or 206 to 228 or the TACI-Ig fusion molecule for use according to any one of Embodiments 34 to 76 or 206 to 228 or the use according to any one of Embodiments 77 to 162 or 206 to 228 or the pharmaceutical composition according to any one of Embodiments 163 to 228, wherein said human immunoglobulin-constant domain has an amino acid sequence consisting of SEQ ID NO: 2.

Embodiment 230. The method according to any one of Embodiments 1 to 33 or 206 to 229 or the TACI-Ig fusion molecule for use according to any one of Embodiments 34 to 76 or 206 to 229 or the use according to any one of Embodiments 77 to 162 or 206 to 229 or the pharmaceutical composition according to any one of Embodiments 163 to 229, wherein said TACI-Ig fusion molecule has an amino acid sequence that is at least 80% identical to SEQ ID NO: 3.

Embodiment 231. The method according to any one of Embodiments 1 to 33 or 206 to 230 or the TACI-Ig fusion molecule for use according to any one of Embodiments 34 to 76 or 206 to 230 or the use according to any one of Embodiments 77 to 162 or 206 to 230 or the pharmaceutical composition according to any one of Embodiments 163 to 230, wherein said human immunoglobulin-constant domain has an amino acid sequence that is at least 90% identical to SEQ ID NO: 3.

Embodiment 232. The method according to any one of Embodiments 1 to 33 or 206 to 231 or the TACI-Ig fusion molecule for use according to any one of Embodiments 34 to 76 or 206 to 231 or the use according to any one of Embodiments 77 to 162 or 206 to 231 or the pharmaceutical composition according to any one of Embodiments 163 to 231, wherein said human immunoglobulin-constant domain has an amino acid sequence that is at least 95% identical to SEQ ID NO: 3.

Embodiment 233. The method according to any one of Embodiments 1 to 33 or 206 to 232 or the TACI-Ig fusion molecule for use according to any one of Embodiments 34 to 76 or 206 to 232 or the use according to any one of Embodiments 77 to 162 or 206 to 232 or the pharmaceutical composition according to any one of Embodiments 163 to 232, wherein said human immunoglobulin-constant domain has an amino acid sequence comprising SEQ ID NO: 3.

Embodiment 234. The method according to any one of Embodiments 1 to 33 or 206 to 233 or the TACI-Ig fusion molecule for use according to any one of Embodiments 34 to 76 or 206 to 233 or the use according to any one of Embodiments 77 to 162 or 206 to 233 or the pharmaceutical composition according to any one of Embodiments 163 to 233, wherein said human immunoglobulin-constant domain has an amino acid sequence consisting of SEQ ID NO: 3.

Embodiment 235. The method according to any one of Embodiments 1 to 33 or 206 to 229 or the TACI-Ig fusion molecule for use according to any one of Embodiments 34 to 76 or 206 to 229 or the use according to any one of Embodiments 77 to 162 or 206 to 229 or the pharmaceutical composition according to any one of Embodiments 163 to 229, wherein said TACI-Ig fusion molecule has an amino acid sequence that is at least 80% identical to SEQ ID NO: 4.

Embodiment 236. The method according to any one of Embodiments 1 to 33 or 206 to 229 or 235 or the TACI-Ig fusion molecule for use according to any one of Embodiments 34 to 76 or 206 to 229 or 235 or the use according to any one of Embodiments 77 to 162 or 206 to 229 or 235 or the pharmaceutical composition according to any one of Embodiments 163 to 229 or 235, wherein said human immunoglobulin-constant domain has an amino acid sequence that is at least 90% identical to SEQ ID NO: 4.

Embodiment 237. The method according to any one of Embodiments 1 to 33 or 206 to 229 or 235 to 236 or the TACI-Ig fusion molecule for use according to any one of Embodiments 34 to 76 or 206 to 229 or 235 to 236 or the use according to any one of Embodiments 77 to 162 or 206 to 229 or 235 to 236 or the pharmaceutical composition according to any one of Embodiments 163 to 229 or 235 to 236, wherein said human immunoglobulin-constant domain has an amino acid sequence that is at least 95% identical to SEQ ID NO: 4.

Embodiment 238. The method according to any one of Embodiments 1 to 33 or 206 to 229 or 235 to 237 or the TACI-Ig fusion molecule for use according to any one of Embodiments 34 to 76 or 206 to 229 or 235 to 237 or the use according to any one of Embodiments 77 to 162 or 206 to 229 or 235 to 237 or the pharmaceutical composition according to any one of Embodiments 163 to 229 or 235 to 237, wherein said human immunoglobulin-constant domain has an amino acid sequence comprising SEQ ID NO: 4.

Embodiment 239. The method according to any one of Embodiments 1 to 33 or 206 to 229 or 235 to 238 or the TACI-Ig fusion molecule for use according to any one of Embodiments 34 to 76 or 206 to 229 or 235 to 238 or the use according to any one of Embodiments 77 to 162 or 206 to 229 or 235 to 238 or the pharmaceutical composition according to any one of Embodiments 163 to 229 or 235 to 238, wherein said human immunoglobulin-constant domain has an amino acid sequence consisting of SEQ ID NO: 4.

Embodiment 240. The method according to any one of Embodiments 1 to 33 or 206 to 229 or the TACI-Ig fusion molecule for use according to any one of Embodiments 34 to 76 or 206 to 229 or the use according to any one of Embodiments 77 to 162 or 206 to 229 or the pharmaceutical composition according to any one of Embodiments 163 to 229, wherein said TACI-Ig fusion molecule has an amino acid sequence that is at least 80% identical to at least one of SEQ ID NO: 5 to 9.

Embodiment 241. The method according to any one of Embodiments 1 to 33 or 206 to 229 or 240 or the TACI-Ig fusion molecule for use according to any one of Embodiments 34 to 76 or 206 to 229 or 240 or the use according to any one of Embodiments 77 to 162 or 206 to 229 or 240 or the pharmaceutical composition according to any one of Embodiments 163 to 229 or 240, wherein said TACI-Ig fusion molecule has an amino acid sequence that is at least 90% identical to at least one of SEQ ID NO: 5 to 9.

Embodiment 242. The method according to any one of Embodiments 1 to 33 or 206 to 229 or 240 to 241 or the TACI-Ig fusion molecule for use according to any one of Embodiments 34 to 76 or 206 to 229 or 240 to 241 or the use according to any one of Embodiments 77 to 162 or 206 to 229 or 240 to 241 or the pharmaceutical composition according to any one of Embodiments 163 to 229 or 240 to 241, wherein said TACI-Ig fusion molecule has an amino acid sequence that is at least 95% identical to at least one of SEQ ID NO: 5 to 9.

Embodiment 243. The method according to any one of Embodiments 1 to 33 or 206 to 229 or 240 to 242 or the TACI-Ig fusion molecule for use according to any one of Embodiments 34 to 76 or 206 to 229 or 240 to 242 or the use according to any one of Embodiments 77 to 162 or 206 to 229 or 240 to 242 or the pharmaceutical composition according to any one of Embodiments 163 to 229 or 240 to 242, wherein said TACI-Ig fusion molecule has an amino acid sequence comprising at least one of SEQ ID NO: 5 to 9.

Embodiment 244. The method according to any one of Embodiments 1 to 33 or 206 to 229 or 240 to 243 or the TACI-Ig fusion molecule for use according to any one of Embodiments 34 to 76 or 206 to 229 or 240 to 243 or the use according to any one of Embodiments 77 to 162 or 206 to 229 or 240 to 243 or the pharmaceutical composition according to any one of Embodiments 163 to 229 or 240 to 242, wherein said TACI-Ig fusion molecule has an amino acid sequence consisting of one of SEQ ID NO: 5 to 9.

Embodiment 245. The method according to any one of Embodiments 1 to 33 or 206 to 219 or the TACI-Ig fusion molecule for use according to any one of Embodiments 34 to 76 or 206 to 219 or the use according to any one of Embodiments 77 to 162 or 206 to 219 or the pharmaceutical composition according to any one of Embodiments 163 to 219, wherein said TACI-Ig fusion molecule is atacicept or telitacicept.

Embodiment 246. The method according to any one of Embodiments 1 to 33 or 206 to 219 or the TACI-Ig fusion molecule for use according to any one of Embodiments 34 to 76 or 206 to 219 or the use according to any one of Embodiments 77 to 162 or 206 to 219 or the pharmaceutical composition according to any one of Embodiments 163 to 219, wherein said TACI-Ig fusion molecule is telitacicept.

Embodiment 247. The method according to any one of Embodiments 1 to 33 or 206 to 219 or the TACI-Ig fusion molecule for use according to any one of Embodiments 34 to 76 or 206 to 219 or the use according to any one of Embodiments 77 to 162 or 206 to 219 or the pharmaceutical composition according to any one of Embodiments 163 to 219, wherein said TACI-Ig fusion molecule is atacicept.

Embodiment 248. The method according to any one of Embodiments 1 to 33 or 206 to 247 or the TACI-Ig fusion molecule for use according to any one of Embodiments 34 to 76 or 206 to 247 or the use according to any one of Embodiments 77 to 162 or 206 to 247 or the pharmaceutical composition according to any one of Embodiments 163 to 247, wherein said patient is a mammal.

Embodiment 249. The method according to any one of Embodiments 1 to 33 or 206 to 248 or the TACI-Ig fusion molecule for use according to any one of Embodiments 34 to 76 or 206 to 248 or the use according to any one of Embodiments 77 to 162 or 206 to 248 or the pharmaceutical composition according to any one of Embodiments 163 to 248, wherein said patient is a human.

Embodiment 250. The method according to any one of Embodiments 1 to 33 or 206 to 249 or the TACI-Ig fusion molecule for use according to any one of Embodiments 34 to 76 or 206 to 249 or the use according to any one of Embodiments 77 to 162 or 206 to 249 or the pharmaceutical composition according to any one of Embodiments 163 to 249, wherein said human is at least 18 years old.

Embodiment 251. The method according to any one of Embodiments 1 to 33 or 206 to 250 or the TACI-Ig fusion molecule for use according to any one of Embodiments 34 to 76 or 206 to 250 or the use according to any one of Embodiments 77 to 162 or 206 to 250 or the pharmaceutical composition according to any one of Embodiments 163 to 250, wherein said patient is of white or Asian race.

Embodiment 252. The method according to any one of Embodiments 1 to 33 or 206 to 251 or the TACI-Ig fusion molecule for use according to any one of Embodiments 34 to 76 or 206 to 251 or the use according to any one of Embodiments 77 to 162 or 206 to 251 or the pharmaceutical composition according to any one of Embodiments 163 to 251, wherein said patient is of white race.

Embodiment 253. The method according to any one of Embodiments 1 to 33 or 206 to 252 or the TACI-Ig fusion molecule for use according to any one of Embodiments 34 to 76 or 206 to 252 or the use according to any one of Embodiments 77 to 162 or 206 to 252 or the pharmaceutical composition according to any one of Embodiments 163 to 252, wherein said patient has proteinuria.

Embodiment 254. The method according to any one of Embodiments 1 to 33 or 206 to 253 or the TACI-Ig fusion molecule for use according to any one of Embodiments 34 to 76 or 206 to 253 or the use according to any one of Embodiments 77 to 162 or 206 to 253 or the pharmaceutical composition according to any one of Embodiments 163 to 253, wherein said patient has been diagnosed to have proteinuria.

Embodiment 255. The method according to any one of Embodiments 1 to 33 or 206 to 254 or the TACI-Ig fusion molecule for use according to any one of Embodiments 34 to 76 or 206 to 254 or the use according to any one of Embodiments 77 to 162 or 206 to 254 or the pharmaceutical composition according to any one of Embodiments 163 to 254, wherein said method comprises the step of determining whether said patient has proteinuria.

Embodiment 256. The method according to any one of Embodiments 1 to 33 or 206 to 255 or the TACI-Ig fusion molecule for use according to any one of Embodiments 34 to 76 or 206 to 255 or the use according to any one of Embodiments 77 to 162 or 206 to 255 or the pharmaceutical composition according to any one of Embodiments 163 to 255, wherein said method comprises the step of determining whether said patient has proteinuria, and said patient is subjected to said treatment by administration of said TACI-Ig fusion molecule only if said patient has proteinuria.

Embodiment 257. The method according to any one of Embodiments 1 to 33 or 206 to 256 or the TACI-Ig fusion molecule for use according to any one of Embodiments 34 to 76 or 206 to 256 or the use according to any one of Embodiments 77 to 162 or 206 to 256 or the pharmaceutical composition according to any one of Embodiments 163 to 256, wherein said proteinuria is a persistent proteinuria.

Embodiment 258. The method according to any one of Embodiments 1 to 33 or 206 to 257 or the TACI-Ig fusion molecule for use according to any one of Embodiments 34 to 76 or 206 to 257 or the use according to any one of Embodiments 77 to 162 or 206 to 257 or the pharmaceutical composition according to any one of Embodiments 163 to 257, wherein said proteinuria is a proteinuria, preferably a persistent proteinuria, of at least 0.8 g/day (total protein based on 24-hour urine collection).

Embodiment 259. The method according to any one of Embodiments 1 to 33 or 206 to 258 or the TACI-Ig fusion molecule for use according to any one of Embodiments 34 to 76 or 206 to 258 or the use according to any one of Embodiments 77 to 162 or 206 to 258 or the pharmaceutical composition according to any one of Embodiments 163 to 258, wherein said proteinuria is a proteinuria, preferably a persistent proteinuria, of at least 1.0 g/day (total protein based on 24-hour urine collection).

Embodiment 260. The method according to any one of Embodiments 1 to 33 or 206 to 259 or the TACI-Ig fusion molecule for use according to any one of Embodiments 34 to 76 or 206 to 259 or the use according to any one of Embodiments 77 to 162 or 206 to 259 or the pharmaceutical composition according to any one of Embodiments 163 to 259, wherein said proteinuria is a proteinuria, preferably a persistent proteinuria, of at least 1.3 g/day (total protein based on 24-hour urine collection).

Embodiment 261. The method according to any one of Embodiments 1 to 33 or 206 to 260 or the TACI-Ig fusion molecule for use according to any one of Embodiments 34 to 76 or 206 to 260 or the use according to any one of Embodiments 77 to 162 or 206 to 260 or the pharmaceutical composition according to any one of Embodiments 163 to 260, wherein said proteinuria is a proteinuria, preferably a persistent proteinuria, of at least 1.5 g/day (total protein based on 24-hour urine collection).

Embodiment 262. The method according to any one of Embodiments 1 to 33 or 206 to 261 or the TACI-Ig fusion molecule for use according to any one of Embodiments 34 to 76 or 206 to 261 or the use according to any one of Embodiments 77 to 162 or 206 to 261 or the pharmaceutical composition according to any one of Embodiments 163 to 261, wherein said proteinuria is a proteinuria, preferably a persistent proteinuria, of at least 2.0 g/day (total protein based on 24-hour urine collection).

Embodiment 263. The method according to any one of Embodiments 1 to 33 or 206 to 262 or the TACI-Ig fusion molecule for use according to any one of Embodiments 34 to 76 or 206 to 262 or the use according to any one of Embodiments 77 to 162 or 206 to 262 or the pharmaceutical composition according to any one of Embodiments 163 to 262, wherein said proteinuria is a proteinuria, preferably a persistent proteinuria, of up to 6.0 g/day (total protein based on 24-hour urine collection).

Embodiment 264. The method according to any one of Embodiments 1 to 33 or 206 to 263 or the TACI-Ig fusion molecule for use according to any one of Embodiments 34 to 76 or 206 to 263 or the use according to any one of Embodiments 77 to 162 or 206 to 263 or the pharmaceutical composition according to any one of Embodiments 163 to 263, wherein said proteinuria is a proteinuria, preferably a persistent proteinuria, of up to 5.0 g/day.

Embodiment 265. The method according to any one of Embodiments 1 to 33 or 206 to 264 or the TACI-Ig fusion molecule for use according to any one of Embodiments 34 to 76 or 206 to 264 or the use according to any one of Embodiments 77 to 162 or 206 to 264 or the pharmaceutical composition according to any one of Embodiments 163 to 264, wherein said proteinuria is a proteinuria, preferably a persistent proteinuria, of up to 4.0 g/day (total protein based on 24-hour urine collection).

Embodiment 266. The method according to any one of Embodiments 1 to 33 or 206 to 265 or the TACI-Ig fusion molecule for use according to any one of Embodiments 34 to 76 or 206 to 265 or the use according to any one of Embodiments 77 to 162 or 206 to 265 or the pharmaceutical composition according to any one of Embodiments 163 to 265, wherein said proteinuria is a proteinuria, preferably a persistent proteinuria, of 1.0 to 6.0 g/day (total protein based on 24-hour urine collection).

Embodiment 267. The method according to any one of Embodiments 1 to 33 or 206 to 266 or the TACI-Ig fusion molecule for use according to any one of Embodiments 34 to 76 or 206 to 266 or the use according to any one of Embodiments 77 to 162 or 206 to 266 or the pharmaceutical composition according to any one of Embodiments 163 to 266, wherein said proteinuria is a proteinuria, preferably a persistent proteinuria, of 1.3 to 6.0 g/day (total protein based on 24-hour urine collection).

Embodiment 268. The method according to any one of Embodiments 1 to 33 or 206 to 267 or the TACI-Ig fusion molecule for use according to any one of Embodiments 34 to 76 or 206 to 267 or the use according to any one of Embodiments 77 to 162 or 206 to 267 or the pharmaceutical composition according to any one of Embodiments 163 to 267, wherein said proteinuria is characterized by a urine-protein creatinine ratio (UPCR), based on 24-hour urine collection, of at least 0.75 mg/mg.

Embodiment 269. The method according to any one of Embodiments 1 to 33 or 206 to 268 or the TACI-Ig fusion molecule for use according to any one of Embodiments 34 to 76 or 206 to 268 or the use according to any one of Embodiments 77 to 162 or 206 to 268 or the pharmaceutical composition according to any one of Embodiments 163 to 268, wherein said proteinuria is characterized by a urine-protein creatinine ratio (UPCR), based on 24-hour urine collection, of at least 1.0 mg/mg.

Embodiment 270. The method according to any one of Embodiments 1 to 33 or 206 to 269 or the TACI-Ig fusion molecule for use according to any one of Embodiments 34 to 76 or 206 to 269 or the use according to any one of Embodiments 77 to 162 or 206 to 269 or the pharmaceutical composition according to any one of Embodiments 163 to 269, wherein said proteinuria is characterized by a urine-protein creatinine ratio (UPCR), based on 24-hour urine collection, of at least 1.5 mg/mg.

Embodiment 271. The method according to any one of Embodiments 1 to 33 or 206 to 270 or the TACI-Ig fusion molecule for use according to any one of Embodiments 34 to 76 or 206 to 270 or the use according to any one of Embodiments 77 to 162 or 206 to 270 or the pharmaceutical composition according to any one of Embodiments 163 to 270, wherein said proteinuria is characterized by a urine-protein creatinine ratio (UPCR), based on 24-hour urine collection, of at least 2.0 mg/mg.

Embodiment 272. The method according to any one of Embodiments 1 to 33 or 206 to 271 or the TACI-Ig fusion molecule for use according to any one of Embodiments 34 to 76 or 206 to 271 or the use according to any one of Embodiments 77 to 162 or 206 to 271 or the pharmaceutical composition according to any one of Embodiments 163 to 271, wherein said proteinuria is characterized by a 24-hour urine-protein creatinine ratio (UPCR), based on 24-hour urine collection, of up to 6.0 mg/mg.

Embodiment 273. The method according to any one of Embodiments 1 to 33 or 206 to 272 or the TACI-Ig fusion molecule for use according to any one of Embodiments 34 to 76 or 206 to 272 or the use according to any one of Embodiments 77 to 162 or 206 to 272 or the pharmaceutical composition according to any one of Embodiments 163 to 272, wherein said proteinuria is characterized by a urine-protein creatinine ratio (UPCR), based on 24-hour urine collection, of up to 5.0 mg/mg.

Embodiment 274. The method according to any one of Embodiments 1 to 33 or 206 to 273 or the TACI-Ig fusion molecule for use according to any one of Embodiments 34 to 76 or 206 to 273 or the use according to any one of Embodiments 77 to 162 or 206 to 273 or the pharmaceutical composition according to any one of Embodiments 163 to 273, wherein said proteinuria is characterized by a urine-protein creatinine ratio (UPCR), based on 24-hour urine collection, of up to 4.0 mg/mg.

Embodiment 275. The method according to any one of Embodiments 1 to 33 or 206 to 267 or the TACI-Ig fusion molecule for use according to any one of Embodiments 34 to 76 or 206 to 267 or the use according to any one of Embodiments 77 to 162 or 206 to 267 the pharmaceutical composition according to any one of Embodiments 163 to 267, wherein said proteinuria is characterized by a urine-protein creatinine ratio (UPCR), based on 24-hour urine collection, of 1.0 to 6.0 mg/mg.

Embodiment 276. The method according to any one of Embodiments 1 to 33 or 206 to 267 or the TACI-Ig fusion molecule for use according to any one of Embodiments 34 to 76 or 206 to 267 or the use according to any one of Embodiments 77 to 162 or 206 to 267 or the pharmaceutical composition according to any one of Embodiments 163 to 267, wherein said proteinuria is characterized by a urine-protein creatinine ratio (UPCR), based on 24-hour urine collection, of 1.5 to 5.0 mg/mg.

Embodiment 277. The method according to any one of Embodiments 1 to 33 or 206 to 267 or the TACI-Ig fusion molecule for use according to any one of Embodiments 34 to 76 or 206 to 267 or the use according to any one of Embodiments 77 to 162 or 206 to 267 or the pharmaceutical composition according to any one of Embodiments 163 to 267, wherein said proteinuria is characterized by a urine-protein creatinine ratio (UPCR), based on 24-hour urine collection, of 1.5 to 4.0 mg/mg.

Embodiment 278. The method according to any one of Embodiments 1 to 33 or 206 to 277 or the TACI-Ig fusion molecule for use according to any one of Embodiments 34 to 76 or 206 to 277 or the use according to any one of Embodiments 77 to 162 or 206 to 277 or the pharmaceutical composition according to any one of Embodiments 163 to 277, wherein (a) said proteinuria is a persistent proteinuria with UPCR≥1 mg/mg based on 24-hour urine collection; or (b) said proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

Embodiment 279. The method according to any one of Embodiments 1 to 33 or 206 to 278 or the TACI-Ig fusion molecule for use according to any one of Embodiments 34 to 76 or 206 to 278 or the use according to any one of Embodiments 77 to 162 or 206 to 278 or the pharmaceutical composition according to any one of Embodiments 163 to 278, wherein said proteinuria is a persistent proteinuria with UPCR≥0.75 mg/mg based on 24-hour urine collection.

Embodiment 280. The method according to any one of Embodiments 1 to 33 or 206 to 279 or the TACI-Ig fusion molecule for use according to any one of Embodiments 34 to 76 or 206 to 279 or the use according to any one of Embodiments 77 to 162 or 206 to 279 or the pharmaceutical composition according to any one of Embodiments 163 to 279, wherein said proteinuria is a persistent proteinuria with UPCR≥1 mg/mg based on 24-hour urine collection.

Embodiment 281. The method according to any one of Embodiments 1 to 33 or 206 to 277 or the TACI-Ig fusion molecule for use according to any one of Embodiments 34 to 76 or 206 to 277 or the use according to any one of Embodiments 77 to 162 or 206 to 277 or the pharmaceutical composition according to any one of Embodiments 163 to 277, wherein (a) said patient is on ACEi and/or ARB therapy and said proteinuria is a persistent proteinuria with UPCR≥1 mg/mg based on 24-hour urine collection; or (b) said patient is on ACEi and/or ARB therapy and said proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection while on ACEi and/or ARB therapy.

Embodiment 282. The method according to any one of Embodiments 1 to 33 or 206 to 277 or 281 or the TACI-Ig fusion molecule for use according to any one of Embodiments 34 to 76 or 206 to 277 or 281 or the use according to any one of Embodiments 77 to 162 or 206 to 277 or 281 or the pharmaceutical composition according to any one of Embodiments 163 to 277 or 281, wherein said patient is on ACEi and/or ARB therapy and said proteinuria is a persistent proteinuria with UPCR≥0.75 mg/mg based on 24-hour urine collection.

Embodiment 283. The method according to any one of Embodiments 1 to 33 or 206 to 277 or 281 to 282 or the TACI-Ig fusion molecule for use according to any one of Embodiments 34 to 76 or 206 to 277 or 281 to 282 or the use according to any one of Embodiments 77 to 162 or 206 to 277 or 281 to 282 or the pharmaceutical composition according to any one of Embodiments 163 to 277 or 281 to 282, wherein said patient is on ACEi and/or ARB therapy and said proteinuria is a persistent proteinuria with UPCR≥1 mg/mg based on 24-hour urine collection.

Embodiment 284. The method according to any one of Embodiments 1 to 33 or 206 to 283 or the TACI-Ig fusion molecule for use according to any one of Embodiments 34 to 76 or 206 to 283 or the use according to any one of Embodiments 77 to 162 or 206 to 283 or the pharmaceutical composition according to any one of Embodiments 163 to 283, wherein said IgA nephropathy is an IgA nephropathy confirmed by kidney biopsy.

Embodiment 285. The method according to any one of Embodiments 1 to 33 or 206 to 284 or the TACI-Ig fusion molecule for use according to any one of Embodiments 34 to 76 or 206 to 284 or the use according to any one of Embodiments 77 to 162 or 206 to 284 or the pharmaceutical composition according to any one of Embodiments 163 to 284, wherein said patient has been treated with an angiotensin converting enzyme (ACE) inhibitor and/or angiotensin receptor blocker (ARB) prior to said administration or said use of said TACI-Ig fusion molecule.

Embodiment 286. The method according to any one of Embodiments 1 to 33 or 206 to 285 or the TACI-Ig fusion molecule for use according to any one of Embodiments 34 to 76 or 206 to 285 or the use according to any one of Embodiments 77 to 162 or 206 to 285 or the pharmaceutical composition according to any one of Embodiments 163 to 285, wherein said patient has been treated with an angiotensin converting enzyme (ACE) inhibitor and/or angiotensin receptor blocker (ARB) for at least 8 weeks prior to said administration or said use of said TACI-Ig fusion molecule.

Embodiment 287. The method according to any one of Embodiments 1 to 33 or 206 to 286 or the TACI-Ig fusion molecule for use according to any one of Embodiments 34 to 76 or 206 to 286 or the use according to any one of Embodiments 77 to 162 or 206 to 286 or the pharmaceutical composition according to any one of Embodiments 163 to 286, wherein said patient has been treated with an angiotensin converting enzyme (ACE) inhibitor and/or angiotensin receptor blocker (ARB) for at least 12 weeks prior to said administration or said use of said TACI-Ig fusion molecule.

Embodiment 288. The method according to any one of Embodiments 1 to 33 or 206 to 287 or the TACI-Ig fusion molecule for use according to any one of Embodiments 34 to 76 or 206 to 287 or the use according to any one of Embodiments 77 to 162 or 206 to 287 or the pharmaceutical composition according to any one of Embodiments 163 to 287, wherein said patient has not been treated with immunosuppressant concomitant to said treatment with said angiotensin converting enzyme (ACE) inhibitor and/or angiotensin receptor blocker (ARB).

Embodiment 289. The method according to any one of Embodiments 1 to 33 or 206 to 288 or the TACI-Ig fusion molecule for use according to any one of Embodiments 34 to 76 or 206 to 288 or the use according to any one of Embodiments 77 to 162 or 206 to 288 or the pharmaceutical composition according to any one of Embodiments 163 to 288, wherein said patient has been treated with an angiotensin converting enzyme (ACE) inhibitor and/or angiotensin receptor blocker (ARB) at stable dose for at least 8 weeks prior to said administration or said use of said TACI-Ig fusion molecule.

Embodiment 290. The method according to any one of Embodiments 1 to 33 or 206 to 289 or the TACI-Ig fusion molecule for use according to any one of Embodiments 34 to 76 or 206 to 289 or the use according to any one of Embodiments 77 to 162 or 206 to 289 or the pharmaceutical composition according to any one of Embodiments 163 to 289, wherein an angiotensin converting enzyme (ACE) inhibitor and/or angiotensin receptor blocker (ARB) is administered as a background therapy to said patient simultaneously to said administration or said use of said TACI-Ig fusion molecule.

Embodiment 291. The method according to any one of Embodiments 1 to 33 or 206 to 290 or the TACI-Ig fusion molecule for use according to any one of Embodiments 34 to 76 or 206 to 290 or the use according to any one of Embodiments 77 to 162 or 206 to 290 or the pharmaceutical composition according to any one of Embodiments 163 to 290, wherein said patient has an Estimated Glomerular Filtration Rate (eGFR)≥35 mL/min/1.73 m$^2$.

Embodiment 292. The method according to any one of Embodiments 1 to 33 or 206 to 291 or the TACI-Ig fusion molecule for use according to any one of Embodiments 34 to 76 or 206 to 291 or the use according to any one of Embodiments 77 to 162 or 206 to 291 or the pharmaceutical composition according to any one of Embodiments 163 to 291, wherein the serum IgG level of said patient is ≥6 g/L.

Embodiment 293. The method according to any one of Embodiments 1 to 33 or 206 to 292 or the TACI-Ig fusion molecule for use according to any one of Embodiments 34 to 76 or 206 to 292 or the use according to any one of Embodiments 77 to 162 or 206 to 292 or the pharmaceutical composition according to any one of Embodiments 163 to 292, wherein said IgA nephropathy of said patient has not been treated with cyclophosphamide.

Embodiment 294. The method according to any one of Embodiments 1 to 33 or 206 to 293 or the TACI-Ig fusion molecule for use according to any one of Embodiments 34 to 76 or 206 to 293 or the use according to any one of Embodiments 77 to 162 or 206 to 293 or the pharmaceutical composition according to any one of Embodiments 163 to 293, wherein said patient has an increased level of serum Gd-IgA1 compared to healthy individuals.

Embodiment 295. The method according to any one of Embodiments 1 to 33 or 206 to 294 or the TACI-Ig fusion molecule for use according to any one of Embodiments 34 to 76 or 206 to 294 or the use according to any one of Embodiments 77 to 162 or 206 to 294 or the pharmaceutical composition according to any one of Embodiments 163 to 294, wherein said patient has a level of serum Gd-IgA1 that is increased by a least 25%, preferably by at least 50% compared to healthy individuals.

Embodiment 296. The method according to any one of Embodiments 1 to 33 or 206 to 295 or the TACI-Ig fusion molecule for use according to any one of Embodiments 34 to 76 or 206 to 295 or the use according to any one of Embodiments 77 to 162 or 206 to 295 or the pharmaceutical composition according to any one of Embodiments 163 to 295, wherein said patient has a level of serum Gd-IgA1 that is increased by a least 75% compared to healthy individuals.

Embodiment 297. The method according to any one of Embodiments 1 to 33 or 206 to 296 or the TACI-Ig fusion molecule for use according to any one of Embodiments 34 to 76 or 206 to 296 or the use according to any one of Embodiments 77 to 162 or 206 to 296 or the pharmaceutical composition according to any one of Embodiments 163 to 296, wherein said patient has an increased BLyS level in serum compared to healthy individuals that do not have IgAN.

Embodiment 298. The method according to any one of Embodiments 1 to 33 or 206 to 297 or the TACI-Ig fusion molecule for use according to any one of Embodiments 34 to 76 or 206 to 297 or the use according to any one of Embodiments 77 to 162 or 206 to 297 or the pharmaceutical composition according to any one of Embodiments 163 to 297, wherein said patient has been diagnosed to have an increased BLyS level in serum compared to healthy individuals that do not have IgAN.

Embodiment 299. The method according to any one of Embodiments 1 to 33 or 206 to 298 or the TACI-Ig fusion molecule for use according to any one of Embodiments 34 to 76 or 206 to 298 or the use according to any one of Embodiments 77 to 162 or 206 to 298 or the pharmaceutical composition according to any one of Embodiments 163 to 298, wherein said method comprises the step of determining the level of the cytokine BLyS in the serum of said patient.

Embodiment 300. The method according to any one of Embodiments 1 to 33 or 206 to 299 or the TACI-Ig fusion molecule for use according to any one of Embodiments 34 to 76 or 206 to 299 or the use according to any one of Embodiments 77 to 162 or 206 to 299 or the pharmaceutical composition according to any one of Embodiments 163 to 299, wherein said method comprises the step of determining the level of the cytokine BLyS in the serum of said patient, and wherein said patient is subjected to the administration of said TACI-Ig fusion molecule only if said patient has an increased BLyS level in serum compared to healthy individuals that do not have IgAN.

Embodiment 301. The method according to any one of Embodiments 1 to 33 or 206 to 300 or the TACI-Ig fusion molecule for use according to any one of Embodiments 34 to 76 or 206 to 300 or the use according to any one of Embodiments 77 to 162 or 206 to 300 or the pharmaceutical composition according to any one of Embodiments 163 to 300, wherein said increased BLyS level in serum is increased by at least 10% compared to healthy individuals that do not have IgAN.

Embodiment 302. The method according to any one of Embodiments 1 to 33 or 206 to 301 or the TACI-Ig fusion molecule for use according to any one of Embodiments 34 to 76 or 206 to 301 or the use according to any one of Embodiments 77 to 162 or 206 to 301 or the pharmaceutical composition according to any one of Embodiments 163 to 301, wherein said increased BLyS level in serum is increased by at least 25% compared to healthy individuals that do not have IgAN.

Embodiment 303. The method according to any one of Embodiments 1 to 33 or 206 to 302 or the TACI-Ig fusion molecule for use according to any one of Embodiments 34 to 76 or 206 to 302 or the use according to any one of Embodiments 77 to 162 or 206 to 302 or the pharmaceutical composition according to any one of Embodiments 163 to 302, wherein said increased BLyS level in serum is increased by at least 50% compared to healthy individuals that do not have IgAN.

Embodiment 304. The method according to any one of Embodiments 1 to 33 or 206 to 303 or the TACI-Ig fusion molecule for use according to any one of Embodiments 34 to 76 or 206 to 303 or the use according to any one of Embodiments 77 to 162 or 206 to 303 or the pharmaceutical composition according to any one of Embodiments 163 to 303, wherein said patient has an increased APRIL level in serum compared to healthy individuals that do not have IgAN.

Embodiment 305. The method according to any one of Embodiments 1 to 33 or 206 to 304 or the TACI-Ig fusion molecule for use according to any one of Embodiments 34 to 76 or 206 to 304 or the use according to any one of Embodiments 77 to 162 or 206 to 304 or the pharmaceutical composition according to any one of Embodiments 163 to 304, wherein said patient has been diagnosed to have an increased APRIL level in serum compared to healthy individuals that do not have IgAN.

Embodiment 306. The method according to any one of Embodiments 1 to 33 or 206 to 305 or the TACI-Ig fusion molecule for use according to any one of Embodiments 34 to 76 or 206 to 305 or the use according to any one of Embodiments 77 to 162 or 206 to 305 or the pharmaceutical composition according to any one of Embodiments 163 to 305, wherein said method comprises the step of determining the level of the cytokine APRIL in the serum of said patient.

Embodiment 307. The method according to any one of Embodiments 1 to 33 or 206 to 306 or the TACI-Ig fusion molecule for use according to any one of Embodiments 34 to 76 or 206 to 306 or the use according to any one of Embodiments 77 to 162 or 206 to 306 or the pharmaceutical composition according to any one of Embodiments 163 to 306, wherein said method comprises the step of determining the level of the cytokine APRIL in the serum of said patient, and wherein said patient is subjected to the administration of said TACI-Ig fusion molecule only if said patient has an increased APRIL level in serum compared to healthy individuals that do not have IgAN.

Embodiment 308. The method according to any one of Embodiments 1 to 33 or 206 to 307 or the TACI-Ig fusion molecule for use according to any one of Embodiments 34 to 76 or 206 to 307 or the use according to any one of Embodiments 77 to 162 or 206 to 307 or the pharmaceutical composition according to any one of Embodiments 163 to 307, wherein said increased APRIL level in serum is increased by at least 10% compared to healthy individuals that do not have IgAN.

Embodiment 309. The method according to any one of Embodiments 1 to 33 or 206 to 308 or the TACI-Ig fusion molecule for use according to any one of Embodiments 34 to 76 or 206 to 308 or the use according to any one of Embodiments 77 to 162 or 206 to 308 or the pharmaceutical composition according to any one of Embodiments 163 to 308, wherein said increased APRIL level in serum is increased by at least 25% compared to healthy individuals that do not have IgAN.

Embodiment 310. The method according to any one of Embodiments 1 to 33 or 206 to 309 or the TACI-Ig fusion molecule for use according to any one of Embodiments 34 to 76 or 206 to 309 or the use according to any one of Embodiments 77 to 162 or 206 to 309 or the pharmaceutical composition according to any one of Embodiments 163 to 309, wherein said increased APRIL level in serum is increased by at least 50% compared to healthy individuals that do not have IgAN.

Embodiment 311. The method according to any one of Embodiments 1 to 33 or 206 to 310 or the TACI-Ig fusion molecule for use according to any one of Embodiments 34 to 76 or 206 to 310 or the use according to any one of Embodiments 77 to 162 or 206 to 310 or the pharmaceutical composition according to any one of Embodiments 163 to 310, wherein said patient has increased BLyS and APRIL levels compared to healthy individuals that do not have IgAN.

Embodiment 312. The method according to any one of Embodiments 1 to 33 or 206 to 311 or the TACI-Ig fusion molecule for use according to any one of Embodiments 34 to 76 or 206 to 311 or the use according to any one of Embodiments 77 to 162 or 206 to 311 or the pharmaceutical composition according to any one of Embodiments 163 to 311, wherein said patient has been diagnosed to have increased BLyS and APRIL levels compared to healthy individuals that do not have IgAN.

Embodiment 313. The method according to any one of Embodiments 1 to 33 or 206 to 312 or the TACI-Ig fusion molecule for use according to any one of Embodiments 34 to 76 or 206 to 312 or the use according to any one of Embodiments 77 to 162 or 206 to 312 or the pharmaceutical composition according to any one of Embodiments 163 to 312, wherein said method comprises the step of determining the levels of the cytokines BLyS and APRIL in the serum of said patient.

Embodiment 314. The method according to any one of Embodiments 1 to 33 or 206 to 313 or the TACI-Ig fusion molecule for use according to any one of Embodiments 34 to 76 or 206 to 313 or the use according to any one of Embodiments 77 to 162 or 206 to 313 or the pharmaceutical composition according to any one of Embodiments 163 to 313, wherein said method comprises the step of determining the levels of the cytokines BLyS and APRIL in the serum of said patient, and wherein said patient is subjected to the administration of said TACI-Ig fusion molecule if said patient has increased BLyS and APRIL levels compared to healthy individuals that do not have IgAN.

Embodiment 315. The method according to any one of Embodiments 1 to 33 or 206 to 314 or the TACI-Ig fusion molecule for use according to any one of Embodiments 34 to 76 or 206 to 314 or the use according to any one of Embodiments 77 to 162 or 206 to 314 or the pharmaceutical composition according to any one of Embodiments 163 to 314, wherein said increased BLyS and APRIL level are each increased by at least 10% compared to healthy individuals that do not have IgAN.

Embodiment 316. The method according to any one of Embodiments 1 to 33 or 206 to 315 or the TACI-Ig fusion molecule for use according to any one of Embodiments 34 to 76 or 206 to 315 or the use according to any one of Embodiments 77 to 162 or 206 to 315 or the pharmaceutical composition according to any one of Embodiments 163 to 315, wherein said increased BLyS and APRIL level are each increased by at least 25% compared to healthy individuals that do not have IgAN.

Embodiment 317. The method according to any one of Embodiments 1 to 33 or 206 to 316 or the TACI-Ig fusion molecule for use according to any one of Embodiments 34 to 76 or 206 to 316 or the use according to any one of Embodiments 77 to 162 or 206 to 316 or the pharmaceutical composition according to any one of Embodiments 163 to 316, wherein said increased BLyS and APRIL level are each increased by at least 50% compared to healthy individuals that do not have IgAN.

Embodiment 318. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 0.2 to 10 mg of TACI-Ig fusion molecule per kg of body weight of said patient per week.

Embodiment 319. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 0.5 to 5 mg of TACI-Ig fusion molecule per kg of body weight of said patient per week.

Embodiment 320. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 0.5 to 2 mg of TACI-Ig fusion molecule per kg of body weight of said patient per week.

Embodiment 321. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 0.8 to 1.5 mg of TACI-Ig fusion molecule per kg of body weight of said patient per week.

Embodiment 322. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of about 25 to about 150 mg per week.

Embodiment 323. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of about 50 to about 150 mg per week.

Embodiment 324. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of about 75 to about 150 mg per week.

Embodiment 325. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of about 75 to about 125 mg per week.

Embodiment 326. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of about 75 mg per week.

Embodiment 327. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 25 to 150 mg per week.

Embodiment 328. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 50 to 150 mg per week.

Embodiment 329. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 75 to 150 mg per week.

Embodiment 330. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 75 mg per week.

Embodiment 331. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 75 to 125 mg per week.

Embodiment 332. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 70 to 155 mg per week.

Embodiment 333. The method according to any one of Embodiments 1 to 33 or 206 to 317 or the TACI-Ig fusion molecule for use according to any one of Embodiments 34 to 76 or 206 to 317 or the use according to any one of Embodiments 77 to 162 or 206 to 317 or the pharmaceutical composition according to any one of Embodiments 163 to 317, wherein said TACI-Ig fusion molecule is administered in an amount of 70 to 80 mg per week.

Embodiment 334. The method according to any one of Embodiments 1 to 33 or 206 to 333 or the TACI-Ig fusion molecule for use according to any one of Embodiments 34 to 76 or 206 to 333 or the use according to any one of Embodiments 77 to 162 or 206 to 333 or the pharmaceutical composition according to any one of Embodiments 163 to 333, wherein said TACI-Ig fusion molecule is administered in one to three weekly doses.

Embodiment 335. The method according to any one of Embodiments 1 to 33 or 206 to 333 or the TACI-Ig fusion molecule for use according to any one of Embodiments 34 to 76 or 206 to 333 or the use according to any one of Embodiments 77 to 162 or 206 to 333 or the pharmaceutical composition according to any one of Embodiments 163 to 333, wherein said TACI-Ig fusion molecule is administered in one or two weekly doses.

Embodiment 336. The method according to any one of Embodiments 1 to 33 or 206 to 333 or the TACI-Ig fusion molecule for use according to any one of Embodiments 34 to 76 or 206 to 333 or the use according to any one of Embodiments 77 to 162 or 206 to 333 or the pharmaceutical composition according to any one of Embodiments 163 to 333, wherein said TACI-Ig fusion molecule is administered in one weekly dose.

Embodiment 337. The method according to any one of Embodiments 1 to 33 or 206 to 333 or the TACI-Ig fusion molecule for use according to any one of Embodiments 34 to 76 or 206 to 333 or the use according to any one of Embodiments 77 to 162 or 206 to 333 or the pharmaceutical composition according to any one of Embodiments 163 to 333, wherein said TACI-Ig fusion molecule is administered in one dose every other week.

Embodiment 338. The method according to any one of Embodiments 1 to 33 or 206 to 337 or the TACI-Ig fusion molecule for use according to any one of Embodiments 34 to 76 or 206 to 337 or the use according to any one of Embodiments 77 to 162 or 206 to 337 or the pharmaceutical composition according to any one of Embodiments 163 to 337, wherein said TACI-Ig fusion molecule is administered for at least 4 weeks.

Embodiment 339. The method according to any one of Embodiments 1 to 33 or 206 to 337 or the TACI-Ig fusion molecule for use according to any one of Embodiments 34 to 76 or 206 to 337 or the use according to any one of Embodiments 77 to 162 or 206 to 337 or the pharmaceutical composition according to any one of Embodiments 163 to 337, wherein said TACI-Ig fusion molecule is administered for at least 8 weeks.

Embodiment 340. The method according to any one of Embodiments 1 to 33 or 206 to 337 or the TACI-Ig fusion molecule for use according to any one of Embodiments 34 to 162 or 206 to 337 or the use according to any one of Embodiments 77 to 251 or 206 to 337 or the pharmaceutical composition according to any one of Embodiments 163 to 337, wherein said TACI-Ig fusion molecule is administered for at least 12 weeks.

Embodiment 341. The method according to any one of Embodiments 1 to 33 or 206 to 337 or the TACI-Ig fusion molecule for use according to any one of Embodiments 34 to 76 or 206 to 337 or the use according to any one of Embodiments 77 to 162 or 206 to 337 or the pharmaceutical composition according to any one of Embodiments 163 to 337, wherein said TACI-Ig fusion molecule is administered for at least 24 weeks.

Embodiment 342. The method according to any one of Embodiments 1 to 33 or 206 to 337 or the TACI-Ig fusion molecule for use according to any one of Embodiments 34 to 76 or 206 to 337 or the use according to any one of Embodiments 77 to 162 or 206 to 337 or the pharmaceutical composition according to any one of Embodiments 163 to 337, wherein said TACI-Ig fusion molecule is administered for at least 48 weeks.

Embodiment 343. The method according to any one of Embodiments 1 to 33 or 206 to 337 or the TACI-Ig fusion molecule for use according to any one of Embodiments 34 to 76 or 206 to 337 or the use according to any one of Embodiments 77 to 162 or 206 to 337 or the pharmaceutical composition according to any one of Embodiments 163 to 337, wherein said TACI-Ig fusion molecule is administered for at least 52 weeks.

Embodiment 344. The method according to any one of Embodiments 1 to 33 or 206 to 338 or the TACI-Ig fusion molecule for use according to any one of Embodiments 34 to 76 or 206 to 338 or the use according to any one of Embodiments 77 to 162 or 206 to 338 or the pharmaceutical composition according to any one of Embodiments 163 to 252, wherein said TACI-Ig fusion molecule is administered for up to 4 weeks.

Embodiment 345. The method according to any one of Embodiments 1 to 33 or 206 to 339 or the TACI-Ig fusion molecule for use according to any one of Embodiments 34 to 76 or 206 to 339 or the use according to any one of Embodiments 77 to 162 or 206 to 339 or the pharmaceutical composition according to any one of Embodiments 163 to 339, wherein said TACI-Ig fusion molecule is administered for up to 8 weeks.

Embodiment 346. The method according to any one of Embodiments 1 to 33 or 206 to 340 or the TACI-Ig fusion molecule for use according to any one of Embodiments 34 to 76 or 206 to 340 or the use according to any one of Embodiments 77 to 162 or 206 to 340 or the pharmaceutical composition according to any one of Embodiments 163 to 340, wherein said TACI-Ig fusion molecule is administered for up to 12 weeks.

Embodiment 347. The method according to any one of Embodiments 1 to 33 or 206 to 341 or the TACI-Ig fusion molecule for use according to any one of Embodiments 34 to 76 or 206 to 341 or the use according to any one of Embodiments 77 to 162 or 206 to 341 or the pharmaceutical composition according to any one of Embodiments 163 to 341, wherein said TACI-Ig fusion molecule is administered for up to 24 weeks.

Embodiment 348. The method according to any one of Embodiments 1 to 33 or 206 to 342 or the TACI-Ig fusion molecule for use according to any one of Embodiments 34 to 76 or 206 to 342 or the use according to any one of Embodiments 77 to 162 or 206 to 342 or the pharmaceutical composition according to any one of Embodiments 163 to 342, wherein said TACI-Ig fusion molecule is administered for up to 48 weeks.

Embodiment 349. The method according to any one of Embodiments 1 to 33 or 206 to 343 or the TACI-Ig fusion molecule for use according to any one of Embodiments 34 to 76 or 206 to 343 or the use according to any one of Embodiments 77 to 162 or 206 to 343 or the pharmaceutical composition according to any one of Embodiments 163 to 343, wherein said TACI-Ig fusion molecule is administered for up to 52 weeks.

Embodiment 350. The method according to any one of Embodiments 1 to 33 or 206 to 343 or the TACI-Ig fusion molecule for use according to any one of Embodiments 34 to 76 or 206 to 343 or the use according to any one of Embodiments 77 to 162 or 206 to 343 or the pharmaceutical composition according to any one of Embodiments 163 to 343, wherein said TACI-Ig fusion molecule is administered for up to 72 weeks.

Embodiment 351. The method according to any one of Embodiments 1 to 33 or 206 to 343 or the TACI-Ig fusion molecule for use according to any one of Embodiments 34 to 76 or 206 to 343 or the use according to any one of Embodiments 77 to 162 or 206 to 343 or the pharmaceutical composition according to any one of Embodiments 163 to 343, wherein said TACI-Ig fusion molecule is administered for up to 156 weeks.

Embodiment 352. The method according to any one of Embodiments 1 to 33 or 206 to 337 or the TACI-Ig fusion molecule for use according to any one of Embodiments 34 to 76 or 206 to 337 or the use according to any one of Embodiments 77 to 162 or 206 to 337 or the pharmaceutical composition according to any one of Embodiments 163 to 337, wherein said TACI-Ig fusion molecule is administered for 2 to 48 weeks.

Embodiment 353. The method according to any one of Embodiments 1 to 33 or 206 to 337 or the TACI-Ig fusion molecule for use according to any one of Embodiments 34 to 76 or 206 to 337 or the use according to any one of Embodiments 77 to 162 or 206 to 337 or the pharmaceutical composition according to any one of Embodiments 163 to 337, wherein said TACI-Ig fusion molecule is administered for 2 to 52 weeks.

Embodiment 354. The method according to any one of Embodiments 1 to 33 or 206 to 353 or the TACI-Ig fusion molecule for use according to any one of Embodiments 34 to 76 or 206 to 353 or the use according to any one of Embodiments 77 to 162 or 206 to 353 or the pharmaceutical composition according to any one of Embodiments 163 to 353, wherein said TACI-Ig fusion molecule is administered by subcutaneous administration.

Embodiment 355. The method according to any one of Embodiments 1 to 33 or 206 to 354 or the TACI-Ig fusion molecule for use according to any one of Embodiments 34 to 76 or 206 to 354 or the use according to any one of Embodiments 77 to 162 or 206 to 354 or the pharmaceutical composition according to any one of Embodiments 163 to 354, wherein said TACI-Ig fusion molecule is administered in an aqueous solution containing (only) 60 to 100 mg/ml trehalose and an acetate buffer buffering the formulation at a pH ranging from 4.9-5.1.

Embodiment 356. The method according to any one of Embodiments 1 to 33 or 206 to 355 or the TACI-Ig fusion molecule for use according to any one of Embodiments 34 to 76 or 206 to 355 or the use according to any one of Embodiments 77 to 162 or 206 to 355 or the pharmaceutical composition according to any one of Embodiments 163 to 355, wherein said administration or said use of said TACI-Ig fusion molecule is by subcutaneous administration, wherein 25 mg of said TACI-Ig fusion molecule are administered per week in one dose per week.

Embodiment 357. The method according to any one of Embodiments 1 to 33 or 206 to 355 or the TACI-Ig fusion molecule for use according to any one of Embodiments 34 to 76 or 206 to 355 or the use according to any one of Embodiments 77 to 162 or 206 to 355 or the pharmaceutical composition according to any one of Embodiments 163 to 355, wherein said administration or said use of said TACI-Ig fusion molecule is by subcutaneous administration, wherein 75 mg of said TACI-Ig fusion molecule are administered per week in one dose per week.

Embodiment 358. The method according to any one of Embodiments 1 to 33 or 206 to 357 or the TACI-Ig fusion molecule for use according to any one of Embodiments 34 to 76 or 206 to 357 or the use according to any one of Embodiments 77 to 162 or 206 to 357 or the pharmaceutical composition according to any one of Embodiments 163 to 357, wherein concomitantly to said administration or said use of said TACI-Ig fusion molecule a further medicament is/further medicaments are administered to said patient.

Embodiment 359. The method according to any one of Embodiments 1 to 33 or 206 to 358 or the TACI-Ig fusion molecule for use according to any one of Embodiments 34 to 76 or 206 to 358 or the use according to any one of Embodiments 77 to 162 or 206 to 358 or the pharmaceutical composition according to any one of Embodiments 163 to 358, wherein said further medicament is/said further medicaments are selected from the group consisting of an angiotensin converting enzyme (ACE) inhibitor, an angiotensin receptor blocker (ARB), aspirin, an antihypertensive medication (preferably selected from the group consisting of a diuretic, an aldosterone antagonist, a calcium-channel blocker and a β-blocker), a statin, omega-3 fish oil and dipyridamole.

Embodiment 360. The method according to any one of Embodiments 1 to 33 or 206 to 359 or the TACI-Ig fusion molecule for use according to any one of Embodiments 34 to 76 or 206 to 359 or the use according to any one of Embodiments 77 to 162 or 206 to 359 or the pharmaceutical composition according to any one of Embodiments 163 to 359, wherein said further medicament(s) is an angiotensin converting enzyme (ACE) inhibitor or angiotensin receptor blocker (ARB) and/or a combination of an angiotensin converting enzyme (ACE) inhibitor and an angiotensin receptor blocker (ARB).

Embodiment 361. The method according to any one of Embodiments 1 to 33 or 206 to 360 or the TACI-Ig fusion molecule for use according to any one of Embodiments 34 to 76 or 206 to 360 or the use according to any one of Embodiments 77 to 162 or 206 to 360 or the pharmaceutical composition according to any one of Embodiments 163 to 360, wherein said further medicaments is a combination of an angiotensin converting enzyme (ACE) inhibitor and an angiotensin receptor blocker (ARB).

Embodiment 362. The method according to any one of Embodiments 1 to 33 or 206 to 361 or the TACI-Ig fusion molecule for use according to any one of Embodiments 34 to 76 or 206 to 361 or the use according to any one of Embodiments 77 to 162 or 206 to 361 or the pharmaceutical composition according to any one of Embodiments 163 to 361, wherein said treatment/said administration or said use of said TACI-Ig fusion molecule results in a reduction in the total protein in the urine of said patient (based on 24-hour urine collection) compared to the situation before said treatment/said administration or said use of said TACI-Ig fusion molecule.

Embodiment 363. The method according to any one of Embodiments 1 to 33 or 206 to 362 or the TACI-Ig fusion molecule for use according to any one of Embodiments 34 to 76 or 206 to 362 or the use according to any one of Embodiments 77 to 162 or 206 to 362 or the pharmaceutical composition according to any one of Embodiments 163 to 362, wherein said treatment/said administration or said use of said TACI-Ig fusion molecule results in a reduction in the total protein in the urine of said patient (based on 24-hour urine collection) by at least 10% compared to the situation before said treatment/said administration or said use of said TACI-Ig fusion molecule.

Embodiment 364. The method according to any one of Embodiments 1 to 33 or 206 to 363 or the TACI-Ig fusion molecule for use according to any one of Embodiments 34 to 76 or 206 to 363 or the use according to any one of Embodiments 77 to 162 or 206 to 363 or the pharmaceutical composition according to any one of Embodiments 163 to 363, wherein said treatment/said administration or said use of said TACI-Ig fusion molecule results in a reduction in the total protein in the urine of said patient (based on 24-hour urine collection) by at least 15% compared to the situation before said treatment/said administration or said use of said TACI-Ig fusion molecule.

Embodiment 365. The method according to any one of Embodiments 1 to 33 or 206 to 364 or the TACI-Ig fusion molecule for use according to any one of Embodiments 34 to 76 or 206 to 364 or the use according to any one of Embodiments 77 to 162 or 206 to 364 or the pharmaceutical composition according to any one of Embodiments 163 to 364, wherein said treatment/said administration or said use of said TACI-Ig fusion molecule results in a reduction in the total protein in the urine of said patient (based on 24-hour urine collection) by at least 20% compared to the situation before said treatment/said administration or said use of said TACI-Ig fusion molecule.

Embodiment 366. The method according to any one of Embodiments 1 to 33 or 206 to 365 or the TACI-Ig fusion molecule for use according to any one of Embodiments 34 to 76 or 206 to 365 or the use according to any one of Embodiments 77 to 162 or 206 to 365 or the pharmaceutical composition according to any one of Embodiments 163 to 365, wherein said treatment/said administration or said use of said TACI-Ig fusion molecule results in a reduction in the total protein in the urine of said patient (based on 24-hour urine collection) by at least 25% compared to the situation before said treatment/said administration or said use of said TACI-Ig fusion molecule.

Embodiment 367. The method according to any one of Embodiments 1 to 33 or 206 to 366 or the TACI-Ig fusion molecule for use according to any one of Embodiments 34 to 76 or 206 to 366 or the use according to any one of Embodiments 77 to 162 or 206 to 366 or the pharmaceutical composition according to any one of Embodiments 163 to 366, wherein said treatment/said administration or said use of said TACI-Ig fusion molecule results in a reduction in the urine-protein creatinine ratio (UPCR), based on 24-hour urine collection, compared to the situation before said treatment/said administration or said use of said TACI-Ig fusion molecule.

Embodiment 368. The method according to any one of Embodiments 1 to 33 or 206 to 367 or the TACI-Ig fusion molecule for use according to any one of Embodiments 34 to 76 or 206 to 367 or the use according to any one of Embodiments 77 to 162 or 206 to 367 or the pharmaceutical composition according to any one of Embodiments 163 to 367, wherein said treatment/said administration or said use of said TACI-Ig fusion molecule results in a reduction in the 24-hour urine-protein creatinine ratio (UPCR) of at least 10%, based on 24-hour urine collection, compared to the situation before said treatment/said administration or said use of said TACI-Ig fusion molecule.

Embodiment 369. The method according to any one of Embodiments 1 to 33 or 206 to 368 or the TACI-Ig fusion molecule for use according to any one of Embodiments 34 to 76 or 206 to 368 or the use according to any one of Embodiments 77 to 162 or 206 to 368 or the pharmaceutical composition according to any one of Embodiments 163 to 368, wherein said treatment/said administration or said use of said TACI-Ig fusion molecule results in a reduction in the 24-hour urine-protein creatinine ratio (UPCR) of at least 15%, based on 24-hour urine collection, compared to the situation before said treatment/said administration or said use of said TACI-Ig fusion molecule.

Embodiment 370. The method according to any one of Embodiments 1 to 33 or 206 to 369 or the TACI-Ig fusion molecule for use according to any one of Embodiments 34 to 76 or 206 to 369 or the use according to any one of Embodiments 77 to 162 or 206 to 369 or the pharmaceutical composition according to any one of Embodiments 163 to 369, wherein said treatment/said administration or said use of said TACI-Ig fusion molecule results in a reduction in the 24-hour urine-protein creatinine ratio (UPCR) of at least 20%, based on 24-hour urine collection, compared to the situation before said treatment/said administration or said use of said TACI-Ig fusion molecule.

Embodiment 371. The method according to any one of Embodiments 1 to 33 or 206 to 370 or the TACI-Ig fusion molecule for use according to any one of Embodiments 34 to 76 or 206 to 370 or the use according to any one of Embodiments 77 to 162 or 206 to 370 or the pharmaceutical composition according to any one of Embodiments 163 to 370, wherein said treatment/said administration or said use of said TACI-Ig fusion molecule results in a reduction in the 24-hour urine-protein creatinine ratio (UPCR) of at least 25%, based on 24-hour urine collection, compared to the situation before said treatment/said administration or said use of said TACI-Ig fusion molecule.

Embodiment 372. The method according to any one of Embodiments 1 to 33 or 206 to 371 or the TACI-Ig fusion molecule for use according to any one of Embodiments 34 to 76 or 206 to 371 or the use according to any one of Embodiments 77 to 162 or 206 to 371 or the pharmaceutical composition according to any one of Embodiments 163 to 371, wherein said treatment/said administration or said use of said TACI-Ig fusion molecule results in a reduction in the 24-hour urine-protein creatinine ratio (UPCR) of at least 30%, based on 24-hour urine collection, compared to the situation before said treatment/said administration or said use of said TACI-Ig fusion molecule.

Embodiment 373. The method according to any one of Embodiments 1 to 33 or 206 to 372 or the TACI-Ig fusion molecule for use according to any one of Embodiments 34 to 76 or 206 to 372 or the use according to any one of Embodiments 77 to 162 or 206 to 372 or the pharmaceutical composition according to any one of Embodiments 163 to 372, wherein during said treatment/said administration or said use of said TACI-Ig fusion molecule the Estimated Glomerular Filtration Rate (eGFR) is decreased by not more than 10%.

Embodiment 374. The method according to any one of Embodiments 1 to 33 or 206 to 372 or the TACI-Ig fusion molecule for use according to any one of Embodiments 34 to 76 or 206 to 372 or the use according to any one of Embodiments 77 to 162 or 206 to 372 or the pharmaceutical composition according to any one of Embodiments 163 to 372, wherein during said treatment/said administration or said use of said TACI-Ig fusion molecule the Estimated Glomerular Filtration Rate (eGFR) is decreased by not more than 5%.

Embodiment 375. The method according to any one of Embodiments 1 to 33 or 206 to 372 or the TACI-Ig fusion molecule for use according to any one of Embodiments 34 to 76 or 206 to 372 or the use according to any one of Embodiments 77 to 162 or 206 to 372 or the pharmaceutical composition according to any one of Embodiments 163 to 372, wherein during said treatment/said administration or said use of said TACI-Ig fusion molecule the Estimated Glomerular Filtration Rate (eGFR) is not decreased.

Embodiment 376. The method according to any one of Embodiments 1 to 33 or 206 to 372 or the TACI-Ig fusion molecule for use according to any one of Embodiments 34 to 76 or 206 to 372 or the use according to any one of Embodiments 77 to 162 or 206 to 372 or the pharmaceutical composition according to any one of Embodiments 163 to 372, wherein during said treatment/said administration or said use of said TACI-Ig fusion molecule the Estimated Glomerular Filtration Rate (eGFR) is increased.

Embodiment 377. The method according to any one of Embodiments 1 to 33 or 206 to 372 or the TACI-Ig fusion molecule for use according to any one of Embodiments 34 to 76 or 206 to 372 or the use according to any one of Embodiments 77 to 162 or 206 to 372 or the pharmaceutical composition according to any one of Embodiments 163 to 372, wherein during said treatment/said administration or said use of said TACI-Ig fusion molecule the Estimated Glomerular Filtration Rate (eGFR) is increased by at least 5%.

Embodiment 378. The method according to any one of Embodiments 1 to 33 or 206 to 372 or the TACI-Ig fusion molecule for use according to any one of Embodiments 34 to 76 or 206 to 372 or the use according to any one of Embodiments 77 to 162 or 206 to 372 or the pharmaceutical composition according to any one of Embodiments 163 to 372, wherein during said treatment/said administration or said use of said TACI-Ig fusion molecule the Estimated Glomerular Filtration Rate (eGFR) is increased by at least 10%.

Embodiment 379. The method according to any one of Embodiments 1 to 33 or 206 to 378 or the TACI-Ig fusion molecule for use according to any one of Embodiments 34 to 76 or 206 to 378 or the use according to any one of Embodiments 77 to 162 or 206 to 378 or the pharmaceutical composition according to any one of Embodiments 163 to 378, wherein said treatment/said administration or said use of said TACI-Ig fusion molecule results in a reduction in the number of mature naive B cells in peripheral blood compared to the situation before said treatment/said administration or said use of said TACI-Ig fusion molecule.

Embodiment 380. The method according to any one of Embodiments 1 to 33 or 206 to 379 or the TACI-Ig fusion molecule for use according to any one of Embodiments 34 to 76 or 206 to 379 or the use according to any one of Embodiments 77 to 162 or 206 to 379 or the pharmaceutical composition according to any one of Embodiments 163 to 379, wherein said treatment/said administration or said use of said TACI-Ig fusion molecule results in a reduction in the number of mature naive B cells in peripheral blood by at least 10% compared to the situation before said treatment/said administration or said use of said TACI-Ig fusion molecule.

Embodiment 381. The method according to any one of Embodiments 1 to 33 or 206 to 380 or the TACI-Ig fusion molecule for use according to any one of Embodiments 34 to 76 or 206 to 380 or the use according to any one of Embodiments 77 to 162 or 206 to 380 or the pharmaceutical composition according to any one of Embodiments 163 to 380, wherein said treatment/said administration or said use of said TACI-Ig fusion molecule results in a reduction in the number of mature naive B cells in peripheral blood by at least 20% compared to the situation before said treatment/said administration or said use of said TACI-Ig fusion molecule.

Embodiment 382. The method according to any one of Embodiments 1 to 33 or 206 to 381 or the TACI-Ig fusion molecule for use according to any one of Embodiments 34 to 76 or 206 to 381 or the use according to any one of Embodiments 77 to 162 or 206 to 381 or the pharmaceutical composition according to any one of Embodiments 163 to 381, wherein said treatment/said administration or said use of said TACI-Ig fusion molecule results in a reduction in the number of mature naive B cells in peripheral blood by at least 25% compared to the situation before said treatment/said administration or said use of said TACI-Ig fusion molecule.

Embodiment 383. The method according to any one of Embodiments 1 to 33 or 206 to 382 or the TACI-Ig fusion molecule for use according to any one of Embodiments 34 to 76 or 206 to 382 or the use according to any one of Embodiments 77 to 162 or 206 to 382 or the pharmaceutical composition according to any one of Embodiments 163 to 382, wherein said treatment/said administration or said use of said TACI-Ig fusion molecule results in a reduction in the number of mature naive B cells in peripheral blood by at least 30% compared to the situation before said treatment/said administration or said use of said TACI-Ig fusion molecule.

Embodiment 384. The method according to any one of Embodiments 1 to 33 or 206 to 383 or the TACI-Ig fusion molecule for use according to any one of Embodiments 34 to 76 or 206 to 383 or the use according to any one of Embodiments 77 to 162 or 206 to 383 or the pharmaceutical composition according to any one of Embodiments 163 to 383, wherein said treatment/said administration or said use of said TACI-Ig fusion molecule results in a reduction in the number of mature naive B cells in peripheral blood by at least 40% compared to the situation before said treatment/said administration or said use of said TACI-Ig fusion molecule.

Embodiment 385. The method according to any one of Embodiments 1 to 33 or 206 to 384 or the TACI-Ig fusion molecule for use according to any one of Embodiments 34 to 76 or 206 to 384 or the use according to any one of Embodiments 77 to 162 or 206 to 384 or the pharmaceutical composition according to any one of Embodiments 163 to 384, wherein said treatment/said administration or said use of said TACI-Ig fusion molecule results in a reduction in the number of mature naive B cells in peripheral blood by at least 50% compared to the situation before said treatment/said administration or said use of said TACI-Ig fusion molecule.

Embodiment 386. The method according to any one of Embodiments 1 to 33 or 206 to 385 or the TACI-Ig fusion molecule for use according to any one of Embodiments 34 to 76 or 206 to 385 or the use according to any one of Embodiments 77 to 162 or 206 to 385 or the pharmaceutical composition according to any one of Embodiments 163 to 385, wherein said treatment/said administration or said use of said TACI-Ig fusion molecule results in a reduction in the serum level of Gd-IgA1 antibodies compared to the situation before said treatment/said administration or said use of said TACI-Ig fusion molecule.

Embodiment 387. The method according to any one of Embodiments 1 to 33 or 206 to 386 or the TACI-Ig fusion molecule for use according to any one of Embodiments 34 to 76 or 206 to 386 or the use according to any one of Embodiments 77 to 162 or 206 to 386 or the pharmaceutical composition according to any one of Embodiments 163 to 386, wherein said treatment/said administration or said use of said TACI-Ig fusion molecule results in a reduction in the serum level of Gd-IgA1 antibodies compared to the situation before said treatment/said administration or said use of said TACI-Ig fusion molecule by at least 10%.

Embodiment 388. The method according to any one of Embodiments 1 to 33 or 206 to 387 or the TACI-Ig fusion molecule for use according to any one of Embodiments 34 to 76 or 206 to 387 or the use according to any one of Embodiments 77 to 162 or 206 to 387 or the pharmaceutical composition according to any one of Embodiments 163 to 387, wherein said treatment/said administration or said use of said TACI-Ig fusion molecule results in a reduction in the serum level of Gd-IgA1 antibodies compared to the situation before said treatment/said administration or said use of said TACI-Ig fusion molecule by at least 20%.

Embodiment 389. The method according to any one of Embodiments 1 to 33 or 206 to 388 or the TACI-Ig fusion molecule for use according to any one of Embodiments 34 to 76 or 206 to 388 or the use according to any one of Embodiments 77 to 162 or 206 to 388 or the pharmaceutical composition according to any one of Embodiments 163 to 388, wherein said treatment/said administration or said use of said TACI-Ig fusion molecule results in a reduction in the serum level of Gd-IgA1 antibodies compared to the situation before said treatment/said administration or said use of said TACI-Ig fusion molecule by at least 25%.

Embodiment 390. The method according to any one of Embodiments 1 to 33 or 206 to 389 or the TACI-Ig fusion molecule for use according to any one of Embodiments 34 to 76 or 206 to 389 or the use according to any one of Embodiments 77 to 162 or 206 to 389 or the pharmaceutical composition according to any one of Embodiments 163 to 389, wherein said treatment/said administration or said use of said TACI-Ig fusion molecule results in a reduction in the serum level of Gd-IgA1 antibodies compared to the situation before said treatment/said administration or said use of said TACI-Ig fusion molecule by at least 30%.

Embodiment 391. The method according to any one of Embodiments 1 to 33 or 206 to 390 or the TACI-Ig fusion molecule for use according to any one of Embodiments 34 to 76 or 206 to 390 or the use according to any one of Embodiments 77 to 162 or 206 to 390 or the pharmaceutical composition according to any one of Embodiments 163 to 390, wherein said treatment/said administration or said use of said TACI-Ig fusion molecule results in a reduction in the serum level of Gd-IgA1 antibodies compared to the situation before said treatment/said administration or said use of said TACI-Ig fusion molecule by at least 40%.

Embodiment 392. The method according to any one of Embodiments 1 to 33 or 206 to 391 or the TACI-Ig fusion molecule for use according to any one of Embodiments 34 to 76 or 206 to 391 or the use according to any one of Embodiments 77 to 162 or 206 to 391 or the pharmaceutical composition according to any one of Embodiments 163 to 391, wherein said treatment/said administration or said use of said TACI-Ig fusion molecule results in a reduction in the serum level of Gd-IgA1 antibodies compared to the situation before said treatment/said administration or said use of said TACI-Ig fusion molecule by at least 50%.

Embodiment 393. The method according to any one of Embodiments 1 to 33 or 206 to 392 or the TACI-Ig fusion molecule for use according to any one of Embodiments 34 to 76 or 206 to 392 or the use according to any one of Embodiments 77 to 162 or 206 to 392 or the pharmaceutical composition according to any one of Embodiments 163 to 392, wherein said treatment/said administration or said use of said TACI-Ig fusion molecule results in a reduction in the serum level of Gd-IgA1 antibodies compared to the situation before said treatment/said administration or said use of said TACI-Ig fusion molecule by at least 60%.

Embodiment 394. The method according to any one of Embodiments 1 to 33 or 206 to 393 or the TACI-Ig fusion molecule for use according to any one of Embodiments 34 to 76 or 206 to 393 or the use according to any one of Embodiments 77 to 162 or 206 to 393 or the pharmaceutical composition according to any one of Embodiments 163 to 393, wherein said treatment/said administration or said use of said TACI-Ig fusion molecule results in a decrease in the serum concentration of IgA compared to the situation before said treatment/said administration or said use of said TACI-Ig fusion molecule.

Embodiment 395. The method according to any one of Embodiments 1 to 33 or 206 to 394 or the TACI-Ig fusion molecule for use according to any one of Embodiments 34 to 76 or 206 to 394 or the use according to any one of Embodiments 77 to 162 or 206 to 394 or the pharmaceutical composition according to any one of Embodiments 163 to 394, wherein said treatment/said administration or said use of said TACI-Ig fusion molecule results in a decrease in the serum concentration of IgA by at least 10% compared to the situation before said treatment/said administration or said use of said TACI-Ig fusion molecule.

Embodiment 396. The method according to any one of Embodiments 1 to 33 or 206 to 395 or the TACI-Ig fusion molecule for use according to any one of Embodiments 34 to 76 or 206 to 395 or the use according to any one of Embodiments 77 to 162 or 206 to 395 or the pharmaceutical composition according to any one of Embodiments 163 to 395, wherein said treatment/said administration or said use of said TACI-Ig fusion molecule results in a decrease in the serum concentration of IgA by at least 20% compared to the situation before said treatment/said administration or said use of said TACI-Ig fusion molecule.

Embodiment 397. The method according to any one of Embodiments 1 to 33 or 206 to 396 or the TACI-Ig fusion molecule for use according to any one of Embodiments 34 to 76 or 206 to 396 or the use according to any one of Embodiments 77 to 162 or 206 to 396 or the pharmaceutical composition according to any one of Embodiments 163 to 396, wherein said treatment/said administration or said use of said TACI-Ig fusion molecule results in a decrease in the serum concentration of IgA by at least 30% compared to the situation before said treatment/said administration or said use of said TACI-Ig fusion molecule.

Embodiment 398. The method according to any one of Embodiments 1 to 33 or 206 to 397 or the TACI-Ig fusion molecule for use according to any one of Embodiments 34 to 76 or 206 to 397 or the use according to any one of Embodiments 77 to 162 or 206 to 397 or the pharmaceutical composition according to any one of Embodiments 163 to 397, wherein said treatment/said administration or said use of said TACI-Ig fusion molecule results in a decrease in the serum concentration of IgA by at least 40% compared to the situation before said treatment/said administration or said use of said TACI-Ig fusion molecule.

Embodiment 399. The method according to any one of Embodiments 1 to 33 or 206 to 398 or the TACI-Ig fusion molecule for use according to any one of Embodiments 34 to 76 or 206 to 398 or the use according to any one of Embodiments 77 to 162 or 206 to 398 or the pharmaceutical composition according to any one of Embodiments 163 to 398, wherein said treatment/said administration or said use of said TACI-Ig fusion molecule results in a decrease in the serum concentration of IgA by at least 50% compared to the situation before said treatment/said administration or said use of said TACI-Ig fusion molecule.

Embodiment 400. The method according to any one of Embodiments 1 to 33 or 206 to 399 or the TACI-Ig fusion molecule for use according to any one of Embodiments 34 to 76 or 206 to 399 or the use according to any one of Embodiments 77 to 162 or 206 to 399 or the pharmaceutical composition according to any one of Embodiments 163 to 399, wherein said treatment/said administration or said use of said TACI-Ig fusion molecule results in a decrease in the serum concentration of IgG compared to the situation before said treatment/said administration or said use of said TACI-Ig fusion molecule.

Embodiment 401. The method according to any one of Embodiments 1 to 33 or 206 to 400 or the TACI-Ig fusion molecule for use according to any one of Embodiments 34 to 76 or 206 to 400 or the use according to any one of Embodiments 77 to 162 or 206 to 400 or the pharmaceutical composition according to any one of Embodiments 163 to 400, wherein said treatment/said administration or said use of said TACI-Ig fusion molecule results in a decrease in the serum concentration of IgG by at least 10% compared to the situation before said treatment/said administration or said use of said TACI-Ig fusion molecule.

Embodiment 402. The method according to any one of Embodiments 1 to 33 or 206 to 401 or the TACI-Ig fusion molecule for use according to any one of Embodiments 34 to 76 or 206 to 401 or the use according to any one of Embodiments 77 to 162 or 206 to 401 or the pharmaceutical composition according to any one of Embodiments 163 to 401, wherein said treatment/said administration or said use of said TACI-Ig fusion molecule results in a decrease in the serum concentration of IgG by at least 20% compared to the situation before said treatment/said administration or said use of said TACI-Ig fusion molecule.

Embodiment 403. The method according to any one of Embodiments 1 to 33 or 206 to 402 or the TACI-Ig fusion molecule for use according to any one of Embodiments 34 to 76 or 206 to 402 or the use according to any one of Embodiments 77 to 162 or 206 to 402 or the pharmaceutical composition according to any one of Embodiments 163 to 402, wherein said treatment/said administration or said use of said TACI-Ig fusion molecule results in a decrease in the serum concentration of IgG by at least 30% compared to the situation before said treatment/said administration or said use of said TACI-Ig fusion molecule.

Embodiment 404. The method according to any one of Embodiments 1 to 33 or 206 to 403 or the TACI-Ig fusion molecule for use according to any one of Embodiments 34 to 76 or 206 to 403 or the use according to any one of Embodiments 77 to 162 or 206 to 403 or the pharmaceutical composition according to any one of Embodiments 163 to 403, wherein said treatment/said administration or said use of said TACI-Ig fusion molecule results in a decrease in the serum concentration of IgM compared to the situation before said treatment/said administration or said use of said TACI-Ig fusion molecule.

Embodiment 405. The method according to any one of Embodiments 1 to 33 or 206 to 404 or the TACI-Ig fusion molecule for use according to any one of Embodiments 34 to 76 or 206 to 404 or the use according to any one of Embodiments 77 to 162 or 206 to 404 or the pharmaceutical composition according to any one of Embodiments 163 to 404, wherein said treatment/said administration or said use of said TACI-Ig fusion molecule results in a decrease in the serum concentration of IgM by at least 10% compared to the situation before said treatment/said administration or said use of said TACI-Ig fusion molecule.

Embodiment 406. The method according to any one of Embodiments 1 to 33 or 206 to 405 or the TACI-Ig fusion molecule for use according to any one of Embodiments 34 to 76 or 206 to 405 or the use according to any one of Embodiments 77 to 162 or 206 to 405 or the pharmaceutical composition according to any one of Embodiments 163 to 405, wherein said treatment/said administration or said use of said TACI-Ig fusion molecule results in a decrease in the serum concentration of IgM by at least 20% compared to the situation before said treatment/said administration or said use of said TACI-Ig fusion molecule.

Embodiment 407. The method according to any one of Embodiments 1 to 33 or 206 to 406 or the TACI-Ig fusion molecule for use according to any one of Embodiments 34 to 76 or 206 to 406 or the use according to any one of Embodiments 77 to 162 or 206 to 406 or the pharmaceutical composition according to any one of Embodiments 163 to 406, wherein said treatment/said administration or said use of said TACI-Ig fusion molecule results in a decrease in the serum concentration of IgM by at least 30% compared to the situation before said treatment/said administration or said use of said TACI-Ig fusion molecule.

Embodiment 408. The method according to any one of Embodiments 1 to 33 or 206 to 407 or the TACI-Ig fusion molecule for use according to any one of Embodiments 34 to 76 or 206 to 407 or the use according to any one of Embodiments 77 to 162 or 206 to 407 or the pharmaceutical composition according to any one of Embodiments 163 to 407, wherein said treatment/said administration or said use of said TACI-Ig fusion molecule results in a decrease in the serum concentration of IgM by at least 40% compared to the situation before said treatment/said administration or said use of said TACI-Ig fusion molecule.

Embodiment 409. The method according to any one of Embodiments 1 to 33 or 206 to 408 or the TACI-Ig fusion molecule for use according to any one of Embodiments 34 to 76 or 206 to 408 or the use according to any one of Embodiments 77 to 162 or 206 to 408 or the pharmaceutical composition according to any one of Embodiments 163 to 408, wherein said treatment/said administration or said use of said TACI-Ig fusion molecule results in a decrease in the serum concentration of IgM by at least 50% compared to the situation before said treatment/said administration or said use of said TACI-Ig fusion molecule.

Embodiment 410. The method according to any one of Embodiments 1 to 33 or 206 to 409 or the TACI-Ig fusion molecule for use according to any one of Embodiments 34 to 76 or 206 to 409 or the use according to any one of Embodiments 77 to 162 or 206 to 409 or the pharmaceutical composition according to any one of Embodiments 163 to 409, wherein said treatment/said administration or said use of said TACI-Ig fusion molecule results in a decrease in the serum concentration of IgM by at least 60% compared to the situation before said treatment/said administration or said use of said TACI-Ig fusion molecule.

Embodiment 411. The method according to any one of Embodiments 1 to 33 or 206 to 410 or the TACI-Ig fusion molecule for use according to any one of Embodiments 34 to 76 or 206 to 410 or the use according to any one of Embodiments 77 to 162 or 206 to 410 or the pharmaceutical composition according to any one of Embodiments 163 to 410, wherein said treatment/said administration or said use of said TACI-Ig fusion molecule results in a decrease in the serum concentration of IgM by at least 70% compared to the situation before said treatment/said administration or said use of said TACI-Ig fusion molecule.

Embodiment 412. The method according to any one of Embodiments 1 to 33 or 206 to 411 or the TACI-Ig fusion molecule for use according to any one of Embodiments 34 to 76 or 206 to 411 or the use according to any one of Embodiments 77 to 162 or 206 to 411 or the pharmaceutical composition according to any one of Embodiments 163 to 411, wherein said treatment/said administration or said use of said TACI-Ig fusion molecule results in a decrease in the serum concentration of each of IgA, IgG, and IgM compared to the situation before said treatment/said administration or said use of said TACI-Ig fusion molecule.

Embodiment 413. The method according to any one of Embodiments 1 to 33 or 206 to 412 or the TACI-Ig fusion molecule for use according to any one of Embodiments 34 to 76 or 206 to 412 or the use according to any one of Embodiments 77 to 162 or 206 to 412 or the pharmaceutical composition according to any one of Embodiments 163 to 412, wherein said treatment/said administration or said use of said TACI-Ig fusion molecule results in a decrease in the serum concentration of each of IgA, IgG, and IgM by at least 10% compared to the situation before said treatment/said administration or said use of said TACI-Ig fusion molecule.

Embodiment 414. The method according to any one of Embodiments 1 to 33 or 206 to 413 or the TACI-Ig fusion molecule for use according to any one of Embodiments 34 to 76 or 206 to 413 or the use according to any one of Embodiments 77 to 162 or 206 to 413 or the pharmaceutical composition according to any one of Embodiments 163 to 413, wherein said treatment/said administration or said use of said TACI-Ig fusion molecule results in a decrease in the serum concentration of each of IgA, IgG, and IgM by at least 20% compared to the situation before said treatment/said administration or said use of said TACI-Ig fusion molecule.

Embodiment 415. The method according to any one of Embodiments 1 to 33 or 206 to 414 or the TACI-Ig fusion molecule for use according to any one of Embodiments 34 to 76 or 206 to 414 or the use according to any one of Embodiments 77 to 162 or 206 to 414 or the pharmaceutical composition according to any one of Embodiments 163 to 414, wherein said treatment/said administration or said use of said TACI-Ig fusion molecule results in a decrease in the serum concentration of each of IgA, IgG, and IgM by at least 30% compared to the situation before said treatment/said administration or said use of said TACI-Ig fusion molecule.

Embodiment 416. The method according to any one of Embodiments 1 to 33 or 206 to 415 or the TACI-Ig fusion molecule for use according to any one of Embodiments 34 to 76 or 206 to 415 or the use according to any one of Embodiments 77 to 162 or 206 to 415 or the pharmaceutical composition according to any one of Embodiments 163 to 415, wherein said treatment/said administration or said use of said TACI-Ig fusion molecule results in a reduction in the serum level of anti-Gd-IgA1 antibodies compared to the situation before said treatment/said administration or said use of said TACI-Ig fusion molecule.

Embodiment 417. The method according to any one of Embodiments 1 to 33 or 206 to 416 or the TACI-Ig fusion molecule for use according to any one of Embodiments 34 to 76 or 206 to 416 or the use according to any one of Embodiments 77 to 162 or 206 to 416 or the pharmaceutical composition according to any one of Embodiments 163 to 416, wherein said treatment/said administration or said use of said TACI-Ig fusion molecule results in a reduction in glomerular IgA deposition compared to the situation before said treatment/said administration or said use of said TACI-Ig fusion molecule.

Embodiment 418. The method according to any one of Embodiments 1 to 33 or 206 to 417 or the TACI-Ig fusion molecule for use according to any one of Embodiments 34 to 76 or 206 to 417 or the use according to any one of Embodiments 77 to 162 or 206 to 417 or the pharmaceutical composition according to any one of Embodiments 163 to 417, wherein said treatment/said administration or said use of said TACI-Ig fusion molecule results in a reduction in glomerular IgA deposition compared to the situation before said treatment/said administration or said use of said TACI-Ig fusion molecule.

Embodiment 419. The method according to any one of Embodiments 1 to 33 or 206 to 418 or the TACI-Ig fusion molecule for use according to any one of Embodiments 34 to 76 or 206 to 418 or the use according to any one of Embodiments 77 to 162 or 206 to 418 or the pharmaceutical composition according to any one of Embodiments 163 to 418, wherein said treatment/said administration or said use of said TACI-Ig fusion molecule results in a decrease in renal histopathology compared to the situation before said treatment/said administration or said use of said TACI-Ig fusion molecule.

Embodiment 420. The method according to any one of Embodiments 1 to 33 or 206 to 419 or the TACI-Ig fusion molecule for use according to any one of Embodiments 34 to 76 or 206 to 419 or the use according to any one of Embodiments 77 to 162 or 206 to 419 or the pharmaceutical composition according to any one of Embodiments 163 to 419, wherein no decrease in the serum level of complement C3 is observed during said treatment/said administration or said use of said TACI-Ig fusion molecule.

Embodiment 421. The method according to any one of Embodiments 1 to 33 or 206 to 420 or the TACI-Ig fusion molecule for use according to any one of Embodiments 34 to 76 or 206 to 420 or the use according to any one of Embodiments 77 to 162 or 206 to 420 or the pharmaceutical composition according to any one of Embodiments 163 to 420, wherein said treatment/said administration or said use of said TACI-Ig fusion molecule results in an increase in the serum level of complement C3 compared to the situation before said treatment/said administration or said use of said TACI-Ig fusion molecule.

Embodiment 422. The method according to any one of Embodiments 1 to 33 or 206 to 421 or the TACI-Ig fusion molecule for use according to any one of Embodiments 34 to 76 or 206 to 421 or the use according to any one of Embodiments 77 to 162 or 206 to 421 or the pharmaceutical composition according to any one of Embodiments 163 to 421, wherein no decrease in the serum level of complement C4 is observed during said treatment/said administration or said use of said TACI-Ig fusion molecule.

Embodiment 423. The method according to any one of Embodiments 1 to 33 or 206 to 422 or the TACI-Ig fusion molecule for use according to any one of Embodiments 34 to 76 or 206 to 422 or the use according to any one of Embodiments 77 to 162 or 206 to 422 or the pharmaceutical composition according to any one of Embodiments 163 to 422, wherein said treatment/said administration or said use of said TACI-Ig fusion molecule results in an increase in the serum level of complement C4 compared to the situation before said treatment/said administration or said use of said TACI-Ig fusion molecule.

Embodiment II-1. A method for treating a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-2. A method for reducing the serum Gd-IgA1 level in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-3. A method for reducing the proteinuria in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-4. A method for reducing the serum Gd-IgA1 level and the proteinuria in a patient having IgA nephropathy (IgAN), said method comprising administering to the patient a transmembrane activator and calcium modulator and cyclophilin ligand-interactor (TACI)-immunoglobulin (Ig) fusion molecule, wherein said TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-5. The method according to any one of Embodiments II-1 to 11-4, wherein said patient has persistent proteinuria.

Embodiment 11-6. The method according to any one of Embodiments II-1 to 11-5, wherein said proteinuria is a persistent proteinuria of 1.0 to 6.0 g/day (total protein based on 24-hour urine collection).

Embodiment 11-7. The method according to Embodiment II-5 or 11-6, wherein (a) said persistent proteinuria is a persistent proteinuria with UPCR≥1 mg/mg based on 24-hour urine collection or (b) said persistent proteinuria is a persistent proteinuria with UPCR≥0.75 mg/mg based on 24-hour urine collection, wherein at least once within 12 months prior to said administration or said use of said TACI-Ig fusion molecule said patient has been determined to have a UPCR≥1 mg/mg based on 24-hour urine collection.

Embodiment 11-8. The method according to any one of Embodiments II-1 to 11-7, wherein said TACI-Ig fusion molecule has an amino acid sequence that is at least 80% identical to SEQ ID NO: 3.

Embodiment 11-9. The method according to any one of Embodiments II-1 to 11-8, wherein said TACI-Ig fusion molecule is atacicept.

Embodiment II-10. The method according to any one of Embodiments II-1 to 11-9, wherein said patient has been treated with an angiotensin converting enzyme (ACE)

inhibitor and/or angiotensin receptor blocker (ARB) for at least 8 weeks prior to said administration or said use of said TACI-Ig fusion molecule.

Embodiment II-11. The method according to any one of Embodiments II-1 to II-10, wherein said IgA nephropathy is an IgA nephropathy confirmed by kidney biopsy.

Embodiment 11-12. The method according to any one of Embodiments II-1 to II-11, wherein said TACI-Ig fusion molecule is administered in an amount of 25 to 150 mg per week.

Embodiment 11-13. The method according to any one of Embodiments II-1 to 11-12, wherein said TACI-Ig fusion molecule is administered for at least 4 weeks.

Embodiment 11-14. The method according to any one of Embodiments II-1 to 11-13, wherein said TACI-Ig fusion molecule is administered by subcutaneous administration.

Embodiment 11-15. A method according to any one of Embodiments II-1 to 11-14, wherein said administration or said use of said TACI-Ig fusion molecule results in a reduction in the serum level of Gd-IgA1 antibodies compared to the situation before said administration or said use of said TACI-Ig fusion molecule.

Embodiment 11-16. Use of a transmembrane activator and calcium modulator and cyclophilin ligand-interactor (TACI)-immunoglobulin (Ig) fusion molecule for the manufacture of a medicament for the treatment of IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-17. Use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-18. Use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-19. Use of a transmembrane activator and calcium modulator and cyclophilin ligand-interactor (TACI)-immunoglobulin (Ig) fusion molecule for the manufacture of a medicament for the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-20. A transmembrane activator and calcium modulator and cyclophilin ligand-interactor (TACI)- immunoglobulin (Ig) fusion molecule for use in the treatment of IgA nephropathy in a patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-21. A transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-22. A transmembrane activator and calcium modulator and cyclophilin ligand-interactor (TACI)- immunoglobulin (Ig) fusion molecule for use in the treatment of IgA nephropathy (IgAN) by reducing the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

Embodiment 11-23. A transmembrane activator and calcium modulator and cyclophilin ligand-interactor (TACI)-immunoglobulin (Ig) fusion molecule for use in the treatment of IgA nephropathy (IgAN) by reducing the serum Gd-IgA1 level and the proteinuria in an IgAN patient, wherein the TACI-Ig fusion molecule comprises:

(i) a TACI extracellular domain or fragment thereof which binds BLyS (B Lymphocyte Stimulator) and/or APRIL (A Proliferation-Inducing Ligand); and (ii) a human immunoglobulin-constant domain.

---

SEQUENCES

```
SEQ ID NO: 1 (Amino acid sequence of fragment of TACI extracellular
region included in Atacicept)
AMRSCPEEQYWDPLLGTCMSCKTICNHQSQRTCAAFCRSLSCRKEQGKFYDHLLRDCISCASIC
GQHPKQCAYFCENKLRS SEQ ID NO: 2 (Amino acid sequence of Ig region included in Atacicept)
DKTHTCPPCPAPEAEGAPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPSSIEKTISKAKGQPREPQV
YTLPPSRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK SEQ ID NO: 3 (Amino acid sequence of Atacicept)
AMRSCPEEQYWDPLLGTCMSCKTICNHQSQRTCAAFCRSLSCRKEQGKFYDHLLRDCISCASIC
GQHPKQCAYFCENKLRSEPKSSDKTHTCPPCPAPEAEGAPSVFLFPPKPKDTLMISRTPEVTCV
VVDVSHEDPEVKFNWYVDGVEVHNAKTKPREEQYNSTYRVVSVLTVLHQDWLNGKEYKCKVSNK
ALPSSIEKTISKAKGQPREPQVYTLPPSRDELTKNQVSLTCLVKGFYPSDIAVEWESNGQPENN
YKTTPPVLDSDGSFFLYSKLTVDKRWQQGNVFSCSVMHEALHNHYTQKSLSLSPGK SEQ ID NO: 4 (Amino acid sequence of Telitacicept)
SRVDQEERFPQGLWTGVAMRSCPEEQYWDPLLGTCMSCKTICNHQSQRTCAAFCRSLSCRKEQG
KFYDHLLRDCISCASICGQHPKQCAYFCENKLRSPVNLPPELDKTHTCPPCPAPEAEGAPSVFL
FPPKPKDTLMISRTPEVTCVVVDVSHEDPEVKFNWYVDGVEVHNAKTKPREEQYNSTYRVVSVL
TVLHQDWLNGKEYKCKVSNKALPSSIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEALHN
HYTQKSLSLSPGK SEQ ID NO: 5 (Amino acid sequence of TACI-Ig fusion protein T1 of
EP 2161287 B1)
SRVDQEERFPQGLWTGVAMRSCPEEQYWDPLLGTCMSCKTICNHQSQRTCAAFCRSLSCRKEQG
KFYDHLLRDCISCASICGQHPKQCAYFCENKLDKPHTCPLCPAPELLGGPSVFLFPKPPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDIAVE
WESNGQPENNYKATPPVLDSDGSFFLYSKLTVDKSRWQQGNVFSCSVMHEALHNHYTQKSLSLS
PGK SEQ ID NO: 6 (Amino acid sequence of TACI-Ig fusion protein T2 of
EP 2161287 B1)
SRVDQEEREPQGLWTGVAMRSCPEEQYWDPLLGTCMSCKTICNHQSQRTCAAFCRSLSCRKEQG
KFYDHLLRDCISCASICGQHPKQCAYFCENKLRSPVNLPPELDKPHTCPLCPAPELLGGPSVFL
FPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCLVK
GFYPSDIAVEWESNGQPENNYKATPPVLDSDGSFFLYSKLTVDKSRWQQGNVFSCSVMHEALHN
HYTQKSLSLSPGK SEQ ID NO: 7 (Amino acid sequence of TACI-Ig fusion protein T3 of
EP 2161287 B1)
SRVDQEERFPQGLWTGVAMRSCPEEQYWDPLLGTCMSCKTICNHQSQRTCAAFCRSLSCRCGQH
PKQCAYFCENKLRSPVNLPPELGGGGGGGGGDKPHTCPLCPAPELLGGPSVFLFPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEW
ESNGQPENNYKATPPVLDSDGSFFLYSKLTVDKSRWQQGNVFSCSVMHEALHNHYTQKSLSLSP
GK
```

-continued

```
SEQUENCES
```

```
SEQ ID NO: 8 (Amino acid sequence of TACI-Ig fusion protein according
to SEQ 4 of U.S. 8193316B2)
SRVDQEERFPQGLWTGVAMRSCPEEQYWDPLLGTCMSCKTICNHQSQRTCAAFCRSLSCRKEQG
KFYDHLLRDCISCASICGQHPKQCAYFCENKLRSPVNLPPELGGGGGGGGGDKPHTCPLCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKN
QVSLTCLVKGFYPSDIAVEWESNGQPENNYKATPPVLDSDGSFFLYSKLTVDKSRWQQGNVFSC
SVMHEALHNHYTQKSLSLSPGK
```

```
SEQ ID NO: 9 (Amino acid sequence of TACI-Ig fusion protein T4 of
EP 2161287 B1)
AMRSCPEEQYWDPLLGTCMSCKTICNHQSQRTCAAFCRSLSCRKEQGKFYDHLLRDCISCASIC
GQHPKQCAYFCENKLRSEPKSSDKPHTCPLCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENN
YKATPPVLDSDGSFFLYSKLTVDKSRWQQGNVFSCSVMHEALHNHYTQKSLSLSPGK
```

```
SEQ ID NO: 10: (Amino acid sequence of human TACI)
MSGLGRSRRGGRSRVDQEERFPQGLWTGVAMRSCPEEQYWDPLLGTCMSCKTICNHQSQRTCAA
FCRSLSCRKEQGKFYDHLLRDCISCASICGQHPKQCAYFCENKLRSPVNLPPELRRQRSGEVEN
NSDNSGRYQGLEHRGSEASPALPGLKLSADQVALVYSTLGLCLCAVLCCFLVAVACFLKKRGDP
CSCQPRSRPRQSPAKSSQDHAMEAGSPVSTSPEPVETCSFCFPECRAPTQESAVTPGTPDPTCA
GRWGCHTRTTVLQPCPHIPDSGLGIVCVPAQEGGPGA
```

```
SEQ ID NO: 11 (Amino acid sequence of human TACI extracellular domain)
MSGLGRSRRGGRSRVDQEERFPQGLWTGVAMRSCPEEQYWDPLLGTCMSCKTICNHQSQRTCAA
FCRSLSCRKEQGKFYDHLLRDCISCASICGQHPKQCAYFCENKLRSPVNLPPELRRQRSGEVEN
NSDNSGRYQGLEHRGSEASPALPGLKLSADQVALVYST
```

EXAMPLES

The following examples describe methods and study data relating to the present disclosure, along with comparative disclosure. It is understood that various embodiments of the disclosure reflected in the examples may be practiced, given the general description provided above. Although the foregoing invention has been described in some detail by way of illustration and example for purposes of clarity of understanding, the description and examples should not be construed as limiting the scope of the invention.

Example 1

A randomized, double-blind, placebo-controlled clinical study was carried out to evaluate the effects of atacicept administration in a group of IgA Nephropathy (IgAN) patients suffering from persistent proteinuria, i.e. in a patient group that has a high risk to develop severe renal complications.

Patient Selection

During screening of patients, key inclusion criteria were:
male/female subjects≥18 years of age
biopsy-proven IgAN
persistent proteinuria with UPCR≥1 mg/mg by 24-hour urine collection during the screening period; or persistent proteinuria with UPCR≥0.75 mg/mg by 24-hour urine collection during the screening period with at least one documented historical UPCR≥1 mg/mg within 12 months prior to the screening visit while on ACEi and/or ARB therapy
patient was on stable, optimized dose of Angiotensin Converting Enzyme Inhibitor (ACEi) and/or Angiotensin Receptor Blockers (ARB) for ≥8 weeks prior to screening
All enrolled patients had proteinuria≥1 g/day despite maximal standard of care (SOC) therapy (i.e. optimized ACE inhibitor and/or ARB).

The study target population was chosen because this level of proteinuria has been associated with high risk of significant renal outcomes such as end stage renal disease (up to 60-70% risk within 20 years).

Key exclusion criteria were
≥50% glomerulosclerosis or cortical area involved by tubular atrophy or interstitial fibrosis
eGFR≤35 mL/min/1.73 m$^2$
concomitant significant renal disease other than IgAN, including Henoch Schonlein purpura
serum IgG<6 g/L
prior cyclophosphamide use
concomitant immunosuppressant use
blood pressure higher than 140/90 mmHg
active infection or high infectious risk Treatment The study was initially designed to consist of two parts (Parts A and B), but eventually only the first part (A) was carried out. The study schematic of Part A is shown in FIG. 1.

The study was carried out with 16 enrolled IgAN patients. Patients were randomized 1:1:1 to receive
Group 1: placebo; or
Group 2: 25 mg atacicept; or
Group 3: 75 mg atacicept
once weekly by subcutaneous (SC) injection. Injection volume was 1.0 mL. Placebo was supplied as a sterilized solution for injection in pre-filled syringes matching the atacicept pre-filled syringes. The injections were performed SC into the abdomen (anterior abdominal wall) or thighs, using the pre-filled syringes and standard SC injection technique. Injection sites were rotated for all doses and were per instruction at least 5 centimeters away (approximately 2 inches) from the previous injection in areas without any existing skin pathology. The injections were intended to be administered at approximately the same time and day of each week.

Atacicept was formulated as a solution with a concentration of either 25 or 75 mg/ml (in an aqueous solution containing trehalose dihydrate and sodium acetate at a pH of 5.0.

In parallel, the patients of all groups continued to receive an optimized dose of Angiotensin Converting Enzyme Inhibitor (ACEi) and/or Angiotensin Receptor Blockers (ARB) as the SOC (standard of care) basis therapy.

Demographics and Baseline Characteristics

Demographics and baseline characteristics for the different treatment groups are summarized in Table 1 below.

TABLE 1

| | Placebo (n = 5) | Atacicept 25 mg (n = 6) | Atacicept 75 mg (n = 5) | Total (n = 16) |
|---|---|---|---|---|
| Age, mean ± SD | 46 ± 2.9 | 40 ± 16.8 | 43 ± 8.9 | 43 ± 11.1 |
| Sex, n (%) Female | 1 (20.0) | 5 (83.3) | 2 (40.0) | 8 (50.0) |
| Race, n (%) | | | | |
| White | 4 (80.0) | 5 (83.3) | 2 (40.0) | 11 (68.8) |
| Black | 0 | 0 | 0 | 0 |
| Asian | 1 (20.0) | 1 (16.7) | 1 (20.0) | 3 (18.8) |
| other | 0 | 0 | 2 (40.0) | 2 (12.5) |
| Ethnicity, n (%) | | | | |
| Hispanic | 0 | 1 (16.7) | 3 (60.0) | 4 (25.0) |
| Disease duration from diagnosis, years | | | | |
| Median (25th, 75th percentile) | 1.26 (1.05, 12.42) | 2.17 (0.12, 2.99) | 2.55 (2.52, 4.62) | 2.38 (0.69, 4.20) |
| Duration from most recent kidney biopsy, years | | | | |
| Median (25th, 75th percentile) | 0.50 (0.31, 1.05) | 1.80 (0.12, 2.96) | 0.97 (0.33, 2.52) | 1.01 (0.23, 2.39) |
| History of systemic corticosteroids, n (%) | 1 (20.0) | 2 (33.3) | 1 (20.0) | 4 (25.0) |
| Concomitant medications, n (%) | | | | |
| ACEi and/or ARB | 5 (100.0) | 6 (100.0) | 5 (100.0) | 16 (100.0) |
| ACEi | 3 (60.0) | 3 (50.0) | 1 (20.0) | 7 (43.8) |
| ARB | 2 (40.0) | 3 (50.0) | 4 (80.0) | 9 (56.3) |
| Diuretics | 0 | 2 (33.3) | 1 (20.0) | 3 (18.8) |
| History of tonsillectomy, n (%) | 0 | 0 | 2 (40.0) | 2 (12.5) |
| eGFR by CKD-EPI (mL/min/1.73 m²) median (IQR) | 49 (48, 54) | 57 (53, 85) | 55 (52, 92) | |
| Proteinuria | | | | |
| UPCR by 24-hr urine collection (mg/mg) median (IQR) | 1.41 (1.29, 1.61) | 1.72 (0.85, 2.1) | 1.40 (1.33, 2.0) | |
| 24-hr UPCR > 2 (%) | 0 | 3 (50) | 1 (20) | |
| IgA (g/L) mean ± SD | 3.97 ± 1.72 | 3.58 ± 1.22 | 3.02 ± 0.85 | |
| IgG (g/L) mean ± SD | 10.51 ± 2.63 | 9.45 ± 1.82 | 10.89 ± 1.10 | |
| IgM (g/L) mean ± SD | 1.29 ± 0.51 | 0.90 ± 0.55 | 1.09 ± 0.30 | |

TABLE 1-continued

| | Placebo (n = 5) | Atacicept 25 mg (n = 6) | Atacicept 75 mg (n = 5) | Total (n = 16) |
|---|---|---|---|---|
| Gd-IgA1 (ng/mL) median (IQR) | 8100 (4330.0, 9500.0) | 5715 (3750.0, 9010.0) | 5250 (4350.0, 8750.0) | |

ACEi: angiotensin converting enzyme inhibitor;
ARB: angiotensin receptor blocker;
eGFR by CKD-EPI: estimated glomerular filtration rate calculated by CKD-EPI (Chronic Kidney Disease Epidemiology Collaboration) formula;
IQR: interquartile range Assays Samples were taken longitudinally at prescheduled time-points. After Day 1, results of analyses that could reveal the PD effects of atacicept in an individual subject were blinded to the study site, the Sponsor, and the CRO. The analyses included typical assessments to monitor potential changes in vitals, ECGs, hematology laboratory chemistry and urine analysis.

The assessments of immunoglobulins (IgA, IgM, and IgG) was performed by an immunoturbidometric method as part of the standard central lab panel (Q2 Solutions, US). The measurement of complement factors (C3 and C4) and flow cytometry of immune cells (including B cell and plasma cell levels) were carried out by standard assays.

Galactose-deficient IgA1 levels in serum were determined by ELISA using a commercial kit by Immuno-Biological Laboratories, Japan (Cat #27600; Suzuki et al., Clin Exp Nephrol (2014)). Briefly, the KM55 ELISA kit was used according to the manufacturer's specifications (IBL, Japan). Serum samples were diluted in proportions of 1:50 with EIA buffer and incubated for 60 min with plate lid. After washing four times with wash buffer, prepared labeled antibody was incubated for 30 min. Plates were washed 5 times, followed by adding of 50 μL TMA solution and incubation for 30 min in the dark. At last, the color reaction was stopped, and the absorbance was measured at 450/625 nm. This assay was counter-validated by Merck KGaA.

The atacicept concentration in serum was determined by measuring serum levels of free atacicept, atacicept•BLyS complex and total atacicept (defined as free atacicept+ atacicept•BLyS complex) quantified using enzyme-linked immunosorbent assay. Serum was incubated with a biotin-conjugated monoclonal antibody specific for atacicept (free or total atacicept detection) and immobilized on a strepta-vidin-coated microplate. After washing, an atacicept-specific monoclonal antibody conjugated to horseradish peroxidase (HRP) was added. Atacicept species were detected and quantified using standard chemiluminescence methods.

The number of mature naive B cells was determined by flow cytometry. Peripheral blood was collected from patients at selected clinical sites and transported to a contract research organization within 24 hours. Whole blood was incubated with appropriate dilutions of directly labelled fluorescent antibodies and red blood cells were lysed using a standard cell lysing reagent. Counting beads were used to determine total T- and B-cell concentrations. Four-color immunophenotyping, using standard flow cytometry methods, was used to differentiate the cell types.

The estimated glomerular filtration rate (eGFR) was determined based on the CKD-EPI (Chronic Kidney Disease Epidemiology Collaboration) formula.

UPCR (urine protein:creatinine ratio) from 24-hour urine was determined by standard methods. Spot UPCR assessment was carried out by standard methods from first morning void spot urine sample.

Results after 24 Weeks

Figure 2C:
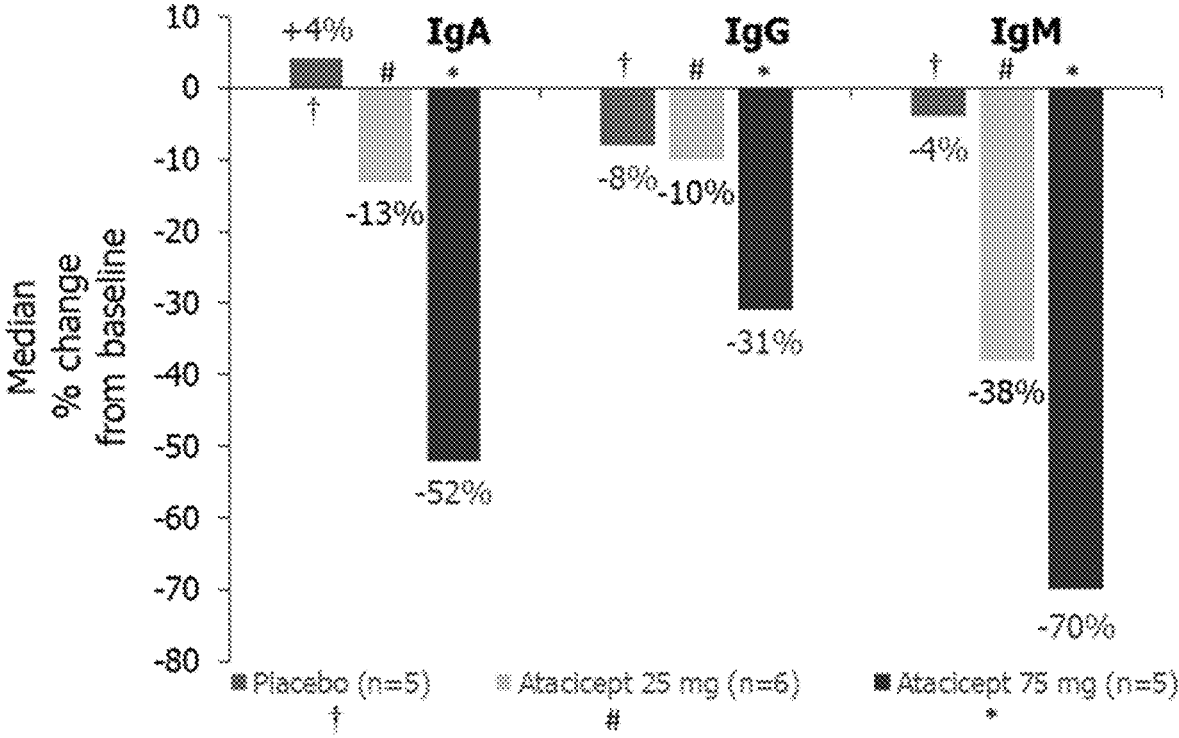

A prospectively planned interim analysis after the patients had completed 24 weeks of treatment showed a proof of concept for the effects of atacicept in patients with IgAN and persistent proteinuria based on following findings:

Surprisingly, a consistent, dose-dependent reduction in Gd-IgA1 (FIG. 2A) was observed at week 24. In parallel, proteinuria (24 hour UPCR) showed a higher median % reduction from baseline with atacicept at week 24: −18.67% and −25.34% with atacicept 25 mg and 75 mg, respectively, vs +0.098% with placebo (FIG. 2B). Moreover, a consistent, dose-dependent reduction on serum immunoglobulins IgA, IgG and IgM was observed (FIG. 2C).

Figure 3:
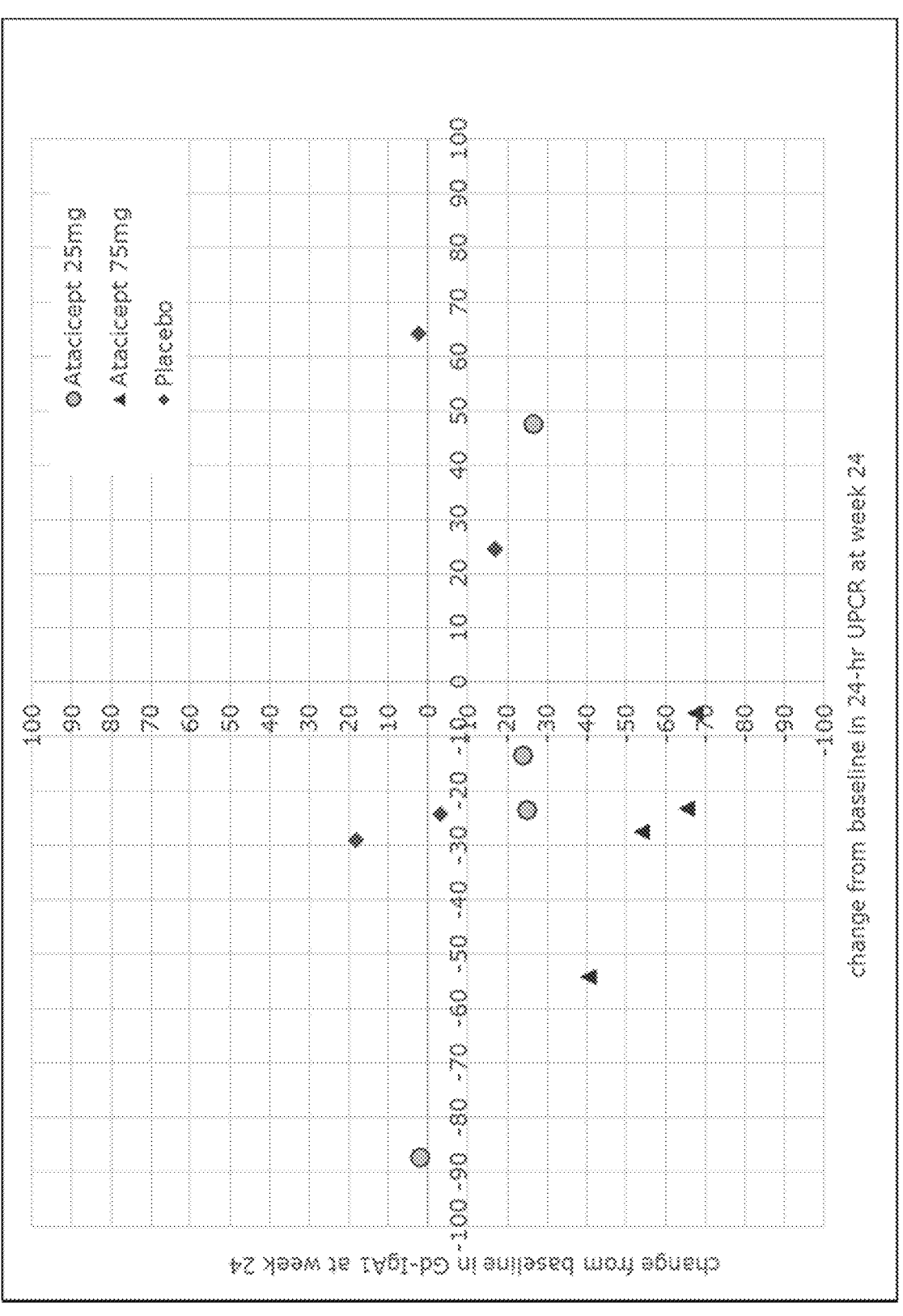
FIG. 3 is a graph showing the dose relationship observed for the change from baseline in Gd-IgA1 and 24-hour UPCR at week 24 in the study of Example 1.

In particular, the 75 mg Atacicept dose level was associated with greater reduction in Gd-IgA1 and correlated with a reduction in proteinuria by 24 hour-UPCR at week 24 (FIG. 3).

Time course plots further demonstrated clear dose-dependent reduction of serum Gd-IgA1, IgA IgG, and IgM levels with atacicept treatment. Renal function as measured by eGFR remained stable over time. Treatment emergent adverse events (TEAEs) were reported by 81% of the subjects. TEAEs were mild or moderate in severity, with no severe TEAEs reported. Injection site reactions (ISRs) and Infections were the most common TEAEs. While ISRs were reported in atacicept groups only, no obvious dose-effect was observed in frequency or severity. No serious related events, events with severe hypogammaglobulinemia or fatal outcome were reported.

Figure 4:
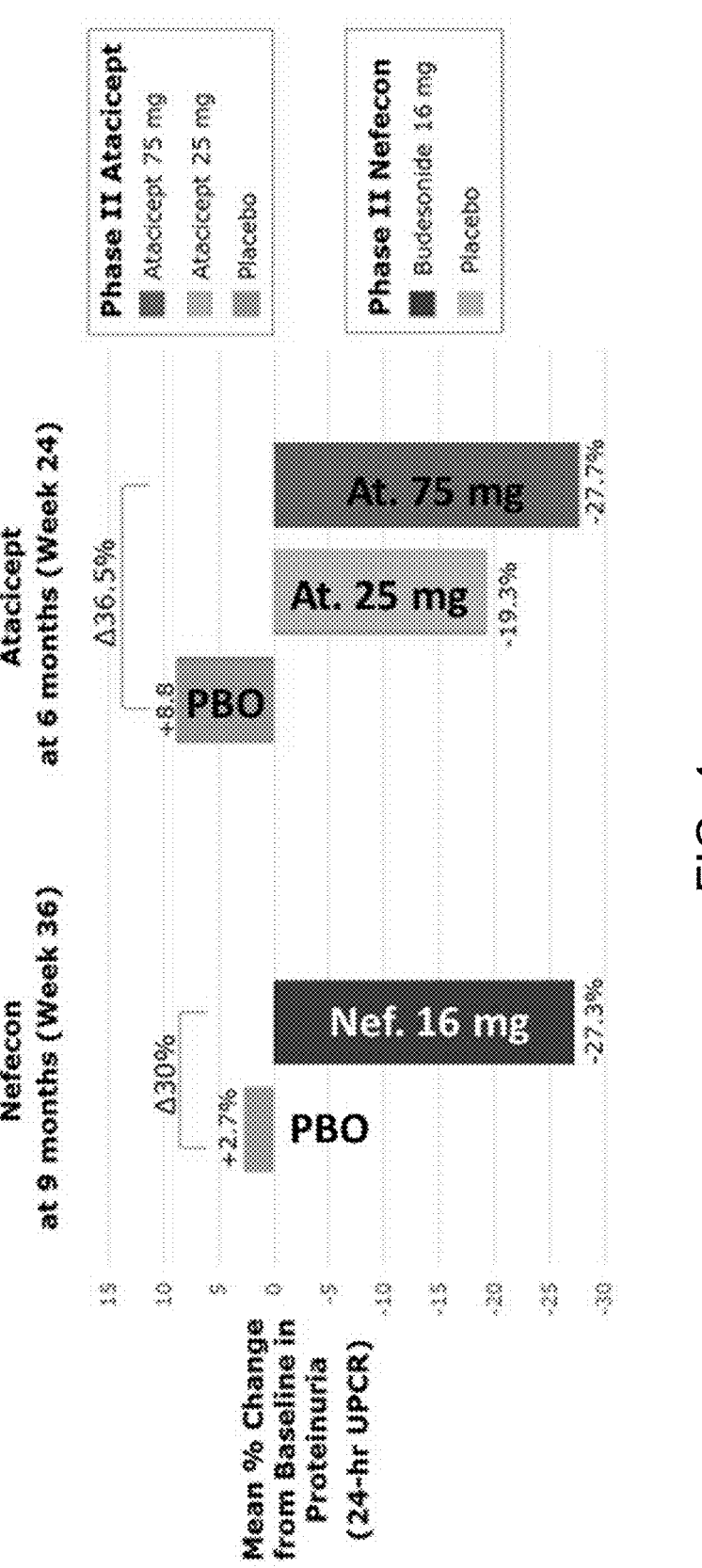
FIG. 4 shows a comparison of treatment effect between atacicept 75 mg and budesonide 16 mg.

The magnitude of proteinuria reduction (mean percent change from baseline) observed with 24 week treatment with atacicept 75 mg SC (subcutaneous administration) weekly appeared to be comparable to the 36-week treatment with budesonide 16 mg oral (nefecon) daily in the Phase II NEFIGAN study as reported by (Fellström et al., Lancet (2017)) (FIG. 4). However, budesonide only minimally affects the Gd-IgA1 level (Bhachu J S, 2018).

Results after Completion of Study

The treatment (once weekly subcutaneous administration of placebo, 25 mg atacicept or 75 mg atacicept) was continued until week 48. Measurements were continued in the following weeks.

The measurements of the serum atacicept concentration over time confirmed that subcutaneous atacicept administration results in a dose-dependent exposure, as expected. Moreover, it was found that, compared to baseline, the number of mature naive B cells was reduced in the atacicept-treated patient groups over time, whereas it remained rather stable in the placebo group. This is a well-known mode of action-related effect of atacicept.

Figure 5A:
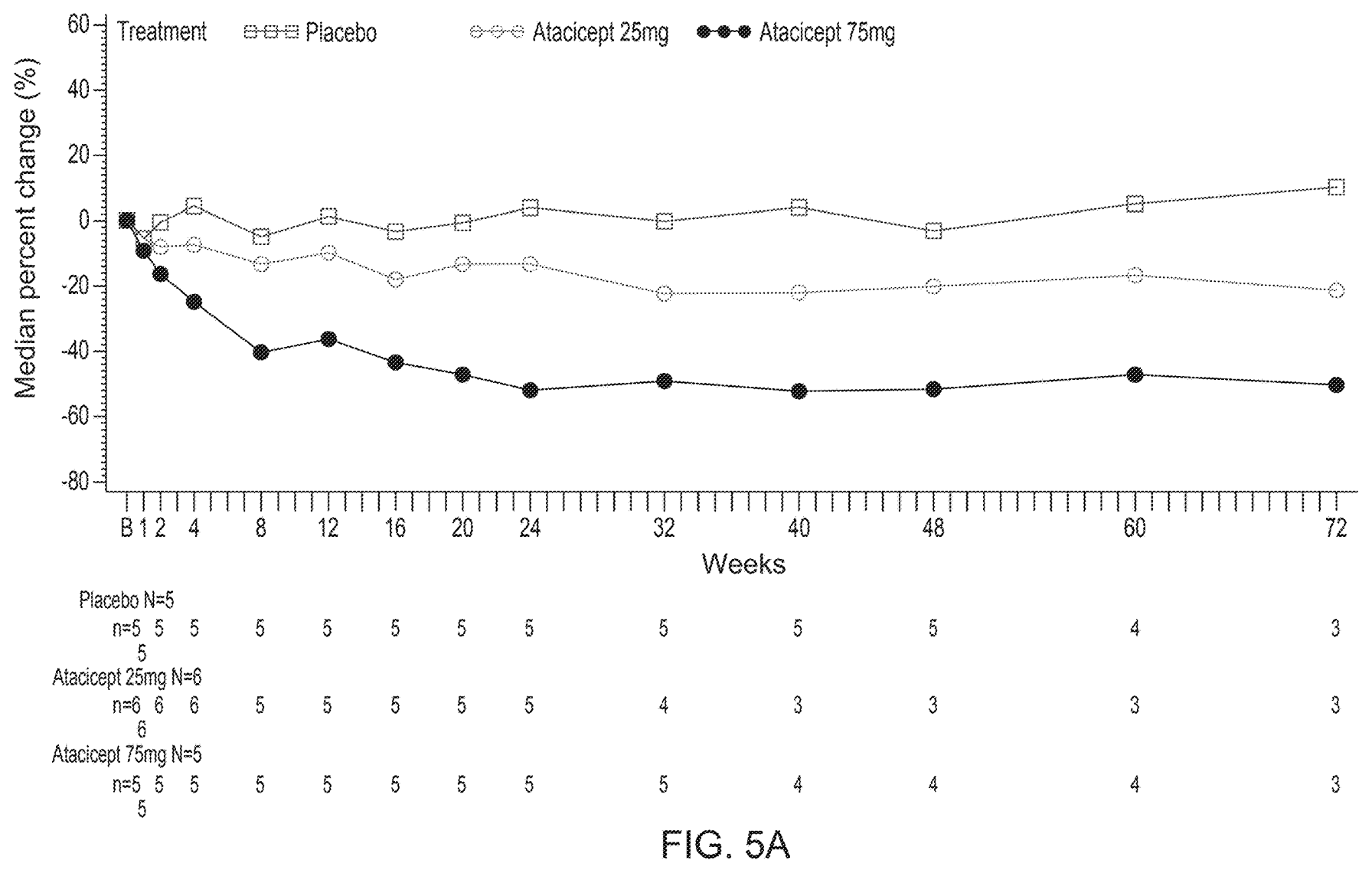
Figure 5B:
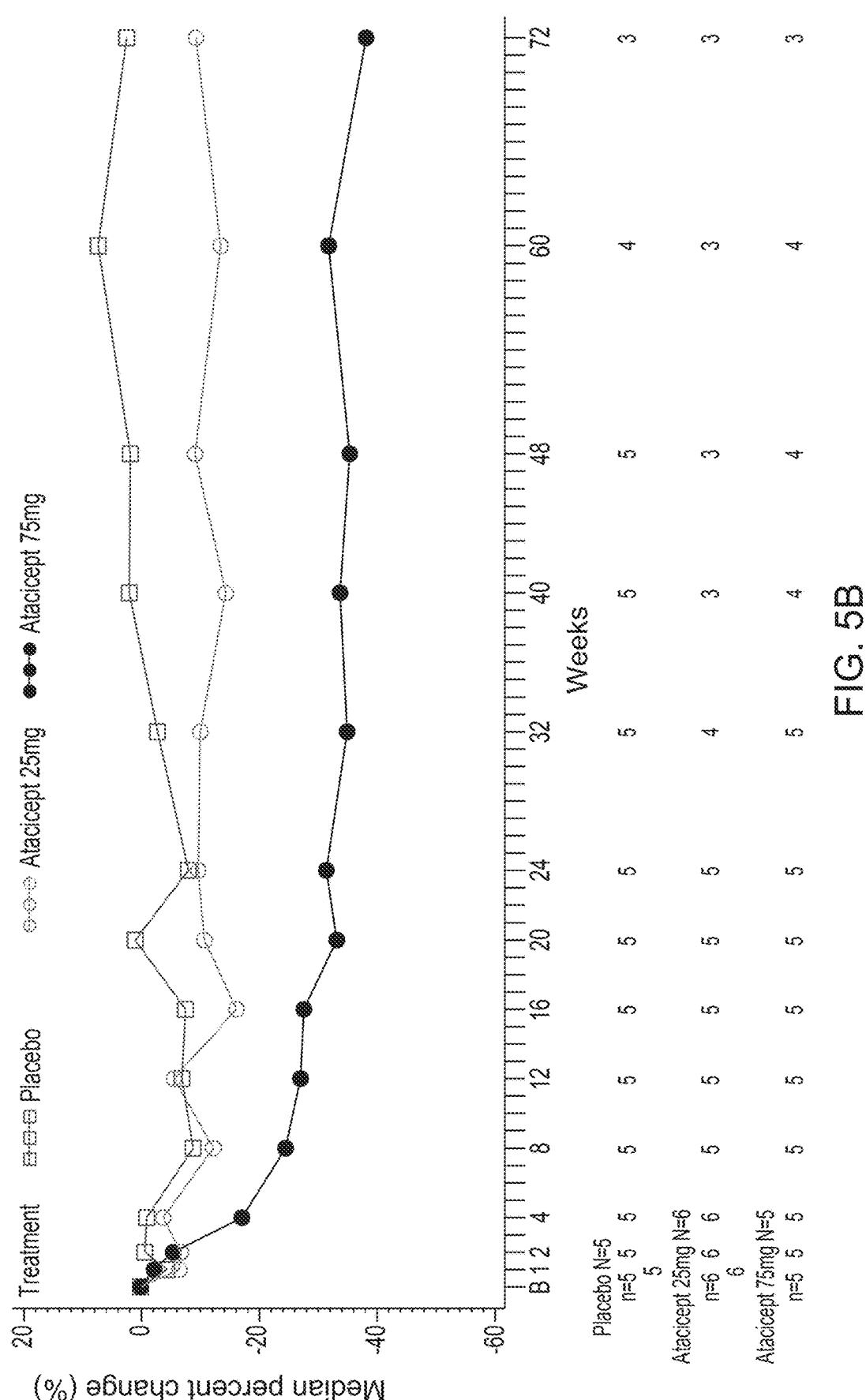
Figure 5C:
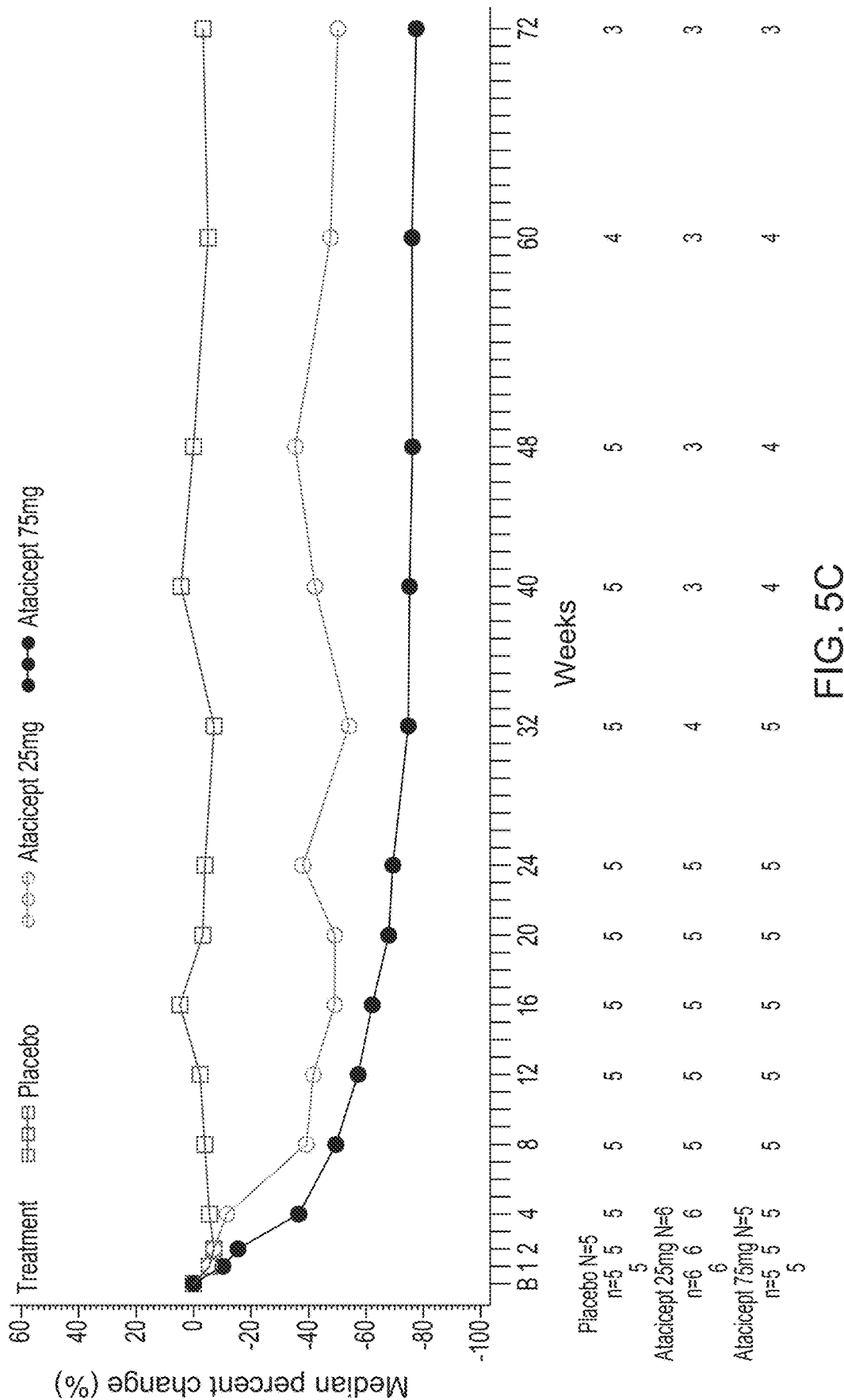

After completion of the study (Part A), longitudinal IgA, IgG, IgM were confirmatory with the interim results and showed with atacicept treatment for all these immunoglobulins clear dose-dependent reductions in the serum concentration vs baseline (FIGS. 5A-5C).

Figure 5D:
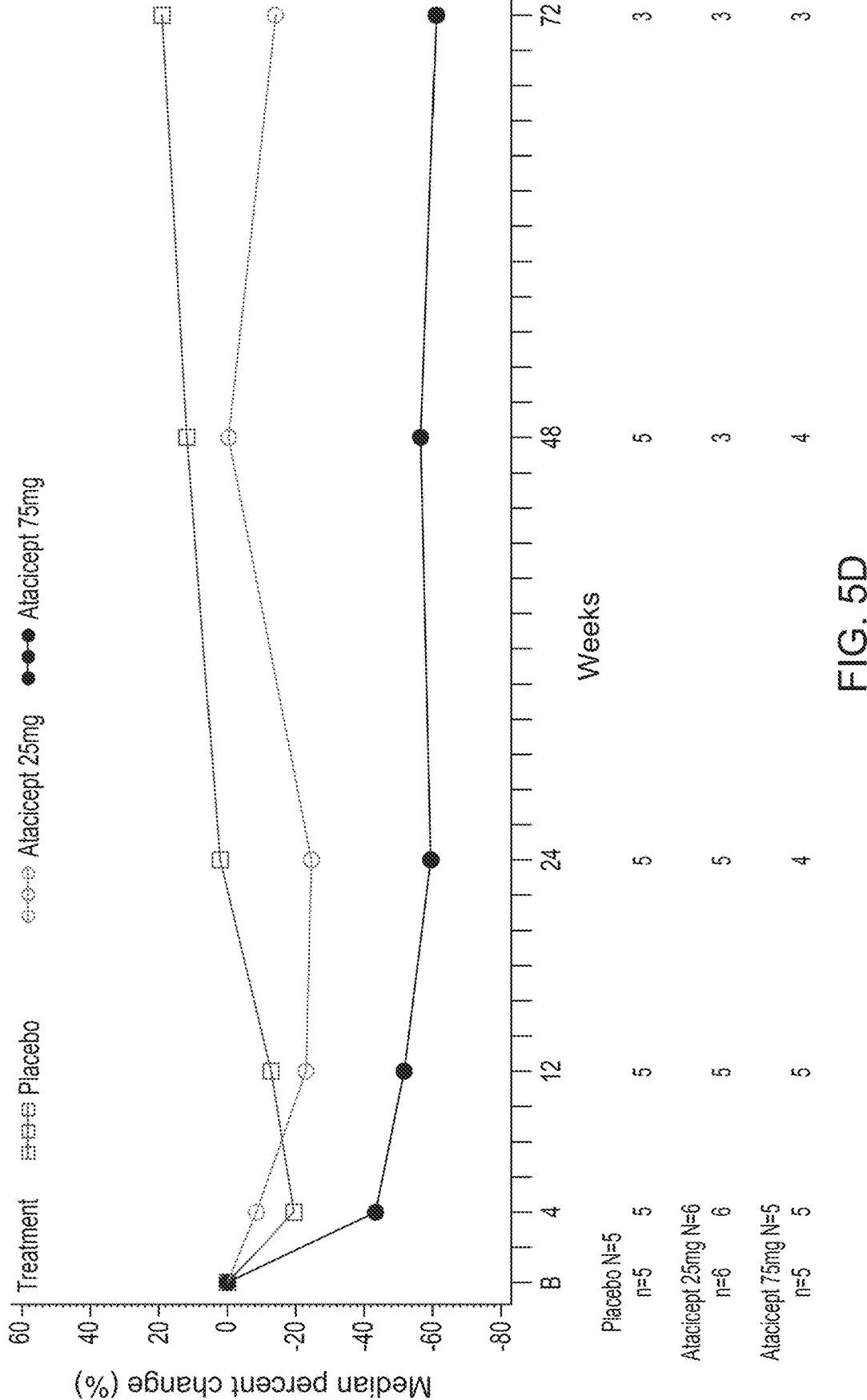

Surprisingly, simultaneously a strong, dose-dependent effect of atacicept was also observed with regard to the reduction of serum Gd-IgA1 (FIG. 5D).

To our knowledge, this is the first time that a drug causes reduction in pathogenic Gd-IgA1 levels and simultaneously reduces the serum immunoglobulins IgA, IgG and IgM. To the best of our knowledge up to date, there is no other drug which can reduce serum Gd-IgA1 levels by as much as 25% (atacicept 25 mg) or 60% (atacicept 75 mg).

Figure 5E:
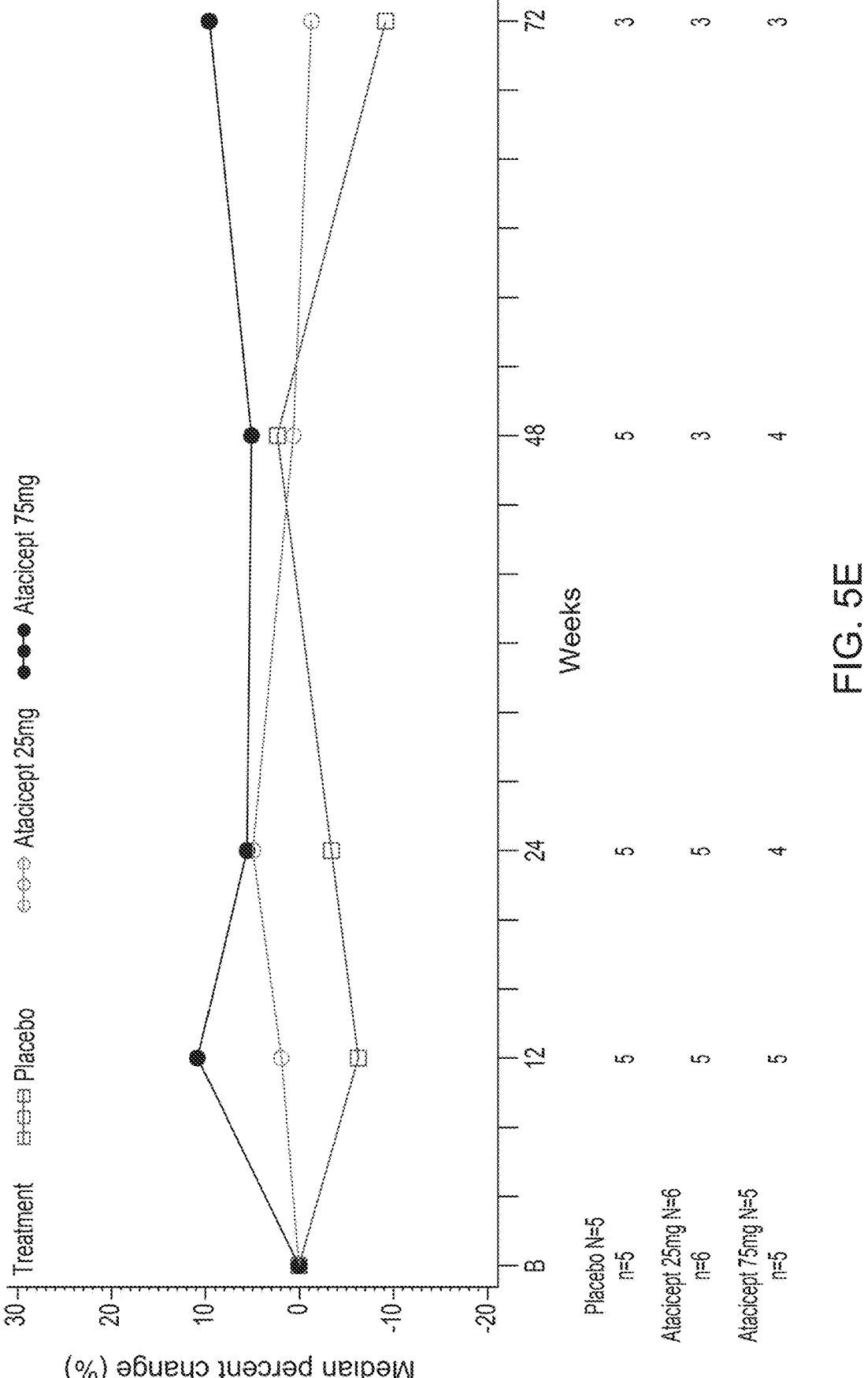
Figure 5F:
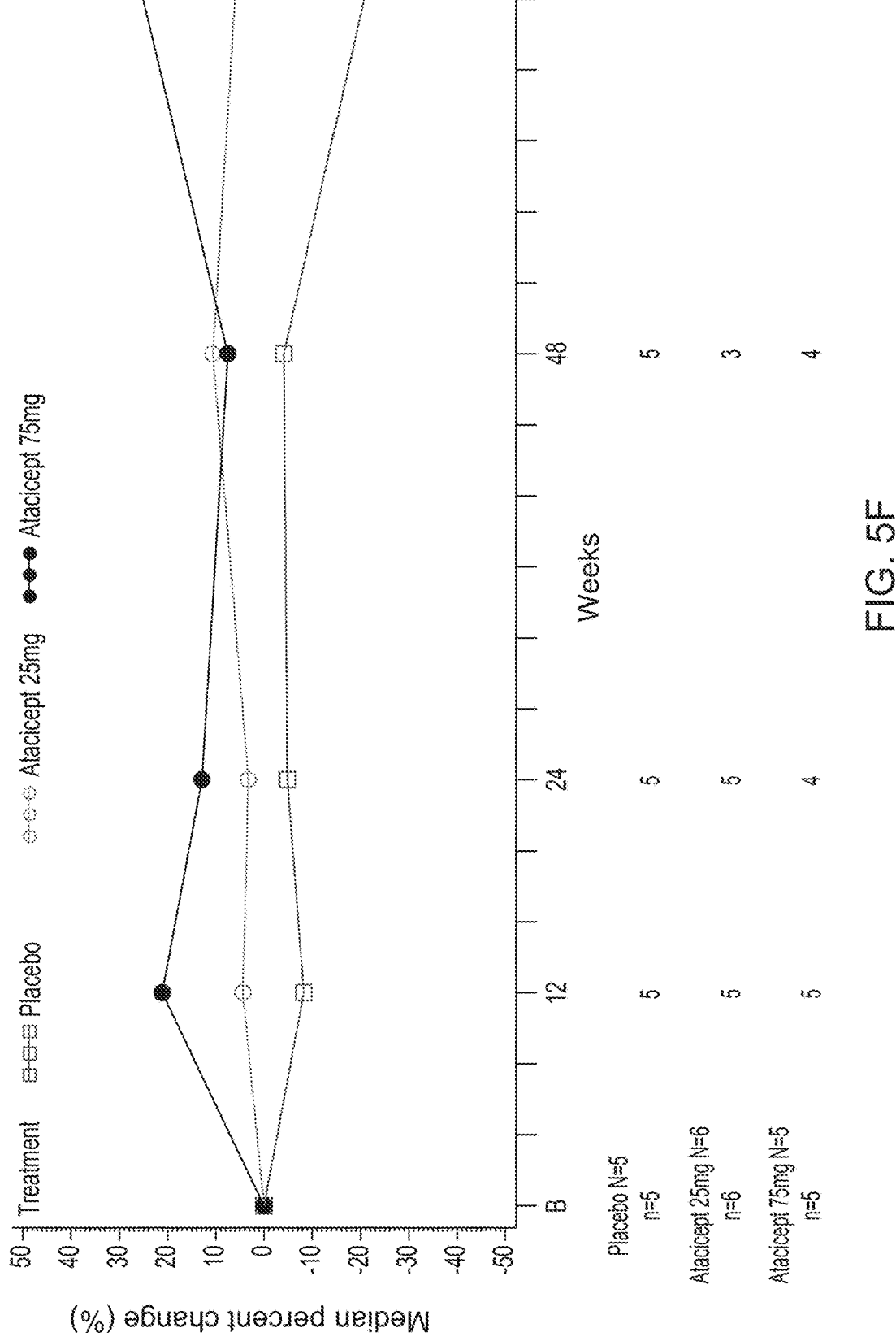

Measurement of the serum levels of complement C3 showed a slight increase with atacicept therapy (esp. 75 mg), while a slight decrease to no change was observed with placebo (FIG. 5E). Similarly, overall a dose-dependent increase of serum complement C4 from baseline was observed with atacicept treatment (FIG. 5F).

Figure 5G:
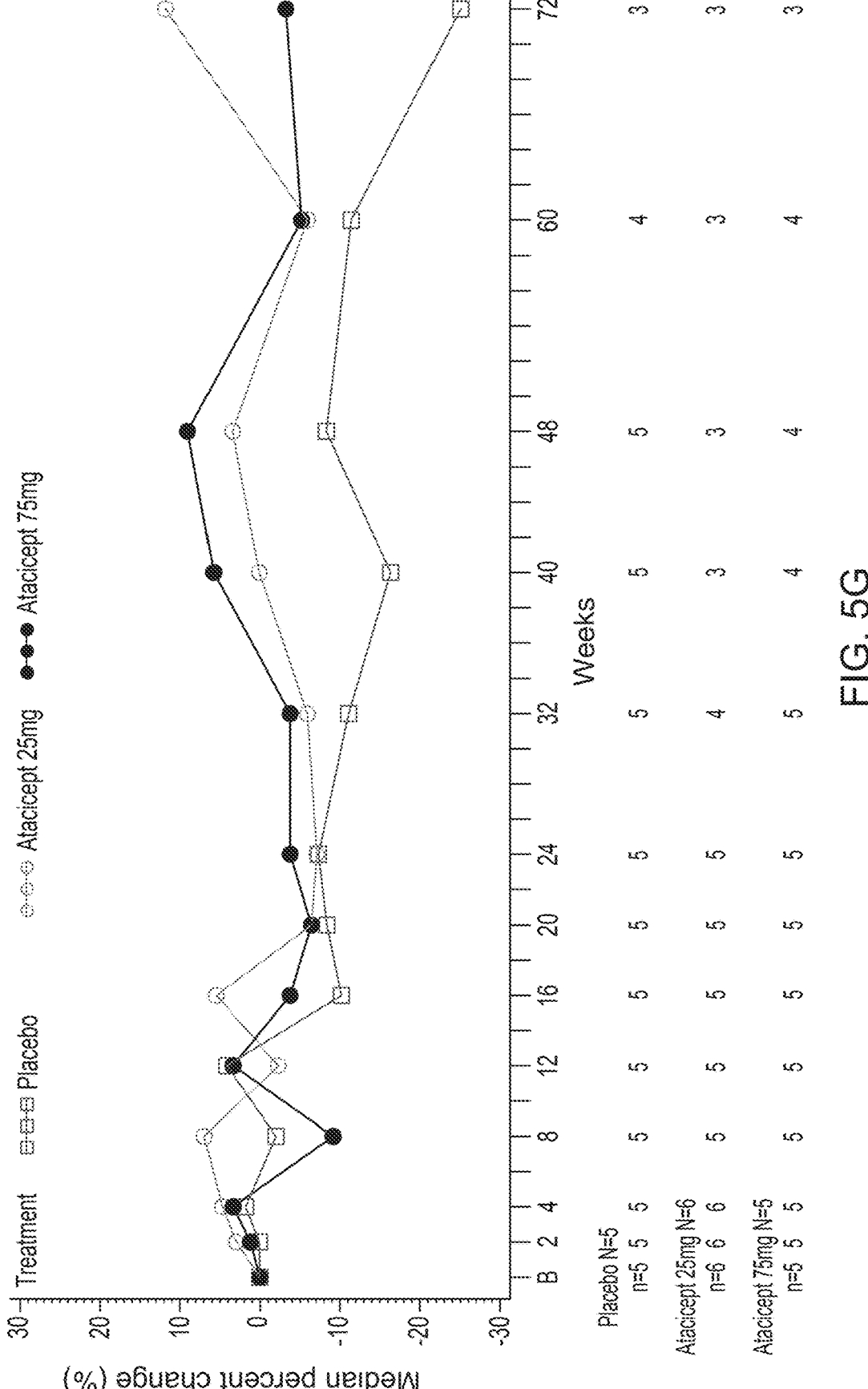

There was a progressive decline in renal function by eGFR in the placebo group while the atacicept groups appeared to have relatively stable renal function with some fluctuations through week 24 and a slight improvement by week 48 (FIG. 5G).

Figure 6:
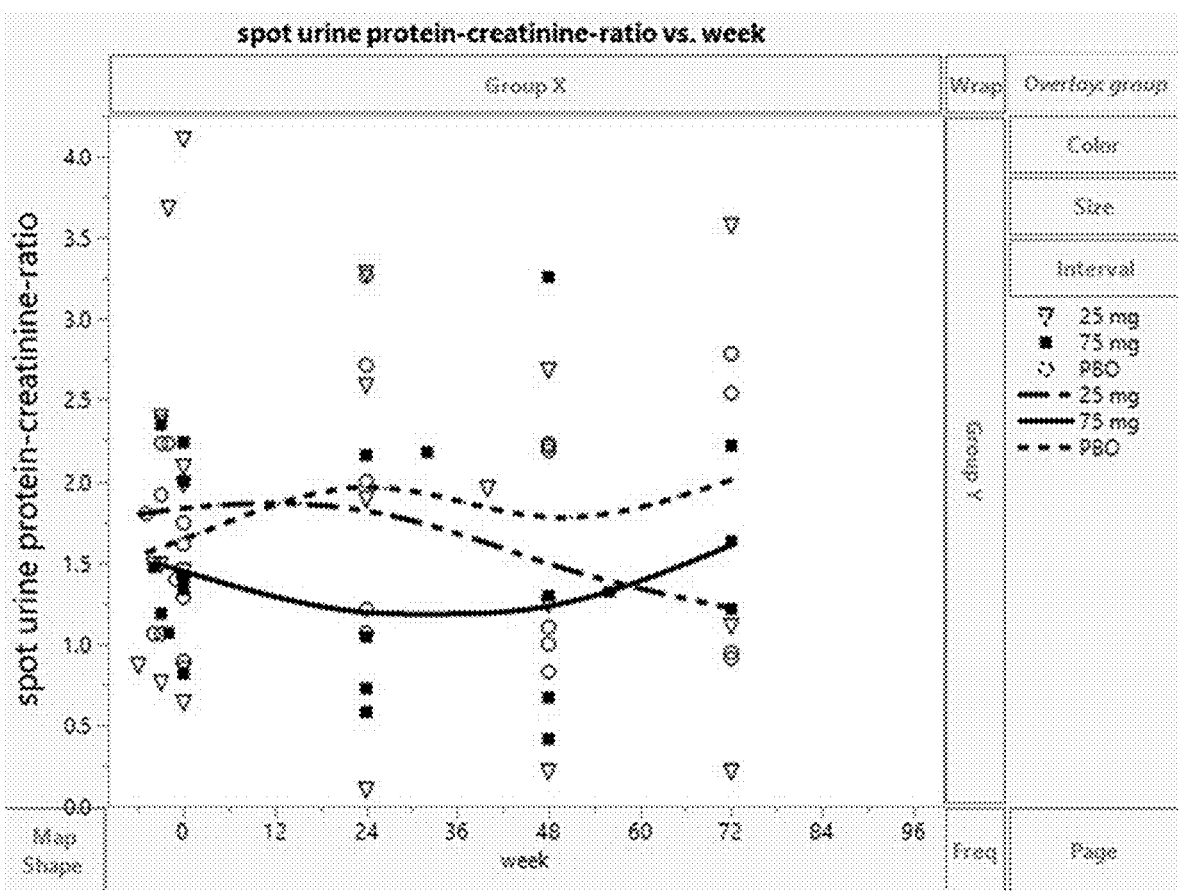
FIG. 6 shows change from baseline (CFB, i.e. change vs. the value of day 1 before the first TACI-Ig administration) for the spot urine protein:creatinine ratio in the study of Example 1 (individual patient values as well as fitted curves based on these values). 25 mg: 25 mg atacicept group; 75 mg: 75 mg atacicept group; PBO: placebo group.

From a preliminary analysis of the data points (FIG. 6), it was observed that the reduction in Gd-IgA1 translated into a reduction of the spot UPCR value that was dose-dependent during the time of treatment (48 weeks). The observed clinically meaningful reduction in 24-hour proteinuria at week 24 with atacicept treatment was lost at week 48 in the atacicept 75 mg group, which was driven by 2 patients (low sample size; 2 subjects in atacicept 75 mg with post-week 24 data had increased proteinuria after week 24. One subject had worsening of hypertension off aldosterone. The other subject had increased proteinuria and eGFR at week 48 and then both decreased at week 72).

Thus, the unexpected reduction in Gd-IgA1 by atacicept observed in the patients of this study translates into a disease modifying potential for patients suffering from IgA nephropathy.

REFERENCES

Bhachu J S, Cionti K, Muto M et al. Kidney Dis (2018): 121-122

Canfield and Morrison, J. Exp. Med. (1991), vol. 173 p. 1483 ff.

Cattran D C et al., Kidney Int. (2009), vol. 76, p. 534-545

Czerkinsky C, Koopman W J, Jackson S, et al., J Clin Invest (1986), vol. 77(6), p. 1931-1938

Descamps-Latscha B et al., Kidney Int (2004), vol. 66(4), p. 1606-1612

Do et al., J Exp Med (2000), vol. 192(7), p. 953-964

Fellström B, Barratt J, Cook H et al., Lancet (2017), vol. 389, p. 2117-2127

Floege J et al., J Am Soc Nephrol (2011), vol. 22(10), p. 1785-1794

Gross J A et al., Immunity (2001), vol. 15, p. 289-302

International Society of Nephrology. Kidney Disease—Improving Global Outcomes. J Int Soc Nephrol (2012)

Kabat et al. (eds.), Sequences of Proteins of Immunological Interest, 5th ed. (1991), National Institutes of Health (Bethesda, USA)

Levey A S et al., Ann Intern Med. (2009), vol. 150(9), p. 604-612

Liu D et al., International Immunopharmacology (2020), vol. 82:106362

Lv J, et al., J Am Soc Nephrol (2012), vol. 23(6), p. 1108-1116

Makita Y et al, Kidney International (2020), vol. 97, p. 340-349

Marsters S A, Yan M, Pitti R M, Haas P E, Dixit V M, Ashkenazi A, Curr Biol (2000), vol. 10(13), p. 785-788

Moore et al., Science (1999), vol. 285(5425), p. 260-263

Novak J, Julian B A, Tomana M, et al., Semin Nephrol (2008), vol. 28(1), p. 78-87

Raschke V, Sosnovtseva S, Ward C D, Hong J S, Smith R, Albert V et al., J Immunol (2002), vol. 169, p. 4314-4321

Schneider et al., J Exp Med (1999), vol. 189(11), p. 1747-1756

Selvaskandan H et al., Clinical and Experimental Nephrology (2019), vol. 23, p. 577-588

Suzuki Y, Matsuzaki K, Suzuki H et al., Clin Exp Nephrol (2014), vol. 18(5), p. 770-777

Tao et al., J. Exp. Med. (1993), vol. 178, p. 661 ff.

Thompson J S, Bixler S A, Qian F, Vora K, Scott M L, Cachero T G, Science (2001), vol. 293, p. 2108-2111

Tomana M, Matousovic K, Julian B A, et al., Kidney Int (1997), vol. 52(2), p. 509-516

Wyatt R J, Julian B A, N Engl J Med (2013), vol. 368(25), p. 2402-2414

Yamasaki et al., Monoclon Antib Immunodiagn Immunother (2018), vol. 37(6), p. 252-256

Yang et al., PLoS ONE (2015), vol. 10 (9): e0137460.

Yasutake et al., Nephrol Dial Transplant (2015), vol. 30(8), p. 1315-1321

Zhao et al., Kidney International (2012), vol. 82, p. 790-796

The invention claimed is:

1. A method for treating a human patient having IgA nephropathy (IgAN), the method comprising:
   administering to the human patient a therapeutically effective amount of atacicept, wherein:
   (a) the atacicept is in an aqueous solution at a concentration of about 150 mg/ml;
   (b) the atacicept solution has a pH of between about 4.9 and about 5.1;
   (c) the patient has an estimated glomerular flow rate (eGFR) of about 35 mL/min/1.73 m2 or higher before the administration, wherein the eGFR is determined by a Chronic Kidney Disease Epidemiology Collaboration (CKD-EPI) formula; and
   (d) the administration results in an at least 25% reduction in the serum level of galactose deficient immunoglobulin A1 (Gd-IgA1) in the patient, compared to before the administration.

2. The method of claim 1, wherein the patient has persistent proteinuria.

3. The method of claim 2, wherein the persistent proteinuria is a persistent proteinuria of 1.0 to 6.0 g/day of total protein based on 24-hour urine collection.

4. The method of claim 2, wherein:
   (a) the persistent proteinuria is a persistent proteinuria with a urine protein:creatinine ratio (UPCR) of ≥1 mg/mg based on 24-hour urine collection; or
   (b) the persistent proteinuria is a persistent proteinuria with a UPCR of ≥0.75 mg/mg based on 24-hour urine collection, wherein at least once within 12 months prior to the administration, the patient has been determined to have a UPCR of ≥1 mg/mg based on 24-hour urine collection.

5. The method of claim 1, wherein the patient has been treated with an angiotensin converting enzyme (ACE) inhibitor and/or an angiotensin receptor blocker (ARB), optionally for at least 8 weeks prior to the administration.

6. The method of claim 1, wherein the atacicept is administered at a dosage of at least 75 mg/week, optionally for a duration of at least 4 weeks.

7. The method of claim 1, wherein the atacicept is administered at a dosage of about 150 mg/week, optionally for a duration of at least 4 weeks.

8. The method of claim 1, wherein the route of administration is subcutaneous.

9. The method of claim 1, wherein the atacicept is obtained from mammalian cells comprising an expression construct encoding the atacicept.

10. The method of claim 9, wherein the mammalian cells are Chinese hamster ovary (CHO) cells.

11. A method for treating a human patient having IgA nephropathy (IgAN), the method comprising administering to the human patient a therapeutically effective amount of atacicept, wherein:
   (a) the atacicept is in an aqueous solution at a concentration of about 150 mg/ml;
   (b) the atacicept solution has a pH of between about 4.9 and about 5.1;
   (c) the patient has an estimated glomerular flow rate (eGFR) of about 35 mL/min/1.73m2 or higher before the administration, wherein the eGFR is determined by a Chronic Kidney Disease Epidemiology Collaboration (CKD-EPI) formula; and
   (d) the administration results in the Estimated Glomerular Filtration Rate (eGFR) of the patient (i) increasing, (ii) remaining stable, or (iii) decreasing by not more than 10%, compared to before the administration.

12. The method of claim 11, wherein the patient has persistent proteinuria.

13. The method of claim 12, wherein the persistent proteinuria is a persistent proteinuria of 1.0 to 6.0 g/day of total protein based on 24-hour urine collection.

14. The method of claim 12, wherein:
   (a) the persistent proteinuria is a persistent proteinuria with a urine protein: creatinine ratio (UPCR) of ≥1 mg/mg based on 24-hour urine collection; or
   (b) the persistent proteinuria is a persistent proteinuria with a UPCR of ≥0.75 mg/mg based on 24-hour urine collection, wherein at least once within 12 months prior to the administration, the patient has been determined to have a UPCR of ≥1 mg/mg based on 24-hour urine collection.

15. The method of claim 11, wherein the patient has been treated with an angiotensin converting enzyme (ACE) inhibitor and/or an angiotensin receptor blocker (ARB), optionally for at least 8 weeks prior to the administration.

16. The method of claim 11, wherein the atacicept is administered at a dosage of at least 75 mg/week, optionally for a duration of at least 4 weeks.

17. The method of claim 11, wherein the atacicept is administered at a dosage of about 150 mg/week, optionally for a duration of at least 4 weeks.

18. The method of claim 11, wherein the route of administration is subcutaneous.

19. The method of claim 11, wherein the atacicept is obtained from mammalian cells comprising an expression construct encoding the atacicept.

20. The method of claim 19, wherein the mammalian cells are Chinese hamster ovary (CHO) cells.

21. A method for treating a human patient having IgA nephropathy (IgAN), the method comprising administering to the human patient a therapeutically effective amount of atacicept, wherein:
   (a) the atacicept is in an aqueous solution at a concentration of about 150 mg;ml;
   (b) the atacicept solution has a pH of between about 4.9 and about 5.1;
   (c) the patient has an estimated glomerular flow rate (eGFR) of about 35 mL/min/1.73m2 or higher before the administration, wherein the eGFR is determined by a Chronic Kidney Disease Epidemiology Collaboration (CKD-EPI) formula; and
   (d) the administration results in an at least a 25% reduction in urine protein: creatinine ratio (UPCR) based on a 24-hour urine collection, compared to before the administration.

22. The method of claim 21, wherein the patient has persistent proteinuria.

23. The method of claim 22, wherein the persistent proteinuria is a persistent proteinuria of 1.0 to 6.0 g/day of total protein based on 24-hour urine collection.

24. The method of claim 22, wherein:
   (a) the persistent proteinuria is a persistent proteinuria with a urine protein: creatinine ratio (UPCR) of ≥1 mg/mg based on 24-hour urine collection; or
   (b) the persistent proteinuria is a persistent proteinuria with a UPCR of ≥0.75 mg/mg based on 24-hour urine collection, wherein at least once within 12 months prior to the administration, the patient has been determined to have a UPCR of ≥1 mg/mg based on 24-hour urine collection.

25. The method of claim 21, wherein the patient has been treated with an angiotensin converting enzyme (ACE) inhibitor and/or an angiotensin receptor blocker (ARB), optionally for at least 8 weeks prior to the administration.

26. The method of claim 21, wherein the atacicept is administered at a dosage of at least 75 mg/week, optionally for a duration of at least 4 weeks.

27. The method of claim 21, wherein the atacicept is administered at a dosage of about 150 mg/week, optionally for a duration of at least 4 weeks.

28. The method of claim 21, wherein the route of administration is subcutaneous.

29. The method of claim 21, wherein the atacicept is obtained from mammalian cells comprising an expression construct encoding the atacicept.

30. The method of claim 29, wherein the mammalian cells are Chinese hamster ovary (CHO) cells.

* * * * *